United States Patent
Freitas Da Costa et al.

(10) Patent No.: US 12,391,701 B2
(45) Date of Patent: Aug. 19, 2025

(54) CHROMENE-BASED COMPOUNDS, METHODS AND USES THEREOF

(71) Applicant: University of Minho, Braga (PT)

(72) Inventors: Marta Sílvia Freitas Da Costa, São Mamede Este (PT); Maria De Fátima Monginho Baltazar, Lago (PT); Maria Fernanda De Jesus Rego Paiva Proença, Braga (PT); Patrícia Maciel, Oporto (PT); Olívia Alexandra Elias Pontes, Morais (PT)

(73) Assignee: UNIVERSITY OF MINHO, Braga (PT)

( * ) Notice: Subject to any disclaimer, the term of this patent is extended or adjusted under 35 U.S.C. 154(b) by 354 days.

(21) Appl. No.: 17/560,859

(22) PCT Filed: Jun. 29, 2020

(86) PCT No.: PCT/IB2020/056131
§ 371 (c)(1),
(2) Date: Dec. 23, 2021

(87) PCT Pub. No.: WO2020/261242
PCT Pub. Date: Dec. 30, 2020

(65) Prior Publication Data
US 2024/0092793 A1    Mar. 21, 2024

(30) Foreign Application Priority Data

Jun. 28, 2019  (PT) .......................................... 115617
Mar. 27, 2020  (EP) .................................... 20166501
Mar. 31, 2020  (WO) .................. PCT/EP2020/059156

(51) Int. Cl.
| C07D 491/052 | (2006.01) |
| A61K 31/4188 | (2006.01) |
| A61P 35/00 | (2006.01) |
| A61P 35/02 | (2006.01) |
| C07D 519/00 | (2006.01) |

(52) U.S. Cl.
CPC ....... *C07D 491/052* (2013.01); *C07D 519/00* (2013.01)

(58) Field of Classification Search
CPC .............. C07D 491/052; C07D 519/00; A61K 31/4188; A61P 35/00; A61P 35/02
See application file for complete search history.

(56) References Cited

FOREIGN PATENT DOCUMENTS

| JP | 28365097 A | 8/2001 |
| WO | WO 2012/110860 A1 | 8/2012 |
| WO | WO 2020/261242 A1 | 12/2020 |

OTHER PUBLICATIONS

Costa, Marta and Proenca, Fernanda, "2-Aryl-1, 9-dihydrochromeno [3, 2-d]imidazoles: a facile synthesis from salicylaldehydes and arylideneaminoacetonitrile". Tetrahedron, 2011, vol. 67, pp. 1799-1804.
International Search Report issued Sep. 2, 2020 in connection with PCT International Application No. PCT/IB2020/056131.
Written Opinion of the International Searching Authority issued Sep. 2, 2020 in connection with PCT International Application No. PCT/IB2020/056131.
International Preliminary Report on Patentability, including Written Opinion of the International Searching Authority, issued Dec. 28, 2021 in connection with PCT International Application No. PCT/IB2020/056131.

*Primary Examiner* — Brenda L Coleman
(74) *Attorney, Agent, or Firm* — Gary J. Gershik

(57) ABSTRACT

The present disclosure relates to a compound or a pharmaceutically acceptable salt, hydrate, solvate, N-oxide, stereoisomer, diastereoisomer, enantiomer, atropisomer, dimer, or polymorph for use in medicine comprising the following formula:

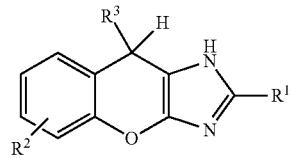

wherein
$R^1$, $R^2$ and $R^3$ are independently selected from each other;
$R^1$ is selected from an aryl, or heterocyclic ring;
$R^2$ is selected from a H, alkyl, aryl, alcoxyl, halogen, hydroxyl, amine, carbonyl, or heterocyclic ring;
$R^3$ is selected from a H, or

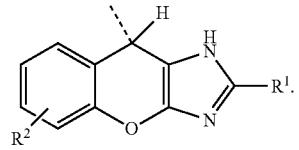

11 Claims, 27 Drawing Sheets

EXHIBIT B

|  | Females | | Males | |
| --- | --- | --- | --- | --- |
|  | Vehicle | MC408 | Vehicle | MC408 |
| Body position | Normal | Normal | Normal | Normal |
| Spontaneous activity | Normal | Normal | Normal | Normal |
| Respiratory rate | Normal | Normal | Normal | Normal |
| Eyelid opening | Present | Present | Present | Present |
| Eyelid reflexes | Normal | Normal | Normal | Normal |
| Body curvature | Normal | Normal | Normal | Normal |
| Skin picking (dehydration) | Normal | Normal | Normal | Normal |
| Reaction to transfer | Normal | Normal | Normal | Normal |
| Limb clasping | Absent | Absent | Absent | Absent |
| Grooming | Present | Present | Present | Present |
| Fur erection | Absent | Absent | Absent | Absent |
| Tremors | Absent | Absent | Absent | Absent |

Fig. 14

CHROMENE-BASED COMPOUNDS, METHODS AND USES THEREOF

CROSS-REFERENCE TO RELATED APPLICATIONS

This application is a § 371 national stage of PCT International Application No. PCT/IB2020/056131, 2020, filed Jun. 29, 2020, claiming the benefit of PCT International Application No. PCT/EP2020/059156, filed Mar. 31, 2020, European Patent Application No. 20166501.5, filed Mar. 27, 2020, and Portuguese Patent Application No. 115617, filed Jun. 28, 2019, the entire contents of each of which are hereby incorporated by reference into the subject application.

TECHNICAL FIELD

The present disclosure relates to a novel class of chromene-based anti-cancer compounds. The present disclosure describes the anti-cancer properties of the novel class of chromene-based anti-cancer compounds. This disclosure further describes the method of synthesizing and isolating the novel class of chromene-based anti-cancer compounds.

BACKGROUND

Cancer was responsible for the death of almost 10 million people worldwide in 2018 and 18.1 million new cases of cancer were detected in the same year.[1] The prevalence of this illness after 5 years is expected to be more than 43 million cases. This justifies the urgency of finding new and better treatments. This problem has to be addressed on a global scale due to the overall increase in the number of cases and associated mortality. Breast cancer was responsible for 6.6% of deaths by cancer in 2018. Breast cancer is the fifth most lethal type of cancer; 11.6% new cases were detected in 2018 (more than 2 million cases).[2] This is the second most frequent cancer type in terms of incidence. The type of treatment always depends on the cancer stage, but essentially consist of surgery, radiation, conventional chemotherapy, immunotherapy or molecular therapy in cases where molecular markers such as ER, PR and HER-2 are detected. However, in the case of a triple negative breast cancer (TNBC), a very aggressive subtype of breast cancer that accounts for approximately 15%-20% of all breast cancers, conventional therapy has limited efficacy and no molecular or personalized therapy has been developed yet. Due to this bad prognosis, a high mortality is associated with this subtype of breast cancer.[3]

Chromene-based scaffolds have inspired medicinal chemists as these compounds are widely present in nature and have a variety of biological properties.[4] Research about the synthesis and biological importance of this naturally occurring scaffold and its synthetic derivatives have been gaining attraction over the last few years.

Document "Tetrahedron" by Costa et al describes a one-pot cascade reaction involving salicylaldehydes and arylideneaminoacetonitriles for preparing 2-Aryl-1,9-dyhydro-chromeno[3,2-d]imidazoles. The document further describes the new fused tricyclic systems combining chromene and imidazole as alternative drug candidates with improved pharmacological properties. However, the described system does not allow molecules where the aromatic units incorporate different substituents to be generated.

These facts are disclosed in order to illustrate the technical problem addressed by the present disclosure.

GENERAL DESCRIPTION

The present disclosure relates to a novel class of chromene-based anti-cancer compounds. The present disclosure describes the anti-cancer properties of the novel class of chromene-based anti-cancer compounds. This disclosure further describes the method of synthesizing and isolating the novel class of chromene-based anti-cancer compounds.

Specifically, the present disclosure describes the method of synthesising new chromene-based compounds by combining at least two different molecules thus giving rise to compounds with an interesting associated biological profile.

The chromene-based compound synthesis process described in the prior art does not allow the isolation of these novel compounds. The method described in this disclosure allows the synthesis and isolation of novel chromene-based compounds that are surprisingly effective when used as anticancer compounds in several cancer subtypes such as breast cancer, renal cell carcinoma, acute leukemia and glioma. The compounds are especially effective against breast cancer and renal cell carcinoma In an embodiment, the synthesized compounds were tested for their anticancer potential by in vitro screening using the appropriate cell lines. The activity of the compounds was explored at different levels, including the effects on cell viability, proliferation, migration, invasion, cell death and metabolism.

In an embodiment, the toxicity effect of the chromene-based compounds was also tested in non-neoplastic cell lines.

In an embodiment, the *Caenorhabditis elegans* (*C. elegans* nematode) model was used for an early stage in vivo toxicity screening of the chromene-based compounds. In vivo toxicity was also evaluated using the mouse as model.

In an embodiment, the anticancer properties of the chromene-based compounds were also characterized using in vivo CAM (chicken chorioallantoic membrane) assay, evaluating the efficacy and angiogenesis properties of the novel chromenes. In vivo efficacy was further evaluated using the mouse as a model.

The compound of the present subject-matter exhibits a unique and promising anticancer profile.

One aspect of the present disclosure relates to a compound or a pharmaceutically acceptable salt, hydrate, solvate, N-oxide, stereoisomer, diastereoisomer, enantiomer, atropisomer, dimer, or polymorph comprising the following formula:

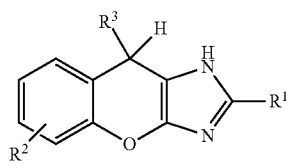

wherein
$R^1$, $R^2$ and $R^3$ are independently selected from each other;
$R^1$ is selected from a H, alkyl, aryl, alcoxyl, acyl, halogen, nitro, hydroxyl, amine, amide, ketone, ester, heterocyclic ring;

R² is selected from a H, alkyl, aryl, alcoxyl, acyl, halogen, nitro, hydroxyl, amine, amide, carbonyl, ketone, ester, heterocyclic ring;

R³ is selected from a H, alkyl, aryl, alcoxyl, acyl, halogen, nitro, hydroxyl, amine, amide, ketone, ester, heterocyclic ring or

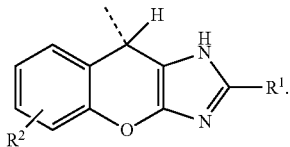

Another aspect of the present disclosure relates to a compound or a pharmaceutically acceptable, salt, hydrate, solvate, N-oxide, stereoisomer, diastereoisomer, enantiomer, atropisomer, dimer, or polymorph comprising the following formula:

R¹ is selected from an aryl, or heterocyclic ring;

R² is selected from a H, alkyl, aryl, alcoxyl, halogen, hydroxyl, amine, carbonyl, or heterocyclic ring;

R³ is selected from a H, or

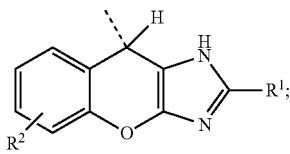

preferably with the proviso that

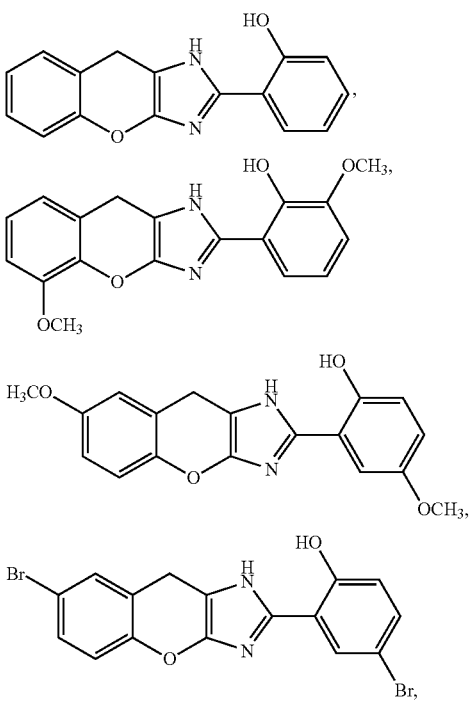

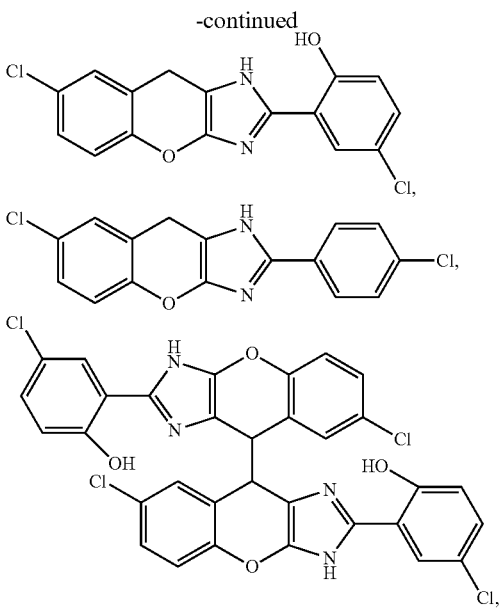

are excluded.

In an embodiment, the compound or a pharmaceutically acceptable, salt, hydrate, solvate, N-oxide, stereoisomer, diastereoisomer, enantiomer, atropisomer, dimer, or polymorph according wherein: R¹ is selected is aryl; and R² is selected H, alkyl, alcoxyl, halogen, hydroxyl or amine.

In an embodiment, the compound or a pharmaceutically acceptable, salt, hydrate, solvate, N-oxide, stereoisomer, diastereoisomer, enantiomer, atropisomer, dimer, or polymorph wherein, the dimer is preferably homodimer.

In an embodiment, the compound or a pharmaceutically acceptable, salt, hydrate, solvate, N-oxide, stereoisomer, diastereoisomer, enantiomer, atropisomer, dimer, or polymorph wherein R¹ is a substituted aryl.

In an embodiment, the compound or a pharmaceutically acceptable, salt, hydrate, solvate, N-oxide, stereoisomer, diastereoisomer, enantiomer, atropisomer, dimer, or polymorph wherein R¹ is selected from the following list: hydroxyphenyl, hydroxy-methoxyphenyl, hydroxy-bromophenyl, hydroxy-chlorophenyl, fluorophenyl, bromophenyl, 24-chlorophenyl, phenyl, methoxyphenyl, difluoro-hydroxyphenyl, ethoxyphenyl or bromo-hydroxymethoxyphenyl.

In an embodiment, the compound or a pharmaceutically acceptable, salt, hydrate, solvate, N-oxide, stereoisomer, diastereoisomer, enantiomer, atropisomer, dimer, or polymorph wherein R¹ is 2-hydroxyphenyl, 2-hydroxy-3-methoxyphenyl, 2-hydroxy-5-methoxyphenyl, 2-hydroxy-5-bromophenyl, 2-hydroxy-5-chlorophenyl, 4-fluorophenyl, 4-bromophenyl, 2-fluorophenyl, 3-fluorophenyl, 4-chlorophenyl, phenyl, 3-hydroxyphenyl, 2-hydroxyphenyl, 2-methoxyphenyl, 3,5-difluoro-2-hydroxyphenyl, 4-ethoxyphenyl or 2-bromo-3-hydroxy-4-methoxyphenyl.

In an embodiment, the compound or a pharmaceutically acceptable, salt, hydrate, solvate, N-oxide, stereoisomer, diastereoisomer, enantiomer, atropisomer, dimer, or polymorph wherein R² is a substituted or unsubstituted aryl.

In an embodiment, the compound or a pharmaceutically acceptable, salt, hydrate, solvate, N-oxide, stereoisomer, diastereoisomer, enantiomer, atropisomer, dimer, or polymorph wherein R² is selected from the following list: H, 5-methoxy, 7-methoxy, 7-bromo, 7-chloro or 7-fluoro.

In an embodiment, the compound or a pharmaceutically acceptable, salt, hydrate, solvate, N-oxide, stereoisomer, diastereoisomer, enantiomer, atropisomer, dimer, or polymorph wherein $R^3$ is a chromene unit or H.

In an embodiment, the compound or a pharmaceutically acceptable, salt, hydrate, solvate, N-oxide, stereoisomer, diastereoisomer, enantiomer, atropisomer, dimer, or polymorph wherein $R^3$ is selected from the following list: H, 2-(4-fluorophenyl)-5-methoxy-1,9-dihydrochromeno[2,3-d]imidazole unit, 2-(4-bromophenyl)-5-methoxy-1,9-dihydrochromeno[2,3-d]imidazole unit or 2-(2-fluorophenyl)-5-methoxy-1,9-dihydrochromeno[2,3-d]imidazole unit.

In an embodiment, the compound or a pharmaceutically acceptable, salt, hydrate, solvate, N-oxide, stereoisomer, diastereoisomer, enantiomer, atropisomer, dimer, or polymorph wherein the compound is selected from the following list:

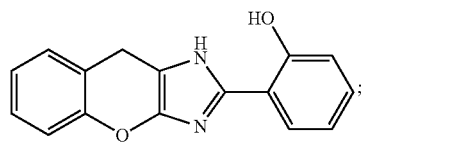
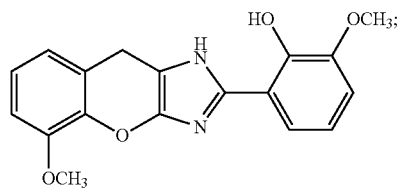
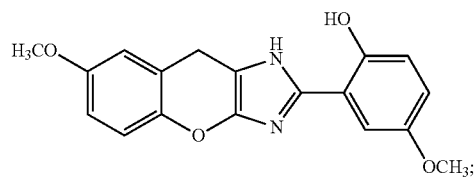
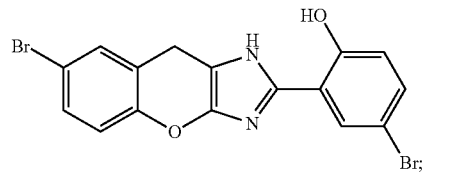
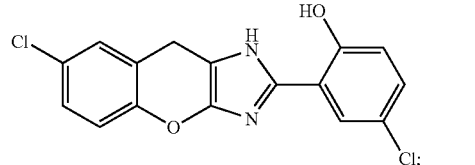
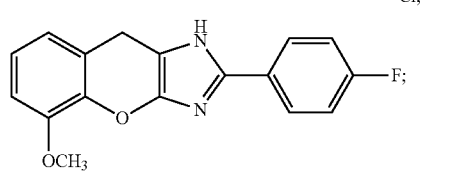
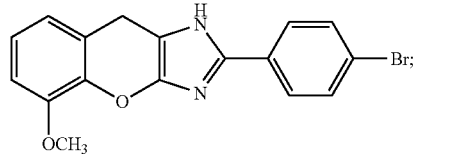

-continued

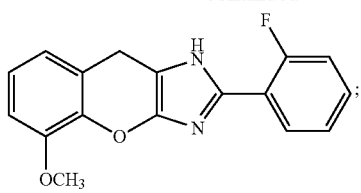
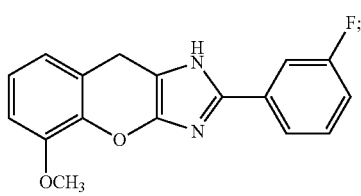
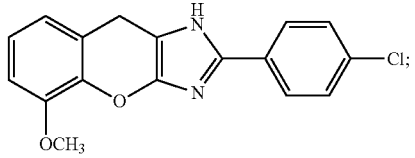
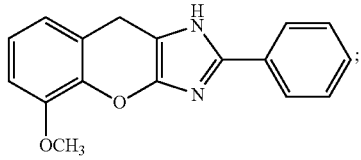
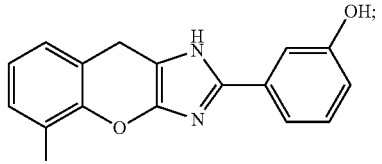
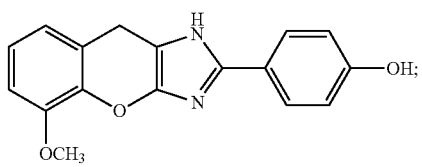
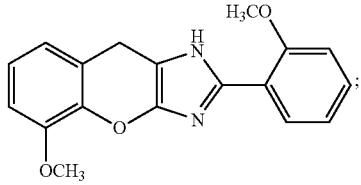
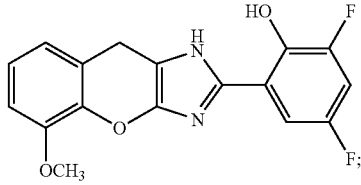
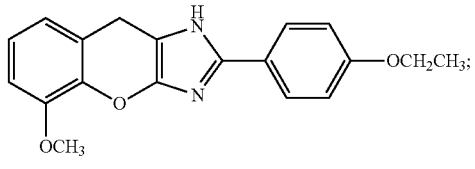

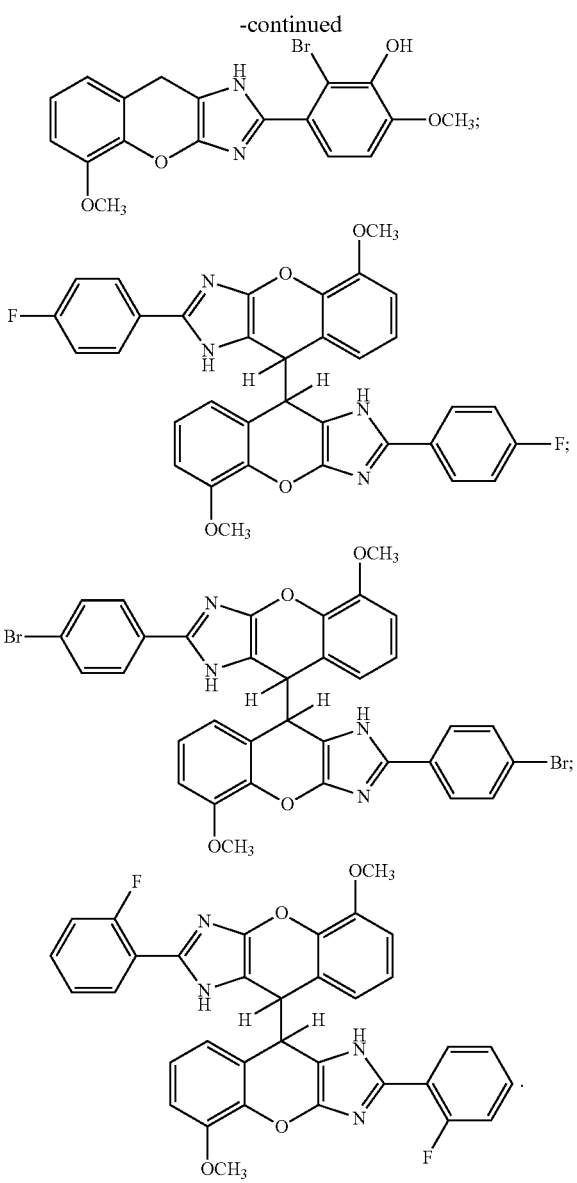

In one aspect of the present disclosure, the compound disclosed is used in medicine or veterinary medicine.

In one aspect of the present disclosure, the compound may be used in the treatment, therapy or diagnostic of a disease characterized by benign or malignant cellular hyperproliferation, or by areas of neovascularisation or hypervascularization, or a cancer.

In one aspect of the present disclosure, the compound may be used in the treatment, therapy or diagnostic of hyperproliferative tissue or a neoplasia.

In one aspect of the present disclosure, the compound may be used in the treatment, therapy or diagnostic of breast cancer, renal cell carcinoma, leukemia, glioma or glioblastoma.

In one aspect of the present disclosure, the compound may be used in the treatment, therapy or diagnostic of renal cell carcinoma, leukemia, glioma, glioblastoma, breast cancer.

In one aspect of the present disclosure, the compound may be use in the treatment, therapy or diagnostic triple-negative breast cancer, acute renal cell carcinoma, luminal breast cancer, a basal like breast cancer, acute leukemia.

Another aspect of the present disclosure relates to a pharmaceutical composition comprising at least one of the compounds disclosed.

In an embodiment, the pharmaceutical composition disclosed further comprising a pharmaceutically acceptable carrier.

In an embodiment, the pharmaceutical composition disclosed further comprising an anti-viral, an analgesic, an anti-inflammatory agent, a chemotherapy agent, a radiotherapy agent, an antibiotic, antifungal, antiparasitic, or a diuretic, or mixtures thereof.

In an embodiment, the pharmaceutical composition disclosed further comprising a filler, a binder, a disintegrant, a lubricant, or mixtures thereof.

In an embodiment, the pharmaceutical composition disclosed is used in intradermal, or transdermal therapies, or topic, or systemic, or intravenous therapies, or combinations thereof.

Another aspect of the present disclosure relates to a method for obtaining the disclosed compound comprises the following steps:
   adding a concentrate HCl (1.1 equivalent) to an orange solution of 2-imino-8-methoxy-2H-chromen-3-amine (0.150 mg; 0.79 mmol) in 1 mL of CH$_3$CN;
   stirring the mixture at room temperature (20° C.) for 10-15 minutes (an immediate precipitation is observed);
   filtering the solid, preferably by simple filtration, to obtain 3-amino-8-methoxy-2H-chromen-2-iminium chloride;
   adding aldehyde (1.1-1.7 equivalent) to the suspension of 3-amino-8-methoxy-2H-chromen-2-iminium chloride (0.25-0.35 mmol) in CH$_3$CN (1-2 mL);
   stirring the suspension at 60° C. for 24-48 hours,
   filtering the obtained solid to isolate the pure product, preferably washed with CH3CN; optionally when contamination with HCl was observed in the 1H NMR spectrum, the solid was washed with an aqueous solution of NaHCO3 (0.05 M), filtered and washed with water, leading to the pure product 2-(5-methoxy-3,9-dihydrochromeno[2,3-d]imidazoles.

In an embodiment, for the preparation of the 5,5'-dimethoxy-2,2'-diphenyl-1,1',9,9'-tetrahydro-9,9'-bichromeno[2,3-d]imidazoles, adding aldehyde (1-1.2 equivalent) to a solution of 2-imino-8-methoxy-2H-chromen-3-amine in CH3CN (1-2 mL) and stirring the solution at 80° C. for 7-24 hours. The solid product started to precipitate slowly, was filtered, washed with CH3CN and identified as the pure product 5,5'-dimethoxy-2,2'-diphenyl-1,1',9,9'-tetrahydro-9,9'-bichromeno[2,3-d]imidazole.

Another aspect of the present disclosure relates to a nanoparticle comprising the disclosed compound and/or the disclosed pharmaceutical composition.

In an embodiment, the nanoparticle comprising the disclosed compound and/or pharmaceutical composition is encapsulated by the nanoparticle.

Another aspect of the present disclosure relates to a kit comprising the compound and/or the disclosed pharmaceutical composition.

Another aspect of the present disclosure relates to the use of the compound or a pharmaceutically acceptable, salt, hydrate, solvate, N-oxide, stereoisomer, diastereoisomer, enantiomer, atropisomer, dimer, or polymorph for use in medicine or veterinary. Specifically, for use in the treatment or therapy of a disease characterized by benign or malignant cellular hyperproliferation, or by areas of neovascularisation, or a cancer. In particular, for use in the treatment, therapy or diagnosis of hyperproliferative tissue, such as hyperproliferative tissue associated with cancer. Additionally, for use in the treatment, therapy or diagnosis of breast cancer, renal cell carcinoma, acute leukemia and glioma. Furthermore, for use in the treatment, therapy or diagnostic of glioblastoma and triple-negative breast cancer.

Based on the International Union of Pure and Applied Chemistry (IUPAC) definitions, an alkyl group is defined as a univalent group derived from alkanes by removal of a hydrogen atom from any carbon atom —$C_nH_{2n+1}$. The groups derived by removal of a hydrogen atom from a terminal carbon atom of unbranched alkanes form a subclass of normal alkyl (n-alkyl) groups H $(CH_2)_n$. The groups $RCH_2$, $R_2CH$ (R≠H), and $R_3C$ (R≠H) are primary, secondary and tertiary alkyl groups respectively. An aryl group is derived from arenes (monocyclic and polycyclic aromatic hydrocarbons) by removal of a hydrogen atom from a ring carbon atom.

"Alkyl" includes "lower alkyl" and extends to cover carbon fragments having up to 30 carbon atoms. Examples of alkyl groups include octyl, nonyl, norbornyl, undecyl, dodecyl, tridecyl, tetradecyl, pentadecyl, eicosyl, 3,7-diethyl-2,2-dimethyl-4-propylnonyl, 2-(cyclododecyl)ethyl, adamantyl, and the like.

"Lower alkyl" means alkyl groups with 1 to 7 carbon atoms. Examples of lower alkyl groups include methyl, ethyl, propyl, isopropyl, butyl, sec- and tert-butyl, pentyl, hexyl, heptyl, cyclopropyl, cyclobutyl, cyclopentyl, cyclohexyl, cycloheptyl, 2-methylcyclopropyl, cyclopropylmethyl, and the like.

In the present disclosure, halogen refers to an element selected from the list consisting of: fluorine (F), chlorine (Cl), bromine (Br), iodine (I), astatine (At).

In the present disclosure, the term "heterocyclic ring" denotes a ring wherein at least one of the atoms forming the ring backbone is not a carbon. Unless otherwise indicated, a heterocyclic ring can be a saturated, partially unsaturated, or fully unsaturated ring. "Saturated heterocyclic ring" refers to a heterocyclic ring containing only single bonds between ring members. "Partially saturated heterocyclic ring" refers to a non-aromatic heterocyclic ring containing at least one double bond. The term "heteroaromatic ring" denotes a fully unsaturated aromatic ring in which at least one atom forming the ring backbone is not a carbon. Typically, a heteroaromatic ring contains no more than 4 nitrogens, no more than 1 oxygen, and no more than 1 sulfur. Unless otherwise indicated, heteroaromatic rings can be attached through any available carbon or nitrogen by replacement of a hydrogen atom on said carbon or nitrogen. The term "heteroaromatic bicyclic ring system" denotes a ring system consisting of two fused rings in which at least one of the two rings are a heteroaromatic ring as defined above.

The term "carbocyclic ring" denotes a ring wherein the atoms forming the ring backbone are selected only from carbon. Unless otherwise indicated, a carbocyclic ring can be a saturated, partially unsaturated, or fully unsaturated ring. When a fully unsaturated carbocyclic ring satisfies Huckel's rule, then said ring is also called an "aromatic ring". "Saturated carbocyclic ring" refers to a ring having a backbone consisting of carbon atoms linked to one another by single bonds; unless otherwise specified, the remaining carbon valences are occupied by hydrogen atoms.

BRIEF DESCRIPTION OF THE DRAWINGS

The following figures provide preferred embodiments for illustrating the disclosure and should not be seen as limiting the scope of invention.

FIG. 4A are representative dot plots of MCF-7 cells treated with 0.5% DMSO (control) or treated for 12 hours and 24 hours with $IC_{50}$ concentrations of the compounds. FIG. 4B shows the quantification of the percentage of cells in each quadrant of the dot plots.

FIG. 5A are representative dot plots of Hs578t cells treated with 0.5% DMSO (control) or treated for 12 and 24 hours with $IC_{50}$ concentrations of the agents. FIG. 5B shows the quantification of the percentage of cells in each quadrant of the dot plots.

FIG. 8A are representative histograms with cell cycle profile of MCF-7 cells treated with 0.5% DMSO (control) or treated for 12 and 24 hours with the $IC_{50}$ concentrations of the agents. FIG. 8B shows the quantification of the cells in different phases of the cell cycle.

FIG. 9A are representative histograms with cell cycle profile of Hs578t cells treated with 0.5% DMSO (control) or treated for 12 hours and 24 hours with the $IC_{50}$ concentrations for the agents. FIG. 9B shows the quantification of the cells in different phases of the cell cycle.

FIG. 14 shows the results of a battery of welfare test conducted on C57BI/6 mice treated with compound MC408.

FIG. 16A is a schematic representation of the experiment timeline. FIG. 16B shows the body weight of the mice.

FIG. 17A shows representative pictures of CAM assay and FIG. 17B shows tumor growth percentages.

FIG. 18A are representative dot plots of 786-O cells treated with 0.5% DMSO (control) or treated for 24 and 48 hours with $IC_{50}$ concentrations of the agents. FIG. 18B shows the quantification of the percentage of cells in each quadrant of the dot plots.

FIG. 21A shows representative pictures of CAM assay and FIG. 21B shows tumor growth percentages.

FIG. 22A are representative histograms with cell cycle profile of 786-O cells treated with 0.5% DMSO (control) or treated for 24 and 48 hours with the $IC_{50}$ concentrations of the agents. FIG. 22B shows the quantification of the cells in different phases of cell cycle.

DETAILED DESCRIPTION

Figure 1:
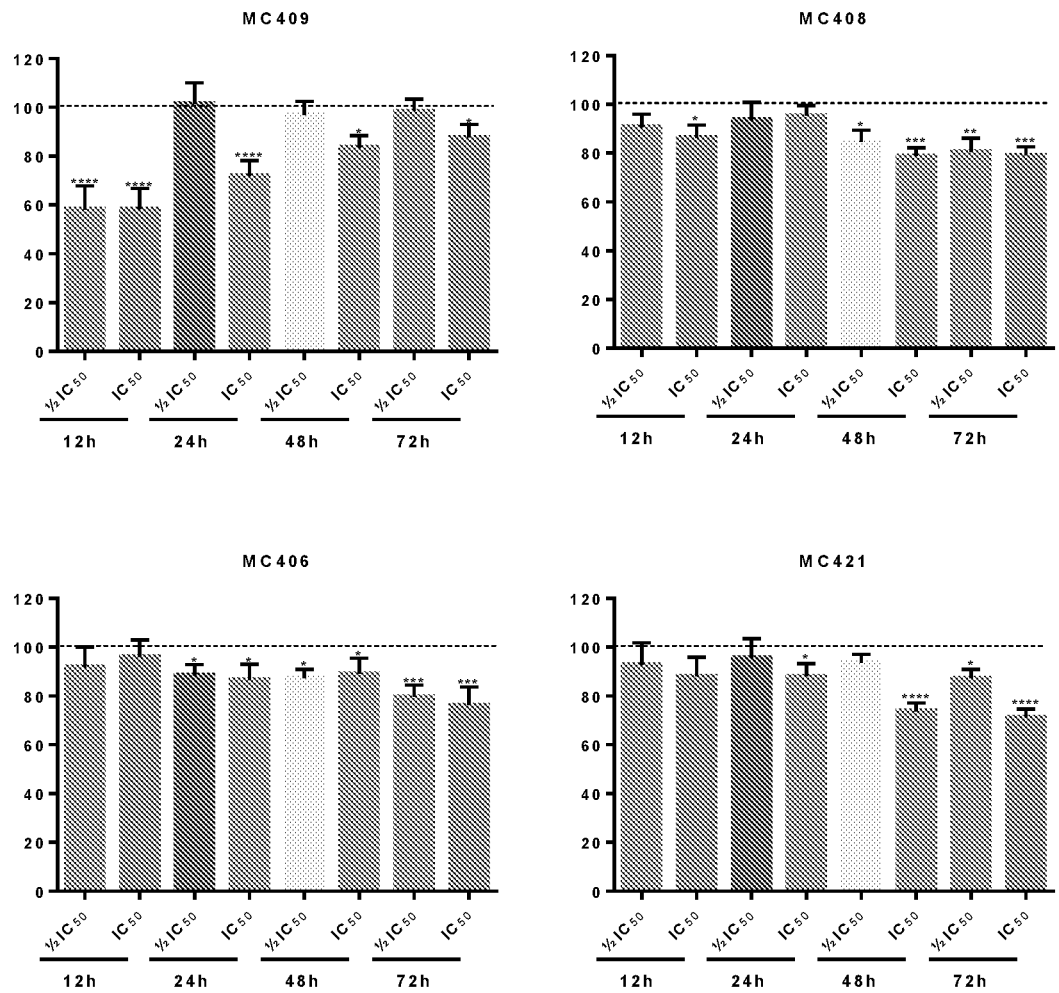
FIG. 1 shows the effect of the chromene-based compounds on MCF-7 cell migration (12, 24, 48, 72 hours of treatment with the respective ½$IC_{50}$ and $IC_{50}$ value for each compound), assessed by the wound-healing assay.

The present disclosure relates to a novel class of chromene-based anti-cancer compound. The present disclosure describes the anti-cancer properties of the novel class of chromene-based anti-cancer compounds. This disclosure further describes the method of synthesizing and isolating the novel class of chromene-based anti-cancer compounds.

Specifically, the present disclosure describes the method of synthesizing new chromene-based compounds by combining at least two different molecules thus giving rise to compounds with an interesting associated biological profile.

In an embodiment, 19 different chromene-imidazole based compounds were isolated. Table 1 shows the structure of the chromene-based scaffolding as well as the 19 synthesised and isolated chromene-imidazole based compounds.

TABLE 1

Structure of the chromene-based compounds

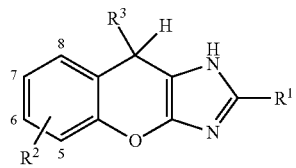

| Isolated compounds | | $R^1$ moiety | $R^2$ moiety | $R^3$ moiety |
|---|---|---|---|---|
| 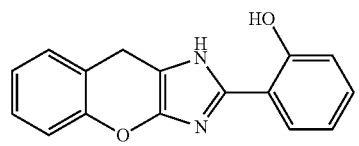 | M1159 | 2-hydroxyphenyl | H | H |

TABLE 1-continued

Structure of the chromene-based compounds

| Isolated compounds | | R¹ moiety | R² moiety | R³ moiety |
|---|---|---|---|---|
| | M955 | 2-hydroxy-3-methoxyphenyl | 5-methoxy | H |
| | M1220 | 2-hydroxy-5-methoxyphenyl | 7-methoxy | H |
| | M1221 | 2-hydroxy-5-bromophenyl | 7-bromo | H |
| | M1143 | 2-hydroxy-5-chlorophenyl | 7-chloro | H |
| | MC409 | 4-fluorophenyl | 5-methoxy | H |
| | MC408 | 4-bromophenyl | 5-methoxy | H |
| | MC407 | 2-fluorophenyl | 5-methoxy | H |

TABLE 1-continued

Structure of the chromene-based compounds

| Isolated compounds | | R¹ moiety | R² moiety | R³ moiety |
|---|---|---|---|---|
| | MC349 | 3-fluorophenyl | 5-methoxy | H |
| | MC412 | 4-chlorophenyl | 5-methoxy | H |
| | MC350 | phenyl | 5-methoxy | H |
| | MC359 | 3-hydroxyphenyl | 5-methoxy | H |
| | MC413 | 4-hydroxyphenyl | 5-methoxy | H |
| | MC411 | 2-methoxyphenyl | 5-methoxy | H |
| | MC410 | 3,5-difluoro-2-hydroxyphenyl | 5-methoxy | H |

TABLE 1-continued

Structure of the chromene-based compounds

| Isolated compounds | | R¹ moiety | R² moiety | R³ moiety |
|---|---|---|---|---|
| | MC415 | 4-ethoxyphenyl | 5-methoxy | H |
| | MC416 | 2-bromo-3-hydroxy-4-methoxyphenyl | 5-methoxy | H |
| | MC406 | 4-fluorophenyl | 5-methoxy | |
| | MC421 | 4-bromophenyl | 5-methoxy | |
| | MC369 | 2-fluorophenyl | 5-methoxy | |

In an embodiment, the cell growth inhibition and $IC_{50}$ values of the synthesised and isolated chromene-based compounds were determined as part of the evaluation of the antiproliferative activity of the isolated agents. A complete study on the structure-activity relationship was performed for all the synthesised compounds. The antiproliferative activity against MCF-7 breast cancer cell lines were analysed. Table 2 shows the $IC_{50}$ values (μM) and selectivity index (SI) of the compounds for breast cancer cell line MCF-7 and non-neoplastic cell line MCF-10A. The non-neoplastic cell line MCF-10A was also used to determine the selectivity of the compounds for the tumour cells. For compounds with an $IC_{50}$ value (concentration required to reduce cell viability by 50%) higher than 20 μM, the $IC_{50}$ value was not determined. Selectivity index (SI) was calculated in order to evaluate the cytotoxicity of the tested compounds.

TABLE 2
IC$_{50}$ values (μM) and selectivity index (SI) of the compounds for breast cancer cell line MCF-7 and non-neoplastic cell line MCF-10A
| | | Cell line | | |
|---|---|---|---|---|
| Agent | | MCF-7 IC$_{50}$ (μM) | MCF-10A IC$_{50}$ (μM) | SI |
| 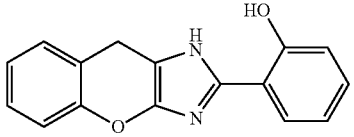 [SMILES: Oc1ccccc1-c1nc2c([nH]1)Cc1ccccc1O2] | M1159 | 3.68 | >30 | >7 |
| 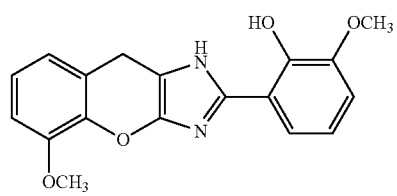 | M955 | 4.15 | >30 | >6 |
| 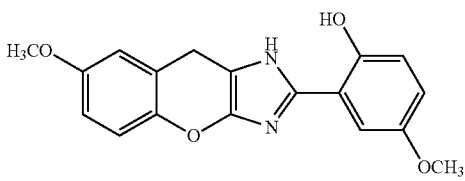 [SMILES: COc1ccc2c(c1)Cc1[nH]c(-c3cc(OC)ccc3O)nc1O2] | M1220 | 5.85 | >30 | >4 |
| 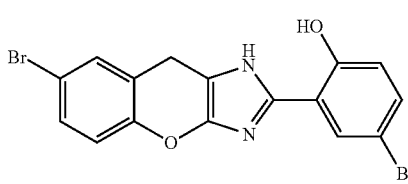 | M1221 | >30 | — | — |
| 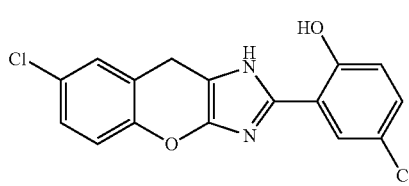 | M1143 | >30 | — | — |
| 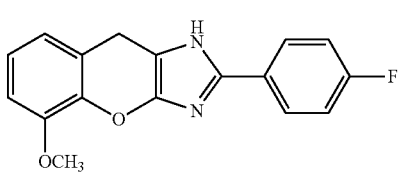 [SMILES: COc1cccc2c1Oc1nc(-c3ccc(F)cc3)[nH]c1C2] | MC409 | 0.65 | 14.28 | 21.0 |
| 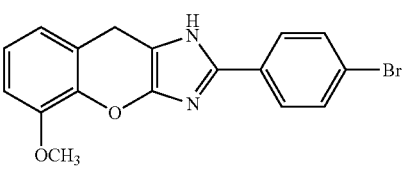 | MC408 | 0.62 | 2.99 | 3.8 |
| 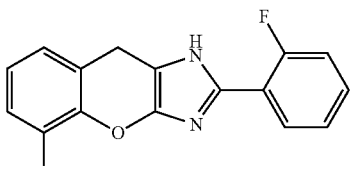 | MC407 | 0.67 | 3.93 | 8.8 |

TABLE 2-continued
IC$_{50}$ values (μM) and selectivity index (SI) of the compounds for breast cancer cell line MCF-7 and non-neoplastic cell line MCF-10A
| Agent | | MCF-7 IC$_{50}$ (μM) | MCF-10A IC$_{50}$ (μM) | SI |
|---|---|---|---|---|
| 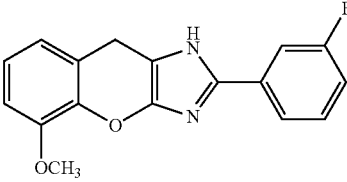 [SMILES: COc1cccc2c1Oc1nc(-c3ccccc3F)[nH]c1C2] | MC349 | 0.77 | 2.30 | 2.0 |
| 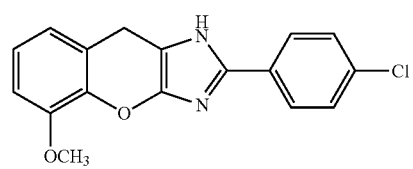 [SMILES: COc1cccc2c1Oc1nc(-c3ccc(Cl)cc3)[nH]c1C2] | MC412 | 0.44 | 1.74 | 3.0 |
| 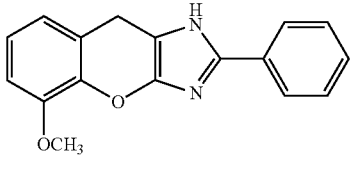 | MC350 | 0.74 | 8.46 | 10.4 |
| 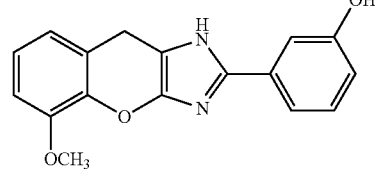 | MC359 | 2.82 | 6.66 | 1.4 |
| 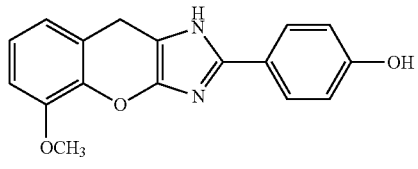 [SMILES: COc1cccc2c1Oc1nc(-c3ccc(O)cc3)[nH]c1C2] | MC413 | 1.09 | >20 | >17 |
| 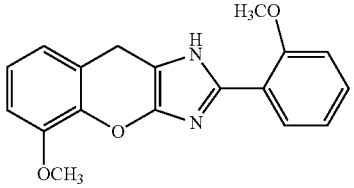 [SMILES: COc1ccccc1-c1nc2c([nH]1)Cc1cccc(OC)c1O2] | MC411 | 1.71 | 6.82 | 3.0 |
| 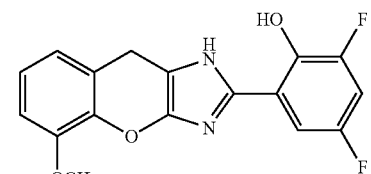 | MC410 | 3.53 | >30 | >7 |
| 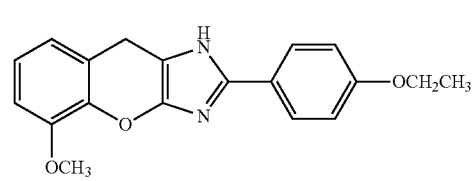 [SMILES: CCOc1ccc(-c2nc3c([nH]2)Cc2cccc(OC)c2O3)cc1] | MC415 | 1.64 | 1.90 | 0.2 |

TABLE 2-continued

IC$_{50}$ values (µM) and selectivity index (SI) of the compounds for breast cancer cell line MCF-7 and non-neoplastic cell line MCF-10A

| Agent | MCF-7 IC$_{50}$ (µM) | MCF-10A IC$_{50}$ (µM) | SI |
|---|---|---|---|
| MC416 | 1.04 | 1.99 | 0.86 |
| MC406 | 0.20 | 12.71 | 62.6 |
| MC421 | 0.31 | >30 | >96 |
| MC369 | 0.26 | >20 | >76 |

The dimeric compounds presented excellent IC$_{50}$ values for MCF-7 cell line, lower values than the respective monomers. Monomeric compounds bearing a halogen atom or no substituent in the aromatic ring linked to the imidazole moiety presented the lowest IC$_{50}$ values (<1 µM). Imidazochromenes bearing OH or OCH$_3$/OCH$_2$CH$_3$ led to significantly higher IC$_{50}$ values, even when a halogen atom is present in the same aromatic moiety.

For the non-neoplastic cell line MCF-10A, promising IC$_{50}$ values were also obtained for some chromenes and high SI values were calculated. Toxicity toward non-neoplastic cells was much lower for the dimeric compounds, leading to excellent SI values (higher than 60). The SI values were in general very promising.

In an embodiment, for a comparison study, monomers and respective dimers were selected and further evaluated in Hs578t and MDA-MB-468 breast cell lines. Table 3 shows the IC$_{50}$ values (µM) and selectivity index (SI) of selected chromene-based compounds for breast cancer cell lines Hs578t and MDA-MB-468. These cell lines correspond to the basal-like subtype of breast cancer, included in the known triple negative subtype, since they are negative for Estrogen receptor (ER), progesterone receptor (PR) and Human epidermal growth factor receptor 2 (HER2) molecular markers. The clinical behaviour of these breast cancer subtype is very aggressive and there is still no specific molecular therapy available.

TABLE 3

IC$_{50}$ values (µM) and selectivity index (SI) of selected chromene-based compounds for TNBC cell lines MDA-MB-468, MDA-MB-231 and Hs578t.

| Agent | | MDA-MB-468 | SI MDA-MB-468 vs MCF-10A | MDA-MB-231 | SI MDA-MB-231 vs MCF-10A | Hs578t | SI Hs578t vs MCF-10A |
|---|---|---|---|---|---|---|---|
| (structure) | MC406 | 0.32 | 38.7 | 1.29 | 38.9 | 0.053 | 238.8 |
| (structure) | MC421 | 0.44 | >67 | 2.96 | >9 | 0.035 | >850 |
| (structure) | MC369 | — | — | 2.52 | >6 | — | — |
| (structure) | MC409 | 0.12 | 118.0 | 2.70 | 4.3 | 0.27 | 51.8 |

TABLE 3-continued
IC$_{50}$ values (μM) and selectivity index (SI) of selected chromene-based compounds for TNBC cell lines MDA-MB-468, MDA-MB-231 and Hs578t.
| Agent | | MDA-MB-468 | SI MDA-MB-468 vs MCF-10A | MDA-MB-231 | SI MDA-MB-231 vs MCF-10A | Hs578t | SI Hs578t vs MCF-10A |
|---|---|---|---|---|---|---|---|
| 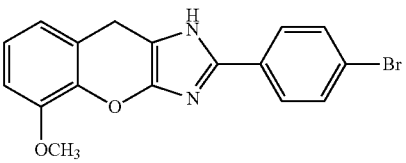 [SMILES: COc1cccc2c1Oc1nc(-c3ccc(Br)cc3)[nH]c1C2] | MC408 | 0.027 | 109.7 | 2.56 | 0.2 | 0.047 | 62.6 |
| 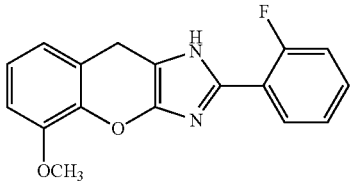 [SMILES: COc1cccc2c1Oc1nc(-c3ccccc3F)[nH]c1C2] | MC407 | — | — | 1.65 | 1.4 | — | — |
| 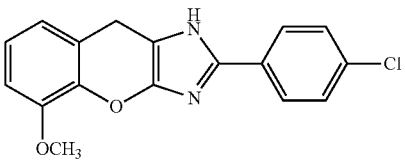 | MC412 | — | — | 1.67 | 0.04 | 0.98 | 0.8 |
| 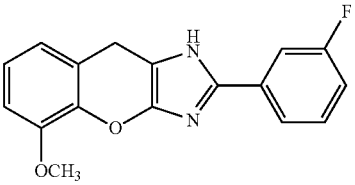 [SMILES: COc1cccc2c1Oc1nc(-c3cccc(F)c3)[nH]c1C2] | MC349 | — | — | 1.23 | 0.9 | 0.64 | 2.6 |
| 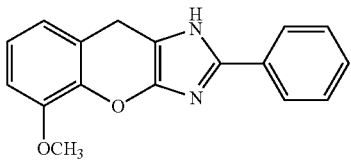 [SMILES: COc1cccc2c1Oc1nc(-c3ccccc3)[nH]c1C2] | MC350 | — | — | 2.52 | 2.4 | — | — |
| 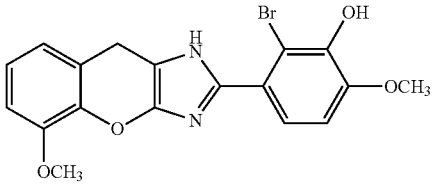 [SMILES: COc1ccc(-c2nc3c([nH]2)Cc2cccc(OC)c2O3)c(Br)c1O] | MC416 | — | — | — | — | 3.16 | -0.4 |
| 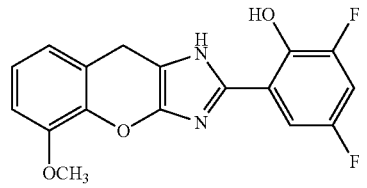 [SMILES: COc1cccc2c1Oc1nc(-c3cc(F)cc(F)c3O)[nH]c1C2] | MC410 | — | — | >30 | — | >20 | — |

TABLE 3-continued
IC$_{50}$ values (μM) and selectivity index (SI) of selected chromene-based compounds
for TNBC cell lines MDA-MB-468, MDA-MB-231 and Hs578t.
| Agent | | MDA-MB-468 | SI MDA-MB-468 vs MCF-10A | MDA-MB-231 | SI MDA-MB-231 vs MCF-10A | Hs578t | SI Hs578t vs MCF-10A |
|---|---|---|---|---|---|---|---|
| 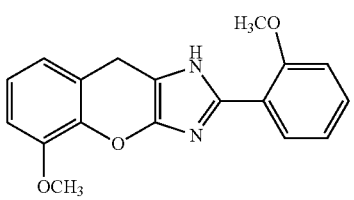 | MC411 | — | — | 1.78 | 2.8 | 8.61 | −0.2 |
| 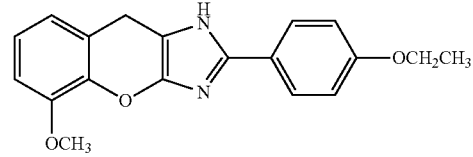 [SMILES: CCOc1ccc(-c2nc3c([nH]2)Cc2cccc(OC)c2O3)cc1] | MC415 | — | — | 1.42 | 0.3 | 0.58 | 2.3 |
| 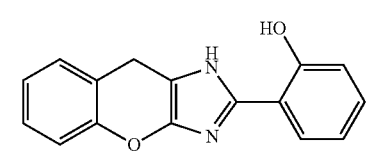 [SMILES: Oc1ccccc1-c1nc2c([nH]1)Cc1ccccc1O2] | M1159 | — | — | 10.4 | >0.6 | — | — |
| 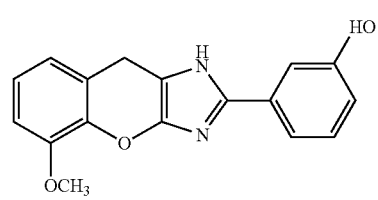 [SMILES: COc1cccc2c1Oc1nc(-c3cccc(O)c3)[nH]c1C2] | MC359 | — | — | 2.70 | 1.5 | 3.48 | 0.9 |
| 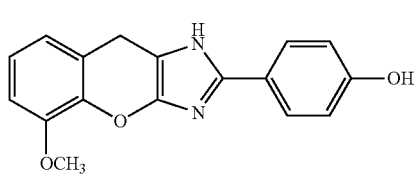 [SMILES: COc1cccc2c1Oc1nc(-c3ccc(O)cc3)[nH]c1C2] | MC413 | — | — | 0.63 | >30 | 0.99 | >19 |
| 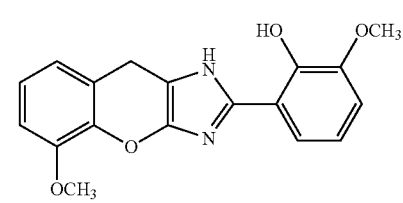 [SMILES: COc1cccc(-c2nc3c([nH]2)Cc2cccc(OC)c2O3)c1O] | M955 | — | — | 15.7 | >0.5 | >20 | — |
| 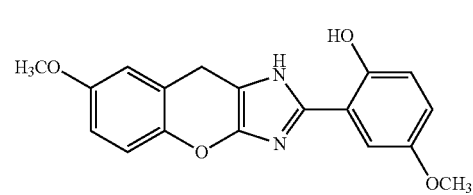 [SMILES: COc1ccc2c(c1)Cc1[nH]c(-c3cc(OC)ccc3O)nc1O2] | M1220 | — | — | — | — | >30 | — |

TABLE 3-continued

IC$_{50}$ values (μM) and selectivity index (SI) of selected chromene-based compounds for TNBC cell lines MDA-MB-468, MDA-MB-231 and Hs578t.

| Agent | | MDA-MB-468 | SI MDA-MB-468 vs MCF-10A | MDA-MB-231 | SI MDA-MB-231 vs MCF-10A | Hs578t | SI Hs578t vs MCF-10A |
|---|---|---|---|---|---|---|---|
| (structure: 7-Cl chromene-benzimidazole with 2-hydroxy-5-chlorophenyl) | M1143 | — | — | >30 | — | >30 | — |
| (structure: 7-Br chromene-benzimidazole with 2-hydroxy-5-bromophenyl) | M1221 | — | — | >30 | — | — | — |

The chromene-based compounds presented very low IC$_{50}$ values for Hs578t, from 0.035 to 0.27 μM. The bromine substituted chromene-based compound MC408 and the dimeric compound MC421 presented very low IC$_{50}$ value for Hs578t cell line and for MDA-MB 468 cell line. The compound MC408 is especially active (IC$_{50}$=0.027 μM). In general, compounds presented an even more interesting antiproliferative potential for these aggressive subtypes of breast cancer and the SI values were also excellent.

In an embodiment, the antiproliferative activity of compounds MC408, MC409, MC421 and MC406 was further determined against glioma cell lines (U87, GAMG and GL18) and acute leukemia cell lines (HL-60, KG-1 and Jurkat). This was done in order to evaluate if the compounds presented an equally interesting anticancer profile in other cancer cell models. Cell viability was determined using the MTS assay, after exposure of the cells to the respective compounds for 72 hours at appropriate concentration ranges to determine the respective IC$_{50}$ values. Table 4 shows the IC$_{50}$ values (μM) for compounds MC408, MC409, MC421 and MC406 for glioma and leukemia cancer cell models.

TABLE 4

IC$_{50}$ values (μM) for compounds MC408, MC409, MC421 and MC406 for glioma and leukemia cancer cell models

| Cell line | Tissue | Compound IC$_{50}$ (μM) | | | |
|---|---|---|---|---|---|
| | | MC409 | MC408 | MC406 | MC421 |
| U87 | Glioma | 0.37 | 1.85 | 0.17 | 0.034 |
| GAMG | Glioma | 0.43 | ND | 0.22 | 0.079 |
| GL18 | Glioma | 0.60 | 1.60 | 0.30 | 0.20 |
| HL-60 | Leukemia | 0.65 | 0.57 | 0.65 | 0.25 |
| KG-1 | Leukemia | 1.02 | 0.64 | 1.01 | 0.93 |
| Jurkat | Leukemia | 0.37 | 0.19 | 0.12 | 0.18 |

The compounds presented excellent antiproliferative capacity, since the determined IC$_{50}$ values for all the cell lines was at the nano-Molar or low micro-Molar range. Compound MC421 presented very high cell growth inhibition for glioma cell lines, especially for U87 and GAMG. Compound MC408 presented lower antiproliferative capacity when compared to the other compounds, but the IC$_{50}$ values were still in the low μM range. In the leukemia models, all the compounds seem to be more selective for Jurkat cell line, but excellent growth inhibition was also achieved by treatment of the other leukemia cell lines with all the compounds. These results demonstrated that these compounds are promising in several cancer cell models and can be considered as candidates for cancer treatment.

In an embodiment, the antiproliferative activity of the compounds was further determined against renal carcinoma cell lines and non-neoplastic kidney cell line. Table 5 shows the IC$_{50}$ values (μM) and selectivity index (SI) for renal carcinoma cell lines (786-O, Caki-2, A498) and non-neoplastic cell line (HK2). Compounds M955, M1220, M1143 and M1221 did not demonstrate any biological activity in a first screen and IC$_{50}$ determination was not pursued. Several compounds demonstrated high potency and an excellent selectivity index towards renal cell carcinoma (RCC) cell lines.

TABLE 5

IC$_{50}$ values (μM) and selectivity index (SI) for renal carcinoma cell lines (786-O, Caki-2, A498) and non-neoplastic cell line (HK2)

| Agent | IC$_{50}$ | | | | SI | | |
|---|---|---|---|---|---|---|---|
| | 786-O | Caki-2 | A498 | HK2 | HK2 vs 786-O | HK2 vs Caki-2 | HK2 vs A498 |
| MC406 | 0.084 | 0.178 | 1.16 | 0.31 | 2.69 | 0.74 | ns |
| MC421 | 0.077 | 0.431 | 0.34 | 2.49 | 31.33 | 4.78 | 6.36 |
| MC369 | 0.053 | 0.109 | — | 0.83 | 14.57 | 6.57 | — |
| MC409 | 0.495 | 0.359 | 0.56 | 3.49 | 6.04 | 8.70 | 5.23 |
| MC408 | 0.064 | 0.089 | 0.14 | 3.49 | 53.59 | 38.29 | 24.00 |
| MC407 | 0.673 | 0.4326 | 1.36 | 1.03 | 0.54 | 1.39 | ns |
| MC412 | 0.032 | 0.039 | 0.29 | 1.63 | 49.97 | 40.82 | 4.60 |
| MC349 | 0.446 | 0.440 | 1.12 | 2.63 | 4.89 | 4.97 | 1.35 |
| MC350 | 0.513 | 0.394 | 0.83 | 21.5 | 40.91 | 53.57 | 24.85 |

TABLE 5-continued

IC$_{50}$ values (μM) and selectivity index (SI) for renal carcinoma cell lines (786-O, Caki-2, A498) and non-neoplastic cell line (HK2)

| | IC$_{50}$ | | | | SI | | |
|---|---|---|---|---|---|---|---|
| | | | | | HK2 vs | HK2 vs | HK2 vs |
| Agent | 786-O | Caki-2 | A498 | HK2 | 786-O | Caki-2 | A498 |
| MC416 | 3.141 | 2.541 | — | 4.72 | 0.50 | 0.86 | — |
| MC410 | 0.446 | 8.530 | — | 23.09 | 50.78 | 1.71 | — |
| MC411 | 3.734 | 3.961 | — | 4.73 | 0.27 | 0.20 | — |
| MC415 | 0.221 | 0.062 | 0.12 | 5.24 | 22.71 | 83.52 | 43.24 |
| M1159 | 3.039 | — | 13.59 | 5.61 | 0.847 | — | ns |
| MC359 | 3.214 | 2.343 | 2.45 | 5.29 | 0.65 | 1.26 | 1.16 |
| MC413 | 0.728 | 0.381 | 0.96 | 10.26 | 13.09 | 25.92 | 9.70 |

In an embodiment, the antiproliferative activity of compounds MC421, MC409, MC408, MC350, MC416, MC410, MC411, MC415 and MC413 was further determined against drug-resistant renal carcinoma cell lines. Table 6 shows the IC$_{50}$ values (μM) and selectivity index (SI) for rapamycin-resistant A498 and cediranib-resistant Caki-2 cell lines and non-neoplastic cell line (HK2).

TABLE 6

IC$_{50}$ values (μM) and selectivity index (SI) for rapamycin-resistant A498 and cediranib-resistant Caki-2 cell lines and non-neoplastic cell line (HK2).

| | IC$_{50}$ (μM) | | | Selectivity Index (vs HK2) | |
|---|---|---|---|---|---|
| Compounds | A498 Resistant | Caki-2 Resistant | HK2 | A498 Resistant | Caki-2 Resistant |
| MC421 | 0.16 | 0.020 | 2.49 | 14.56 | 123.50 |
| MC409 | 0.51 | 0.330 | 3.49 | 5.84 | 9.56 |
| MC408 | 1.07 | 0.028 | 3.49 | 2.26 | 123.79 |
| MC350 | 1.62 | 0.646 | 21.5 | 12.27 | 32.28 |
| MC416 | n.d. | 1.589 | 4.72 | n.d. | 1.97 |
| MC410 | n.d. | 6.408 | 23.10 | n.d. | 2.60 |
| MC411 | n.d. | 1.620 | 4.73 | n.d. | 1.92 |
| MC415 | 0.58 | 0.080 | 5.24 | 8.03 | 64.5 |
| MC413 | 0.77 | 0.335 | 10.26 | 12.32 | 29.6 |

In an embodiment, the effect of the four selected compounds (MC408, MC409, MC406 and MC421) was further evaluated on cell migration (FIG. 1). MCF-7 cells were treated with the respective IC$_{50}$ and half of the IC$_{50}$ values for 72 hours and the wound-healing assay was performed. Half of the IC$_{50}$ concentration was used for each compound to evaluate concentration-dependent effects. FIG. 1 shows the effect of the chromene-based compounds on MCF-7 cell migration (12, 24, 48, 72 hours of treatment with the respective ½IC$_{50}$ and IC$_{50}$ value for each compound), assessed by the wound-healing assay. Results are presented as mean±SD of at least three independent experiments, *p<0.05; p<0.01; *p<0.001; ****p<0.0001 compared to control (DMSO, 0.5%).

Extensive cell death was observed, under the microscope, for all compounds after just 12 hours of incubation. At 72 hours, the medium was removed from each well before the picture was taken as the extensive amount of dead floating cells hindered the exact measurement of cell migration. Compound MC409 showed an early effect on cell migration; after 12 hours, this compound was able to decrease the percentage of cell migration (relative to control of 0.5% DMSO) by about 40% for IC$_{50}$ and ½IC$_{50}$ value. However, cells seem to recover from the effect of the compound as observed by a slow recovery of cell migration. After 72 hours of treatment, the cell migration was inhibited to about 12% less than the control by the use of IC$_{50}$ concentration. For the other 3 compounds, a lower effect was also observed after 24 hours or 48 hours of treatment. For compounds MC408 and MC406 treatment using IC$_{50}$ and ½IC$_{50}$ concentrations led to similar effects on cell migration and after 72 hours cell migration was 20% less than the control. Compound MC421 showed an effect in a concentration dependent manner. A slight effect on cell migration was noticed over time for both IC$_{50}$ and ½IC$_{50}$ concentrations. A decrease in cell migration was observed only after 72 hours of treatment (13% less than control).

Figure 2:
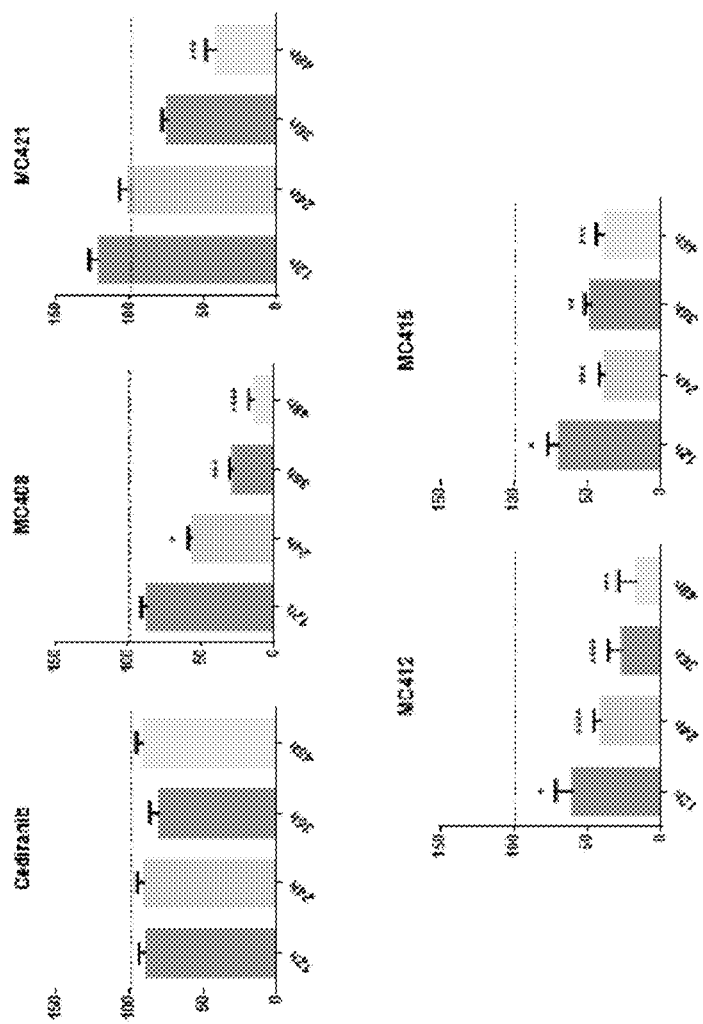
FIG. 2 shows the effect of the chromene-based compounds on Caki-2 cell line migration (12, 24, 36, 48 hours of treatment with the respective $IC_{50}$ value for each compound), assessed by the wound-healing assay.

In an embodiment, the effect of compounds MC408, MC421, MC412 and MC415 was also evaluated for cell migration (FIG. 2) in renal cell carcinoma cell line Caki-2, at 4 different time points. Cediranib was used as reference drug and all the compounds were tested using their respective IC$_{50}$ concentration values. FIG. 2 shows the effect of the chromene-based compounds on Caki-2 cell line migration (12, 24, 36, 48 hours of treatment with the respective IC$_{50}$ value for each compound), assessed by the wound-healing assay. Results were normalized to the control (dashed line) and are presented as mean±SEM. *p<0.05, p<0.005, *p<0.002, ****p<0.0001 compared to control (0.5% DMSO). The significance of the difference between different groups was determined with Student t test.

Figure 3:
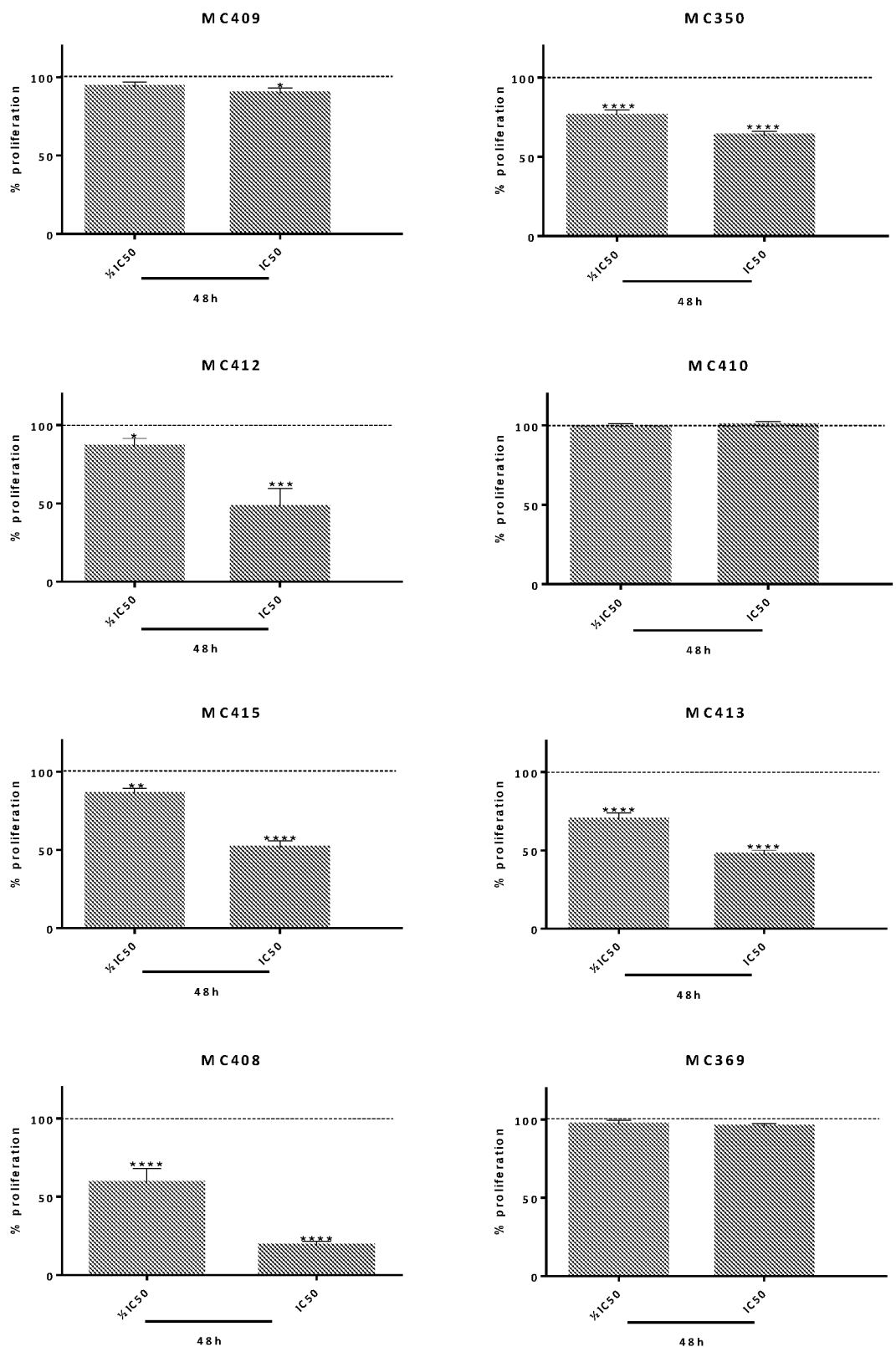
FIG. 3 shows the effect of the chromene-based compounds on 786-0 cell proliferation after 48 hours of treatment.

In an embodiment, the effect of preferred chromene-based compounds on cell proliferation was evaluated. 786-O cells were treated with IC$_{50}$ and ½IC$_{50}$ values, for 48 hours. The ability of BrdU incorporation during DNA synthesis was measured and results are shown in FIG. 3. FIG. 3 shows the effect of the chromene-based compounds on 786-O cell proliferation after 48 hours of treatment. Results are presented as mean±SD at least three independent experiments. *p<0.05, p<0.01, *p<0.0005, ****p<0.0001 compared to control (0.5% DMSO). The significance of the difference between different groups was determined with Student t test. In general, chromenes induced a significant decrease in cell proliferation in a concentration dependent manner, for 786-O cells. Exceptions are observed for compounds MC409, MC410 and MC368.

In an embodiment, the compounds showed a clear effect on cell growth and cell death, especially compounds MC406, MC409 and MC408. This is visible through morphological changes (cells observed under the microscope) and also visible through the presence of round floating cells.

Figure 9:
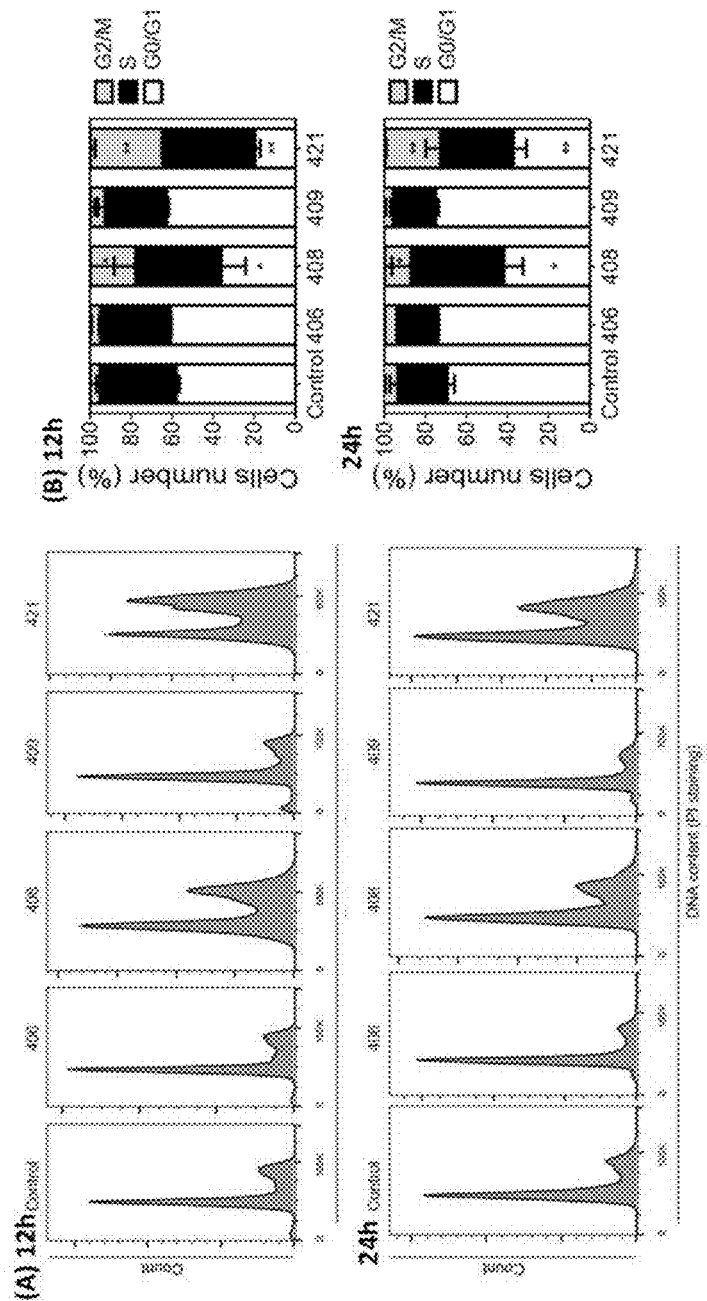
FIG. 9 shows the flow cytometry analysis of the DNA content of Hs578t cells.
Figure 10:
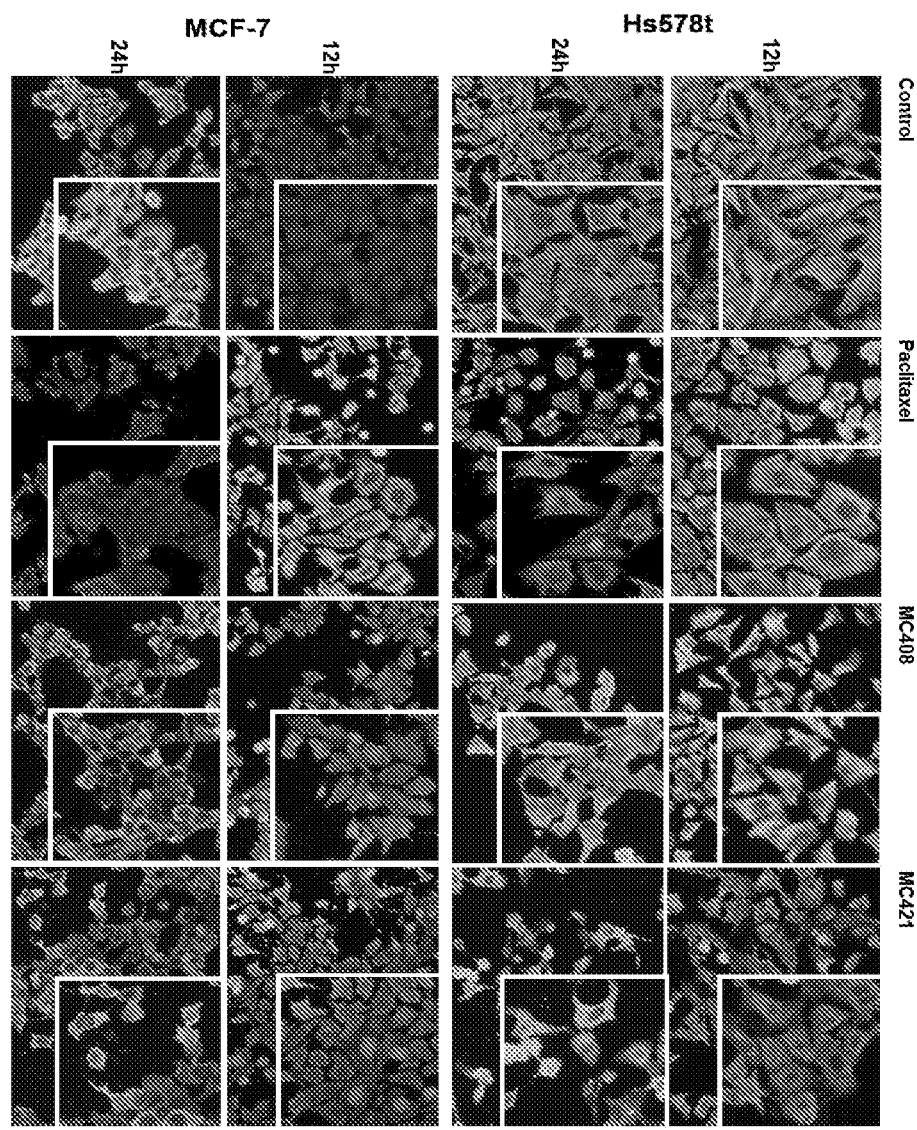
FIG. 10 shows the effect of compounds MC408 and MC421 on the microtubule network of Hs578t (A, B) and MCF-7 (C, D) cells.

In an embodiment, to understand the mechanisms leading to cell death, cells were studied for the induction of apoptosis by flow cytometry. MCF-7 and Hs578t cells were incubated for 12 hours and 24 hours, and 786-O cells were incubated for 24 hours and 48 hours with the respective IC$_{50}$ concentration of the compounds and then double stained with annexin V and propidium iodide (PI) to detect externalization of phosphatidylserine. Externalization of phosphatidylserine occurs during the early apoptotic events. While annexin V binds to phosphatidylserine, PI stains only cells that have lost their membrane integrity, an experimental procedure which allows the discrimination between viable cells, early apoptotic cells, late apoptotic/necrotic cells or necrotic cells. Compounds MC408 and MC421 demonstrated a relevant anticancer effect by inducing cell death by apoptosis (early apoptosis) in the three cell lines at 24 h as shown in FIGS. 9 and 10. Compound MC406 and MC409 also induced cell death by apoptosis in Hs578t cell line.

Figure 4:
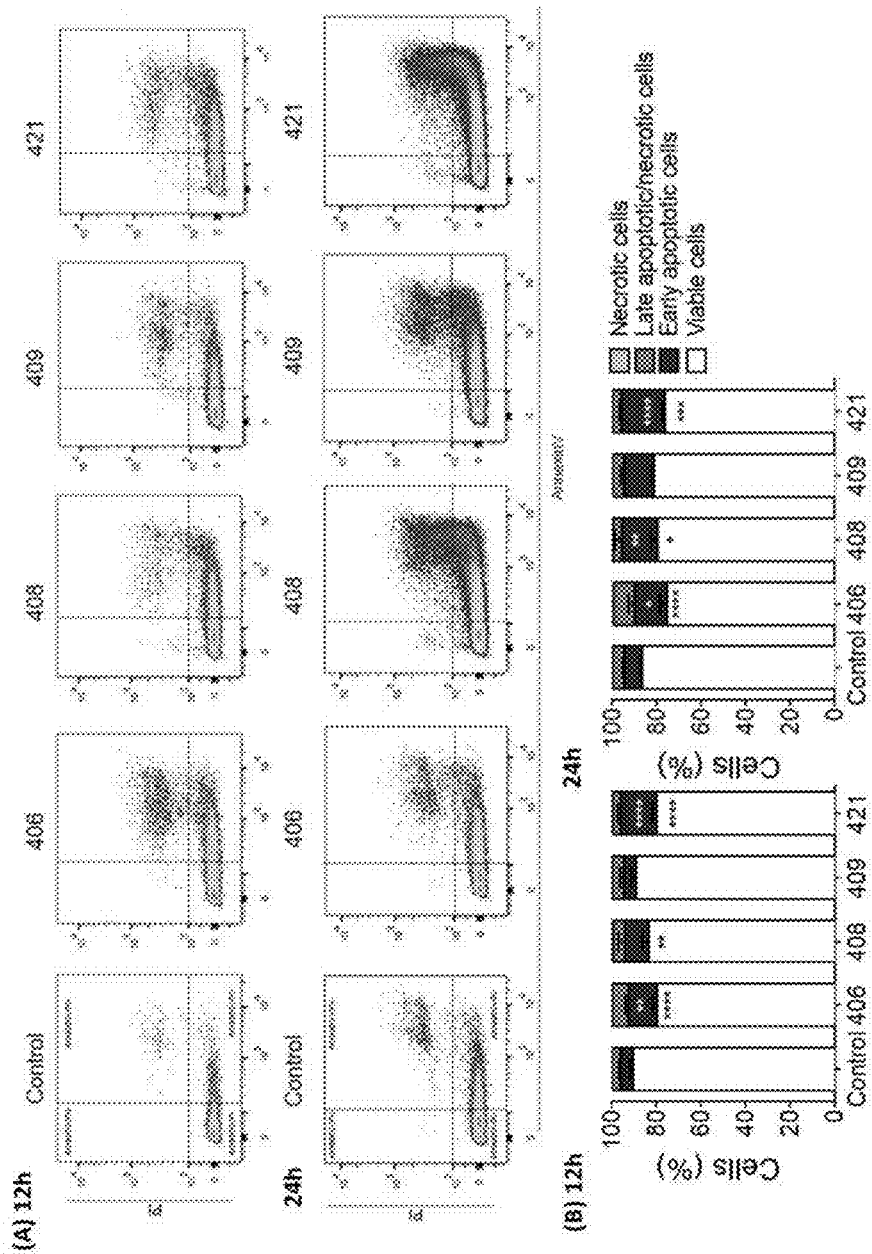
FIG. 4 shows the Flow cytometry analysis of MCF-7 cell viability assessed by annexin V/PI assay.
Figure 5:
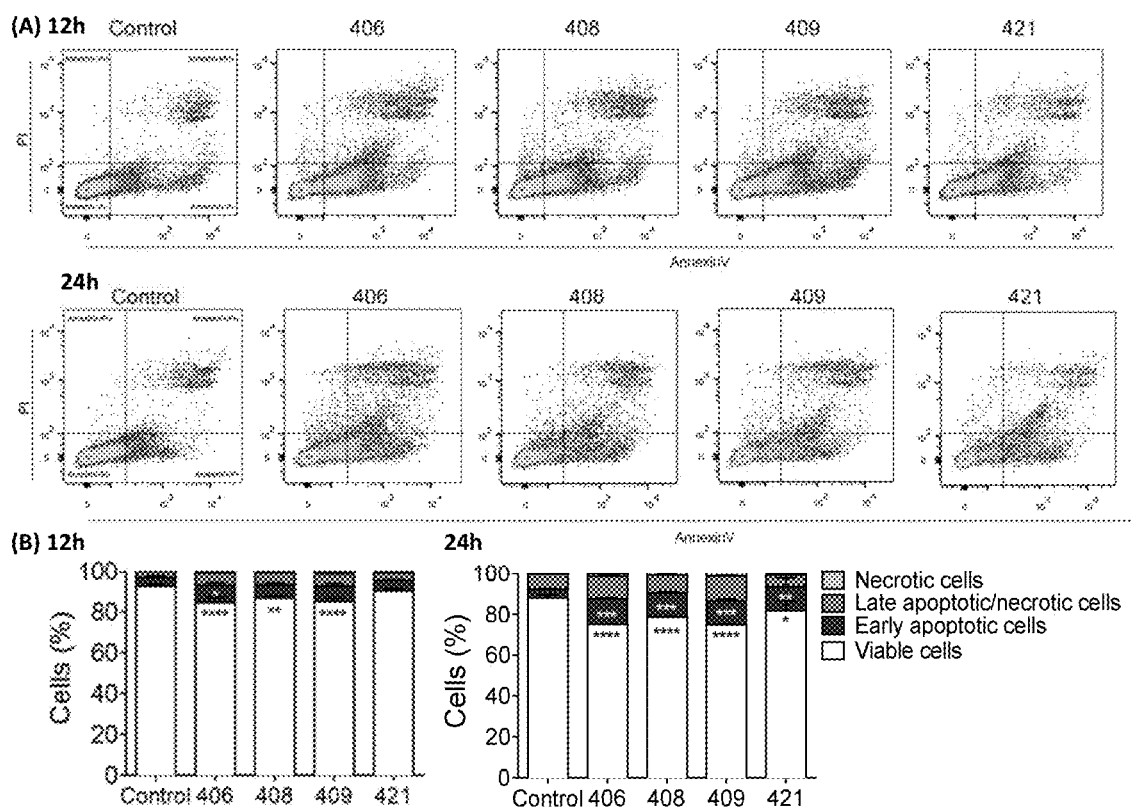
FIG. 5 shows the Flow cytometry analysis of Hs578t cell viability assessed by annexin V/PI assay.
Figure 18:
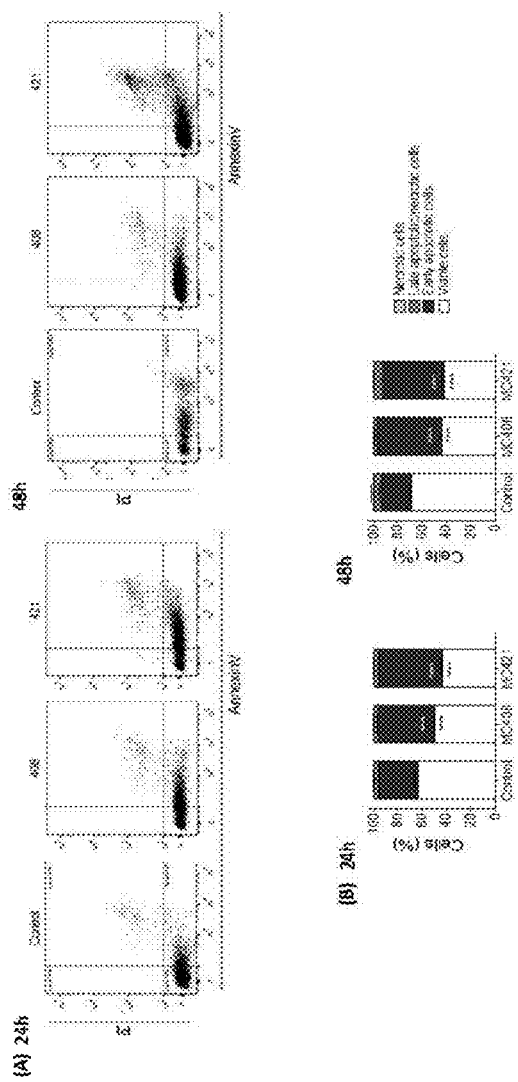
FIG. 18 shows the Flow cytometry analysis of 786-O cell viability assessed by annexin V/PI assay.

FIG. 4 shows the flow cytometry analysis of MCF-7 cell viability assessed by annexin V/PI assay. FIG. 4A shows representative dot plots of MCF-7 cells treated with 0.5% DMSO (control) or treated for 12 hours and 24 hours with $IC_{50}$ concentrations of the compounds MC408, MC409, MC406 and MC421. FIG. 4B shows the quantification of the percentage of cells in each quadrant of the dot plots. The results were obtained using the cells treated with DMSO as control (100%) and mean±SEM of three independent experiments. Annexin V/PI data was analysed by two-way ANOVA and Bonferroni post-hoc test. *p<0.05; p<0.01; *p<0.001; **p<0.0001 compared to control (0.5% DMSO). FIG. 5 shows the flow cytometry analysis of Hs578t cell viability assessed by annexin V/PI assay. FIG. 5A shows representative dot plots of Hs578t cells treated with 0.5% DMSO (control) or treated for 12 hours and 24 hours with $IC_{50}$ concentrations of the compounds MC408, MC409, MC406 and MC421. FIG. 5**B shows the quantification of the percentage of cells in each quadrant of the dot plots. The results were obtained using the cells treated with DMSO as control (100%) and mean±SEM of three independent experiments. Annexin V/PI data was analysed by two-way ANOVA and Bonferroni post-hoc test. *p<0.05; p<0.01; *p<0.001; **p<0.0001 compared to control (0.5% DMSO). FIG. 18 shows the flow cytometry analysis of 786-O cell viability assessed by annexin V/PI assay. FIG. 18A shows representative dot plots of 786-O cells treated with 0.5% DMSO (control) or treated for 24 hours and 48 hours with $IC_{50}$ concentrations of the compounds MC408 and MC421. FIG. 18**B shows the quantification of the percentage of cells in each quadrant of the dot plots. The results were obtained using the cells treated with 0.5% DMSO as control (100%) and mean±SEM of three independent experiments. Annexin V/PI data was analysed by two-way ANOVA and Bonferroni post-hoc test. *p<0.05; p<0.01; *p<0.001; ****p<0.0001 compared to control (0.5% DMSO).

Figure 6:
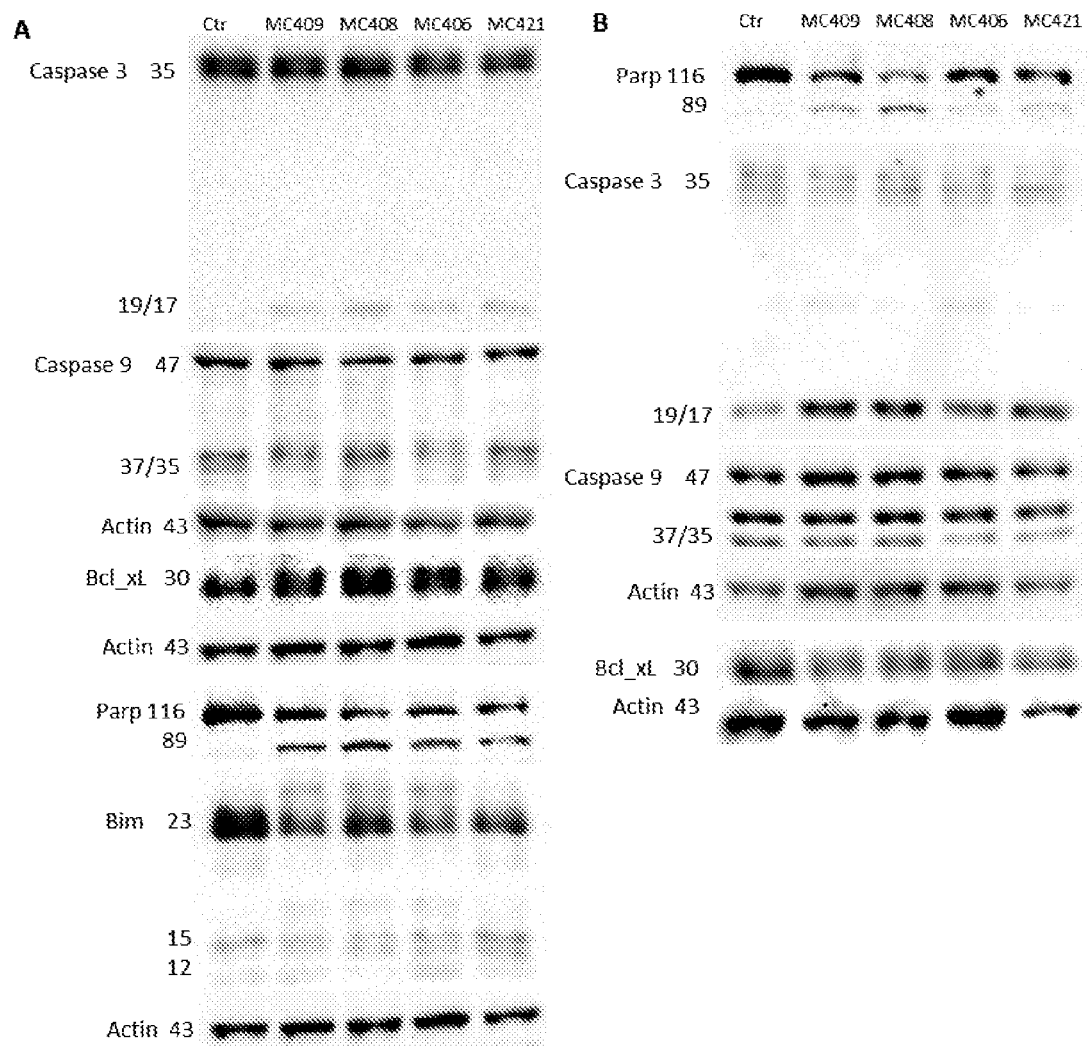
FIG. 6 shows the Western blot analysis for total PARP, Caspase 3 and 9, BIM and Bcl-xL, after treatment of MCF-7 cells for (A) 24 hours and (B) 48 hours with compounds MC409, MC408, MC406 and MC421, using the corresponding $IC_{50}$ concentration. Detection of protein levels by Western blotting in the lysates, using 12% polyacrylamide gel.

In an embodiment, the induction of cell death was further investigated through the examination of apoptotic pathways by Western blot analysis of key apoptosis markers. Poly (ADP-ribose) polymerase 1 (Parp), Caspase 3 and 9 were evaluated as markers for induced apoptosis after cells were treated for 24 and 48 hours with the compounds using $IC_{50}$ (FIG. 6).

Figure 7:
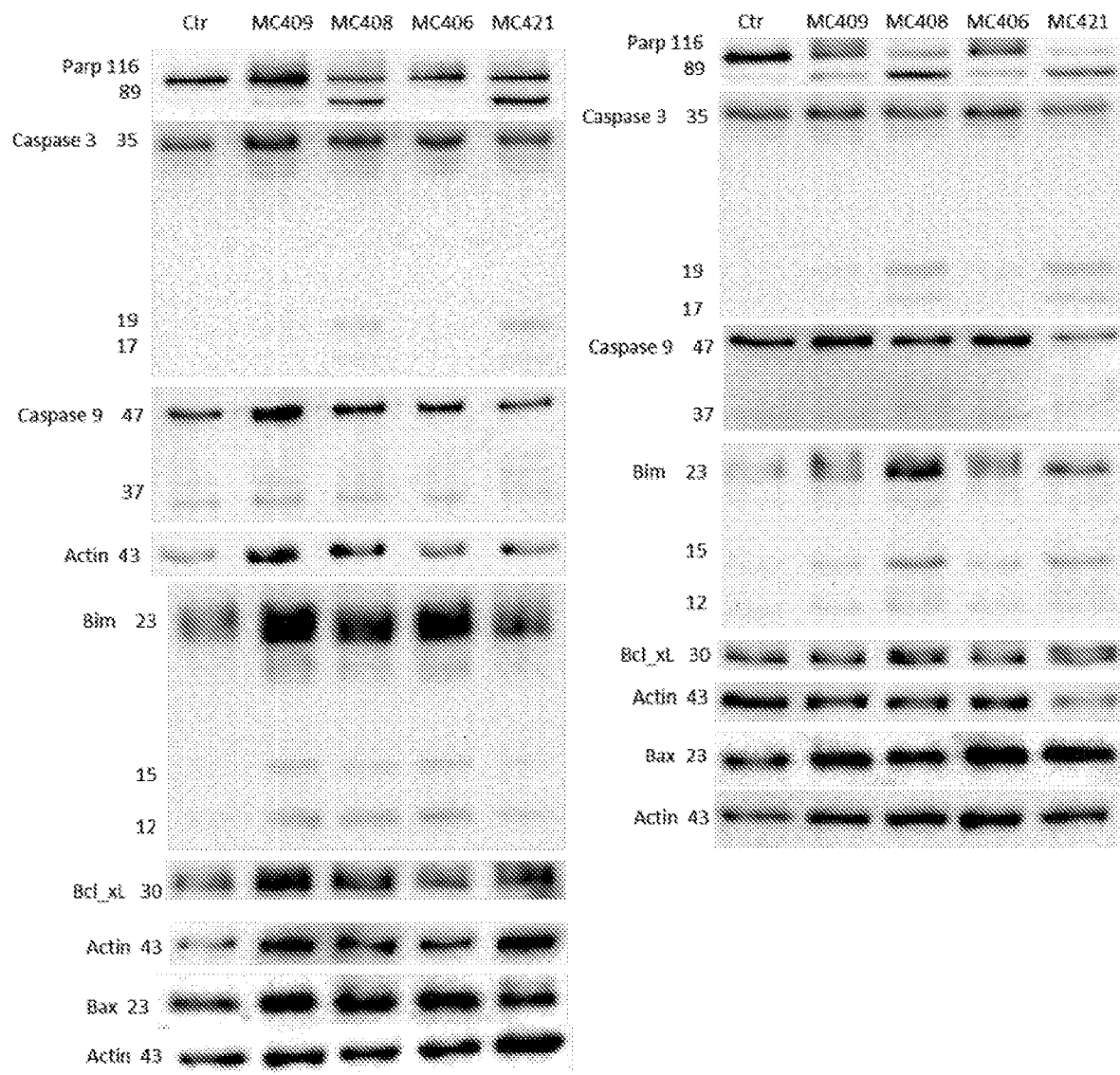
FIG. 7 shows the Western blot analysis for total PARP, Caspase 3 and 9, BIM, Bcl-xL and Bax, after treatment of Hs578t cells for (A) 24 hours and (B) 48 hours with compounds MC409, MC408, MC406 and MC421, using the corresponding $IC_{50}$ concentration. Detection of protein levels by Western blotting in the lysates, using 12% polyacrylamide gel.

Treatment of the cells with the compounds led to cleavage of PARP (FIGS. 6 and 7), a final step of caspase activation and considered to be a hallmark of apoptosis. Cleaved caspase 3 was also observed at the two timepoints. Apoptosis is induced by all the compounds as observed through the presence of these markers.

Bim protein was also used and increased levels were noted for the tested compounds, but only for Hs578t cell line. BH3-domain proteins as Bim, interact with tubulin and in an initial phase, microtubules are described to sequester Bim by binding to the dynein light chain, preventing in this way initiation of apoptotic signalling pathway. Bim migrates to the mitochondria after release from the microtubules, interacting with several proteins (e.g. Bax, Bcl-2 and Bcl-xL) and, finally, promoting apoptosis. This suggests that an early apoptosis signal is released from cells treated with the tested compounds, thus affecting the levels of pro- and anti-apoptotic proteins involved in mitochondrial-induced apoptosis.

Figure 8:
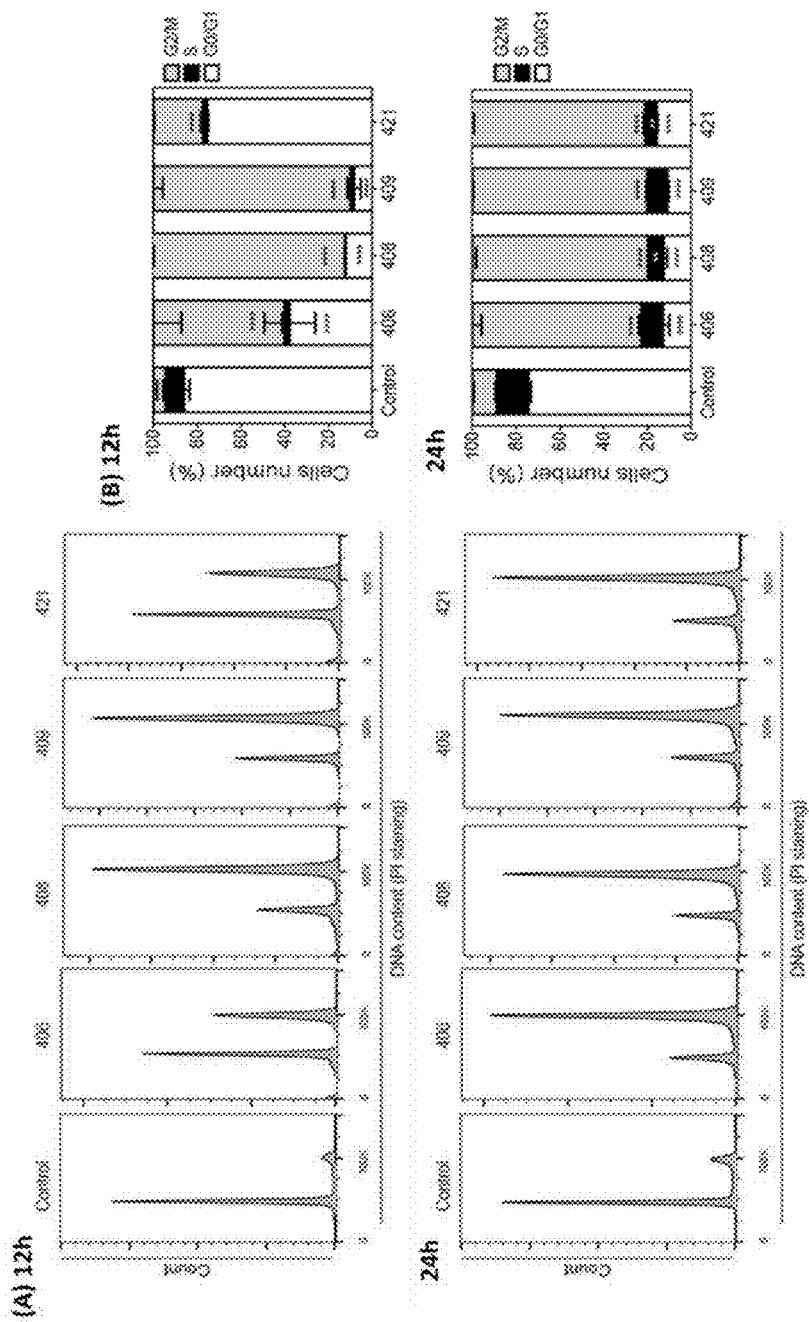
FIG. 8 shows the flow cytometry analysis of the DNA content of MCF-7 cells.
Figure 22:
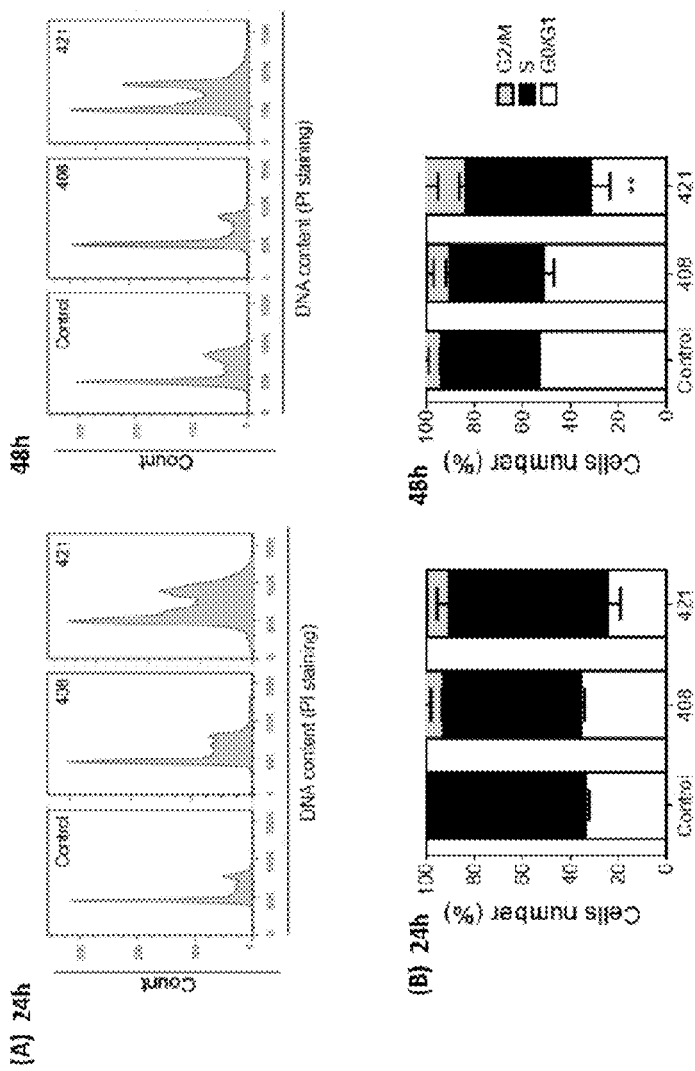
FIG. 22 shows the flow cytometry analysis of the DNA content of 786-O cells.

In an embodiment, cell cycle analysis was performed to determine the ability of the compounds MC408, MC409, MC406 and MC421 to inhibit cell proliferation. MCF-7 and Hs578t cells were treated with the compounds for 12 hours and 24 hours at the respective $IC_{50}$ concentrations. 786-O cells were treated with compounds MC408 and MC421 for 24 hours and 48 hours at the respective $IC_{50}$. Cell cycle analysis was evaluated by DNA content using flow cytometry (FIGS. 8, 9 and 22). FIG. 8 shows the flow cytometry analysis of the DNA content of MCF-7 cells. FIG. 8A shows representative histograms with cell cycle profile of MCF-7 cells treated with 0.5% DMSO (control) or treated for 12 and 24 hours with the $IC_{50}$ concentrations for MC408, MC409, MC406 and MC421. FIG. 8B shows the quantification of the cells in different phases of the cell cycle, except for compound MC409. Results are presented as mean±SD of three independent experiments. Data was analysed by two-way ANOVA and Bonferroni post hoc test. *p<0.05; p<0.01; *p<0.001; ****p<0.0001 compared to control (0.5% DMSO).

FIG. 9 shows the flow cytometry analysis of the DNA content of Hs578t cells. FIG. 9A shows representative histograms with cell cycle profile of Hs578t cells treated with 0.5% DMSO (control) or treated for 12 and 24 hours with the $IC_{50}$ concentrations for MC408, MC409, MC406 and MC421. FIG. 9B shows the quantification of the cells in different phases of the cell cycle, except for compound MC409. Results are presented as mean±SD of three independent experiments. Data was analysed by two-way ANOVA and Bonferroni post hoc test. *p<0.05; p<0.01; *p<0.001; ****p<0.0001 compared to control (0.5% DMSO).

FIG. 22 shows the flow cytometry analysis of the DNA content of 786-O cells. FIG. 22A shows representative histograms with cell cycle profile of 786-O cells treated with 0.5% DMSO (control) or treated for 24 and 48 hours with the $IC_{50}$ concentrations for MC408 and MC421. FIG. 22B shows the quantification of the cells in different phases of the cell cycle. Results are presented as mean±SD of three independent experiments. Data was analysed by two-way ANOVA and Bonferroni post hoc test. *p<0.05; p<0.01; *p<0.001; ****p<0.0001 compared to control (0.5% DMSO).

In an embodiment, the effects of the chromene-based compounds on microtubule dynamics were analysed. FIG. 10 shows the effect of compounds MC408 and MC421 on the microtubule network of Hs578t (A, B) and MCF-7 (C, D) cells. Untreated (control), paclitaxel (Hs578t 12 h: 0.25 µM, 24 h: 0.01 µM; MCF-7 12/24 h: 1 µM) and cells treated with compounds MC408 and MC421 at the $IC_{50}$, for 12 (A, C) or 24 h (B, D), stained with β-tubulin and counterstained with 4,6-diamidino-2-phenylindole (DAPI). Microtubules and unassembled tubulin are shown in green. DNA stained with DAPI is shown in blue.

Figure 11:
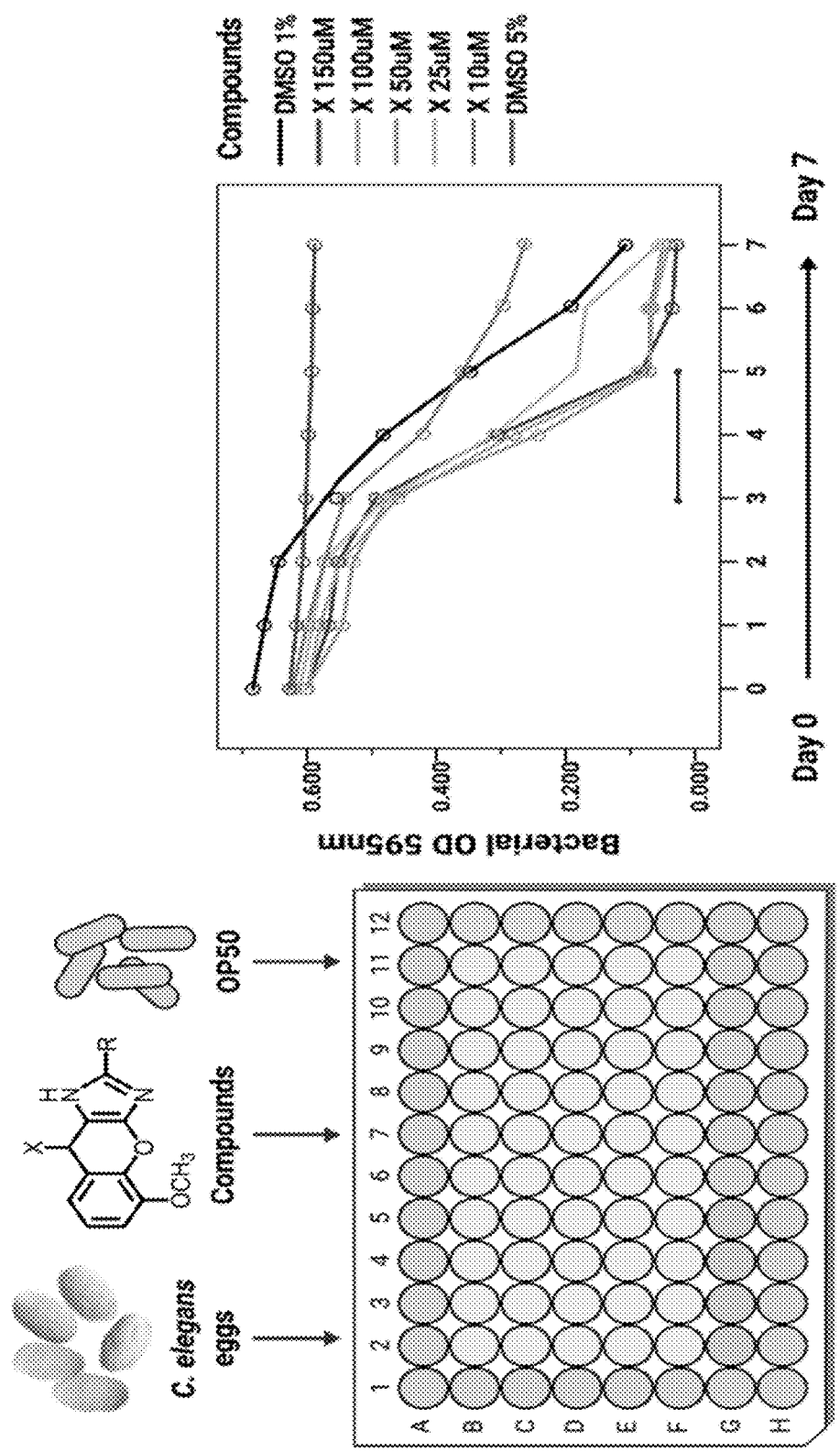
FIG. 11 shows the strategy used in the determination of toxicity effects in C. elegans. Worms were cultivated for 7 days in liquid media using heat-inactivated bacteria (E. coli OP50) as a food source and in the presence of several concentrations of compounds MC421, MC406, MC369 and MC408, MC409, MC407. The rate of food consumption between days 3-5 was used as an indication for worm development, health and also fertility, as after day 3 the worms' progeny will contribute to the faster decline in food abundance as well. An example is shown for hypothetical compound X. DMSO 1% and 5% are used as negative and positive controls for toxicity.

In an embodiment, toxicity assessment of the compounds in vivo was performed using *Caenorhabditis elegans* (*C. elegans*) as a model. A food clearance-based assay was performed, in which the bacteria consumption over time is a proxy for worm development, health and fertility (FIG. 11). FIG. 11 shows the strategy used in the determination of toxicity effects in *C. elegans*. Worms were cultivated for 7 days in liquid media using heat-inactivated bacteria (*E. coli* OP50) as a food source and in the presence of several concentrations of compounds MC421, MC406, MC369 and MC408, MC409, MC407. The rate of food consumption between days 3-5 was used as an indication for worm development, health and also fertility, as after day 3 the worms' progeny will contribute to the faster decline in food abundance. An example is shown for hypothetical compound X. DMSO 1% and 5% are used as negative and positive controls for toxicity, respectively. For this experiment, the compounds were solubilized in DMSO 1% (vehicle).

Figure 12:
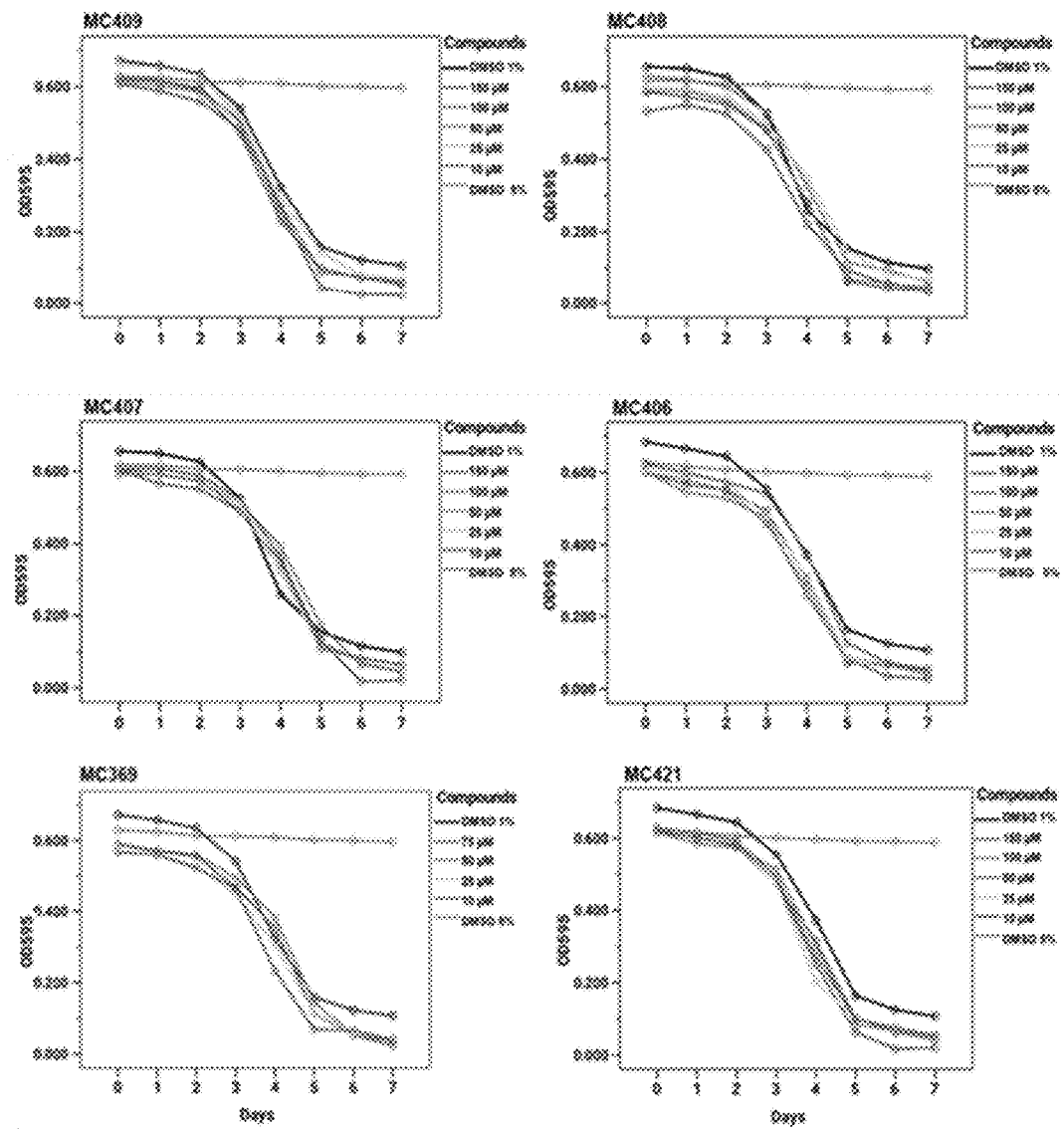
FIG. 12 shows the lack of in vivo toxicity of the compounds in *C. elegans*.

The compounds were tested at several concentrations, up to the highest soluble concentration possible –150 µM (MC369, 75 µM) (FIG. 12). FIG. 12 shows the analysis of the in vivo toxicity of MC421, MC406, MC369 and MC408, MC409, MC407 in *C. elegans*. The rate of food consumption between days 3-5 was used as an indication for worm development, health and fertility and compared to 1% DMSO, (vehicle, not toxic). No statistical differences were observed for MC421, MC406, MC369 and MC408, MC409, MC407 (ANOVA, followed by the Games-Howell post-hoc test). No statistical differences in rate of food consumption for day 3-5 were detected for any of the compounds/ concentrations of the compounds. The fact that the compounds seem to be well tolerated, even at significantly higher concentrations than those used for the in vitro tests, may be a good predictor for toxicity in mammalian models.

Figure 13:
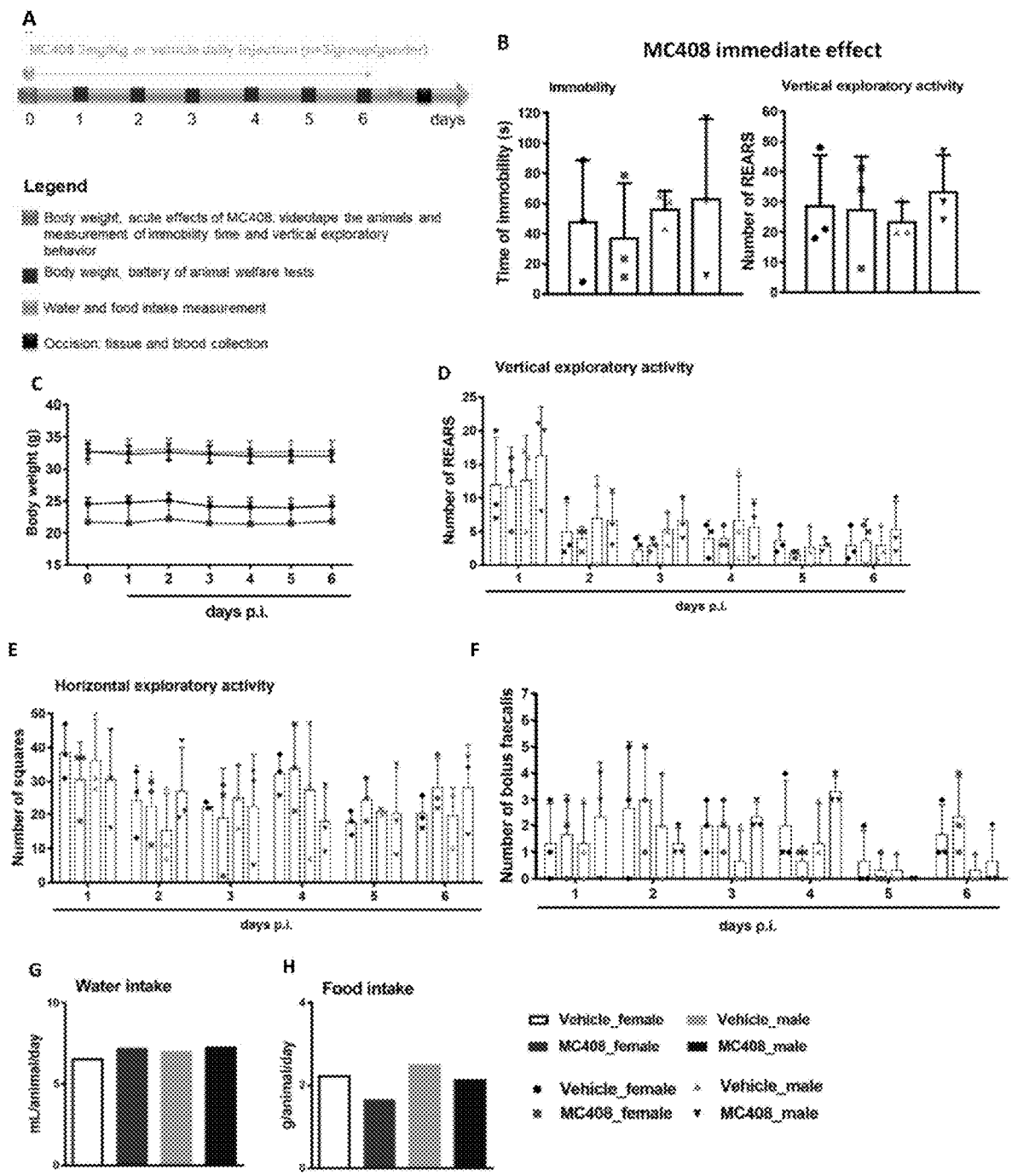
FIG. 13 shows the effects of compound MC408 on C57BI/6 mice.

In an embodiment, the safety profiles of the compounds were evaluated in rodents. FIG. 13 shows the effects of MC408 treatment on C57BI/6 mice—1$^{st}$ trial. FIG. 13A is a schematic representation of the experiment timeline. 5-month old female and male animals were used (n=3/group/gender) and injected either with MC408 3 mg/Kg or vehicle (saline, Tween80 and methylcellulose) (i.p.) daily for 7 days. A battery of welfare tests was performed daily. FIG. 13B shows what happens immediately after the first injection; for this analysis, animals were videotaped for 10 min and immobility time and vertical movement (REARS) were counted by the experimenter. No differences were found between vehicle and MC408 mice. FIG. 13B shows the body weight of the mice which were monitored during the entire experiment and no differences were found between treatment groups. FIG. 13D shows the vertical exploratory activity of the mice. The activity was measured in a viewing jar and the number of vertical movements were counted for 5 minutes. FIG. 13E shows the horizontal activity of the mice. The activity was recorded in an open arena labelled with squares and the number of squares were counted while the animals were freely exploring for 1 minute. No differences were found in exploratory activities. FIG. 13F shows the indirect measure of anxiety in the mice. To indirectly measure anxiety, the number of bolus faecalis the animals produced during the behavioural setup was counted and no differences were observed among groups. In FIGS. 13G and H, water and food intake were analysed respectively. Each day, 0.300 g of food and 200 mL of water were placed in each cage. At the end of the trial (at day 7) food was weighted and water measured and no differences were found in both parameters. Data is presented as mean±SE.

FIG. 14 shows the effects of MC408 treatment on C57BI/6 mice. A battery of welfare tests was performed to evaluate signs of toxicity of the treatment with the MC408 when compared to vehicle animals. All the parameters evaluated were scored as normal or abnormal, present or absent, and all the animals scored equally (MC408 and vehicle), suggesting no impact of the compound on mice welfare.

Figure 15:
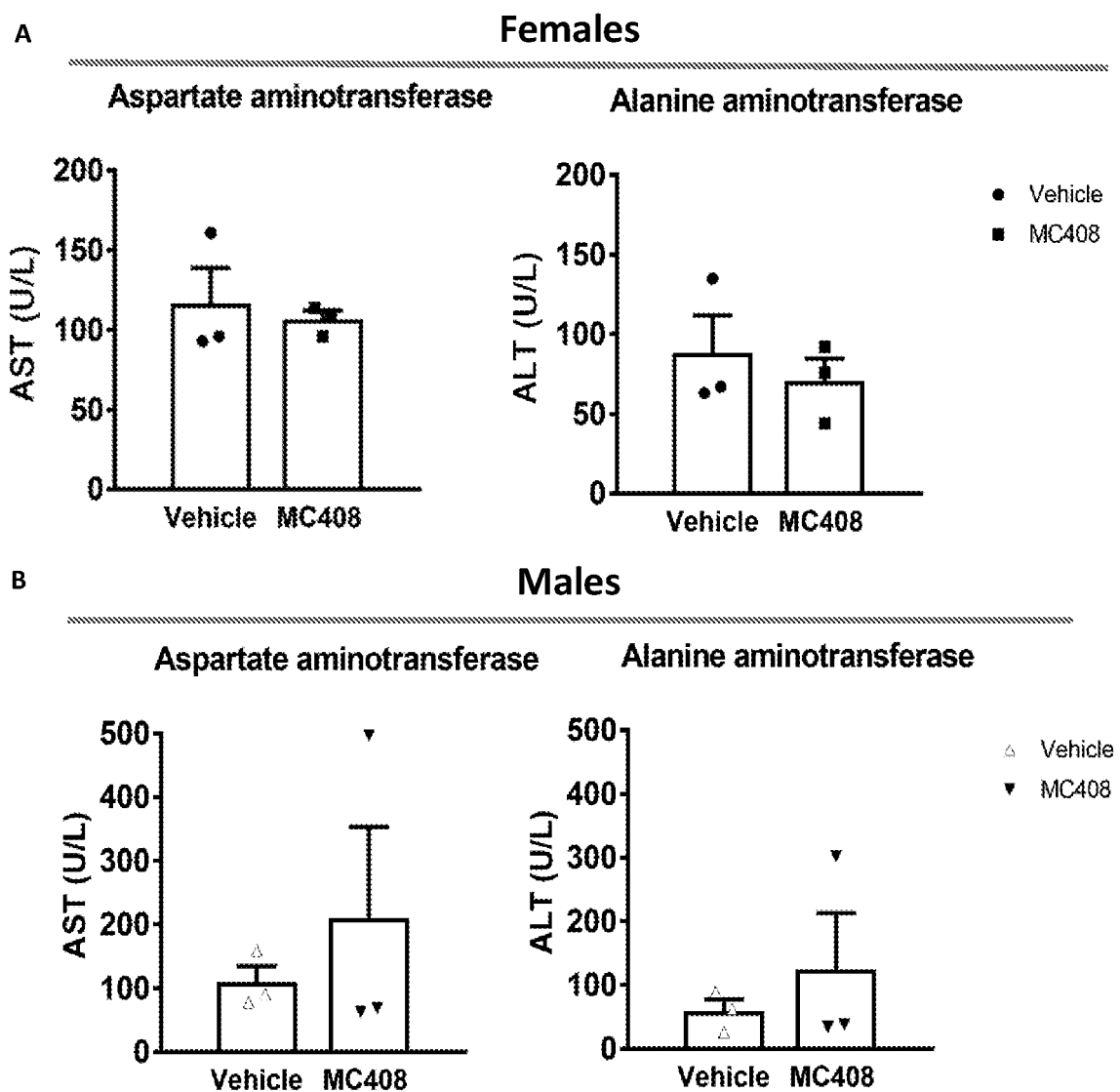
FIG. 15 shows the effects of MC408 treatment on the enzymatic liver function of C57BI/6 mice.

In an embodiment, the effects of treatment on the liver function of C57BI/6 mice were analysed. FIG. 15 shows the effects of MC408 treatment on the enzymatic liver function of C57BI/6 mice. Aspartate aminotransferase (AST/TGO) and alanine aminotransferase (ALT/TGP) were measured in the serum of (FIG. 15A) females and (FIG. 15B) males using standard techniques. The blood was collected at the end of the experiment (day 7). No statistical differences between compound- and vehicle-treated animals were found within each gender. Notably, one male in the MC408 treatment group presented higher levels of both AST and ALT when compared to the other two animals in the same group. Data is presented as mean±SE.

Figure 16:
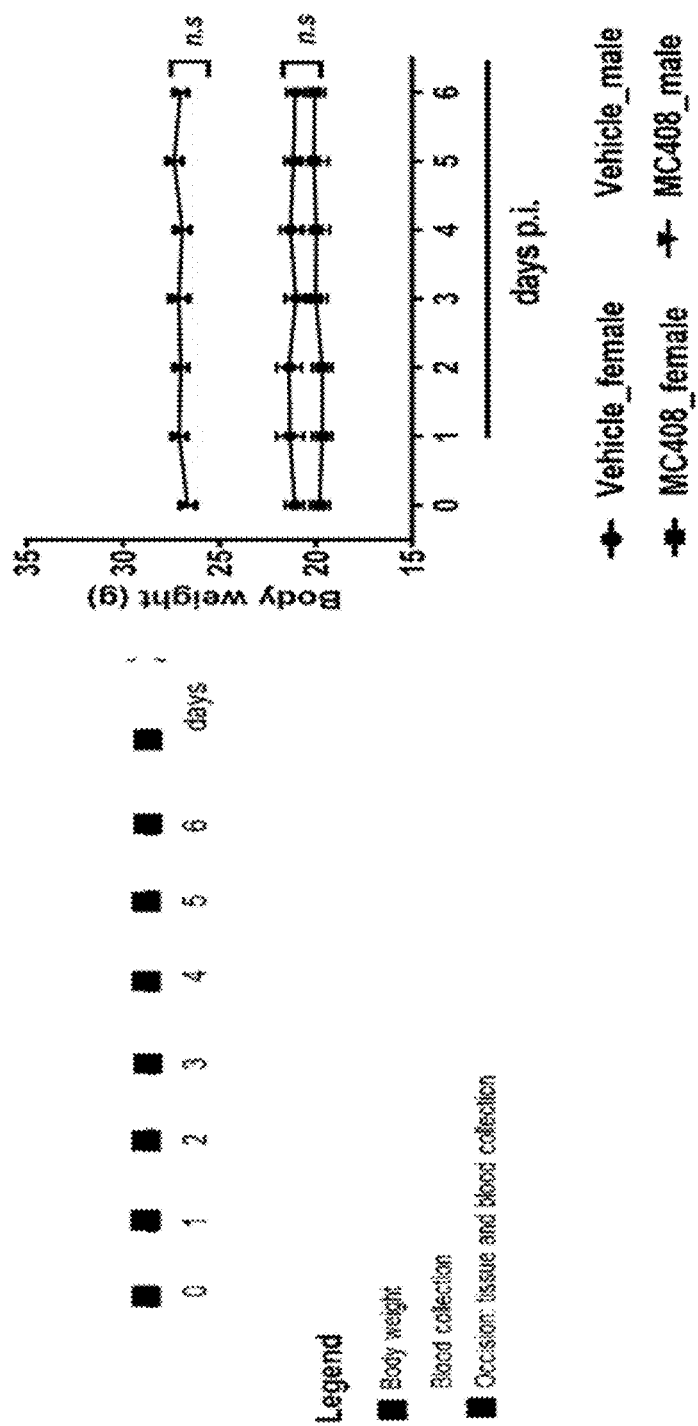
FIG. 16 shows the effects of MC408 treatment on C57BI/6 mice—2nd trial.

In an embodiment, the effects of compound treatment on C57BI/6 mice—2$^{nd}$ trial was analysed. FIG. 16 shows the effects of MC408 treatment on C57BI/6 mice—2$^{nd}$ trial. FIG. 16A is a schematic representation of the experiment timeline. 3-month old female and male animals were used (n=6/group/gender) and injected either with MC408 3 mg/Kg or vehicle (saline, Tween80 and methylcellulose) (i.p.) daily for 7 days. In this trial the number of animals per group was increased and the experiment was conceived to collect blood before and after the treatment. FIG. 16B shows the body weight of the mice. Body weight was monitored during the entire experiment and no differences were found between groups within each gender. Data is presented as mean±SE.

Figure 17:
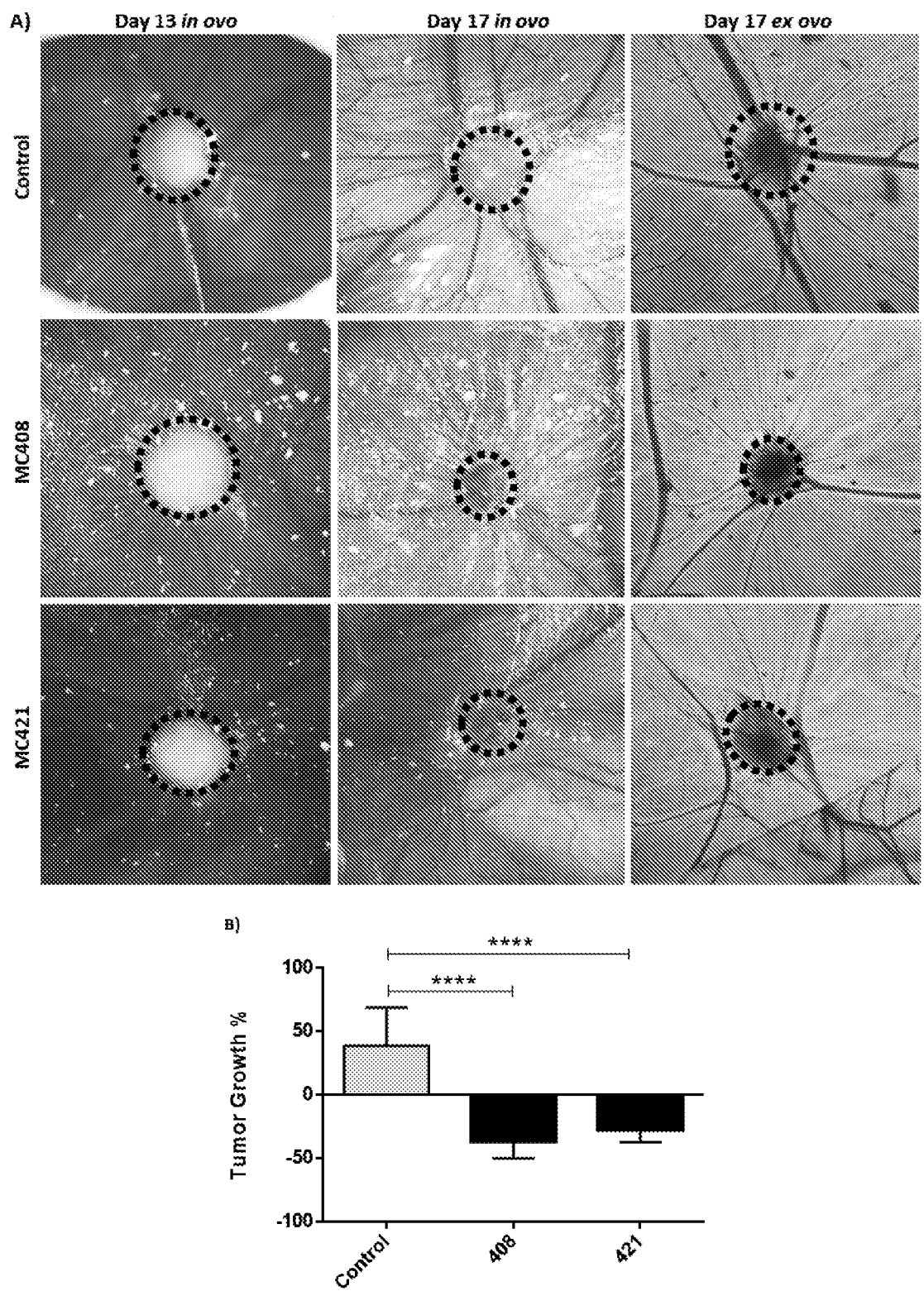
FIG. 17 shows the in vivo therapeutic effect of MC408 and MC421 on Breast cancer Hs578t cell line.

In an embodiment, in vivo therapeutic efficiency study of the compounds was analysed using CAM model. FIG. 17 shows the in vivo therapeutic effect of MC408 and MC421 on breast cancer Hs578t cell line. FIG. 17A shows representative pictures ('10 magnification) of CAM assay in ovo and ex ovo (at days 13 and 17). FIG. 14B shows tumor growth percentages. The results were expressed as mean percentage of tumor growth from day 13 to day 17 of development ±SD. ****p<0.0001. Data was analysed by one-way ANOVA test. Eggs were treated with control (DMSO 0.5%), MC408 (2×IC$_{50}$=0.094 µM) or MC421 (2×IC$_{50}$=0.070 µM).

Figure 19:
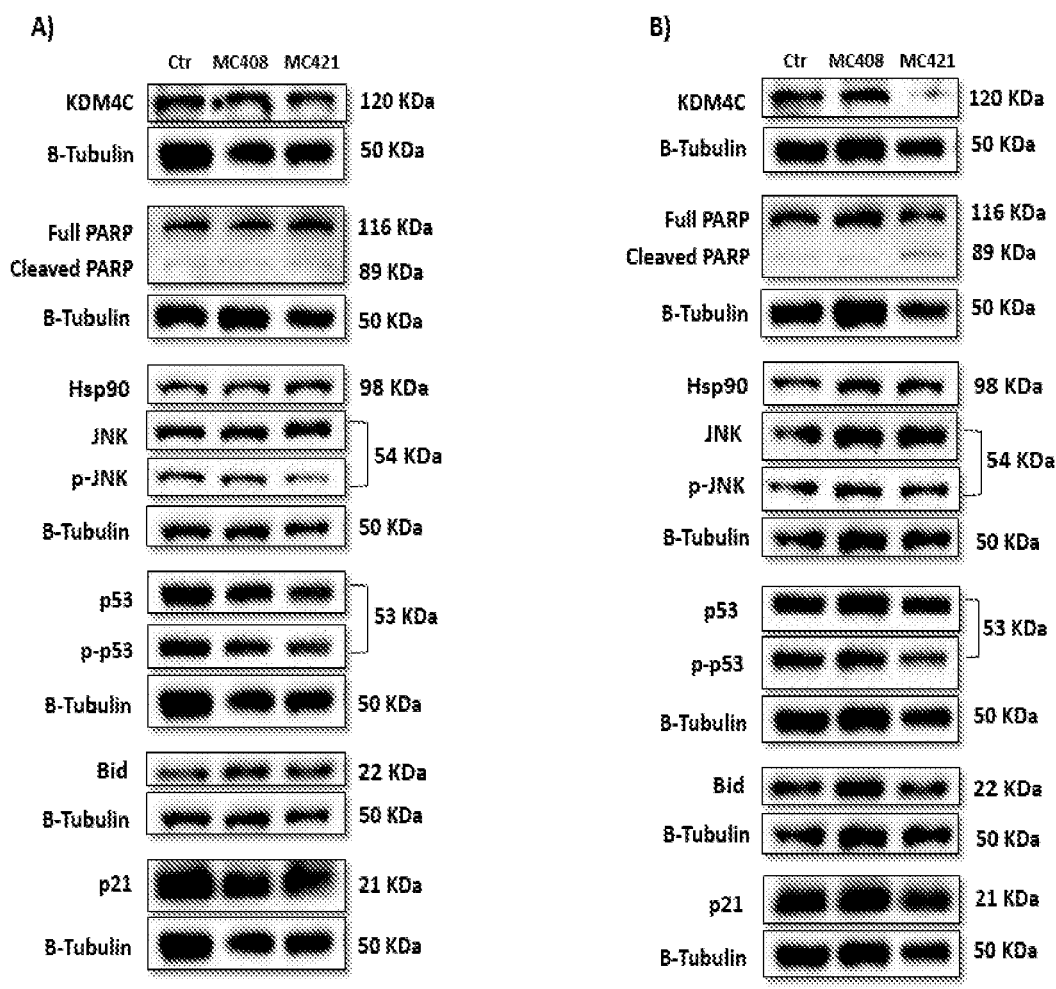
FIG. 19 shows the Western blot analysis for KDM4C, total PARP, Hsp90, total JNK, total p53, Bid and p21, after treatment of 786-O cells for (A) 24 hours and (B) 48 hours with compounds MC408 and MC421, using the corresponding $IC_{50}$ concentration. Detection of protein levels by Western blotting in the lysates, using 12% polyacrylamide gel.

In an embodiment, the induction of cell death was further investigated through the examination of apoptotic pathways by Western blot analysis of key apoptosis markers. Poly (ADP-ribose) polymerase 1 (Parp), heat shock protein 90 (Hsp90), c-Jun N-terminal kinase (JNK), p53, BH3 interacting-domain death agonist (Bid) and p21 were evaluated as markers for induced apoptosis after 786-O cells were treated for 24 and 48 hours with the compounds using IC$_{50}$ (FIG. 19).

Figure 20:
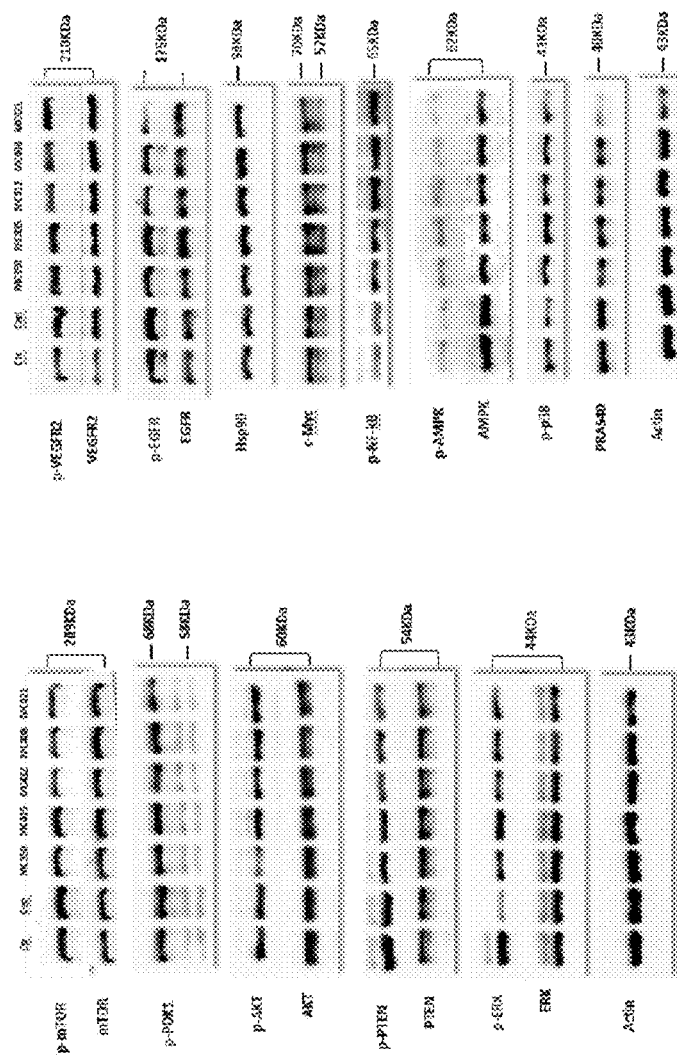
FIG. 20 shows the Western blot analysis for total and phosphorylated forms of mTOR, ERK, VEGFR2, EGFR, AKT, PTEN and AMPK, phosphorylated forms of PDK1, NF-kB and p18, and c-Myc, Hsp90 and PRAS40 proteins after a starvation period of 2 hours and treatment of 786-O cells for 6 hours with Cediranib, compounds MC350, MC415, MC412, MC408 and MC421, using a unique concentration of 2 µM. Detection of protein levels by Western blotting in the lysates, using 10% polyacrylamide gel.

In an embodiment, the interaction with RTK receptors and the mTOR/PI3K/AKT pathway was further investigated through the assessment of mammalian target of rapamycin (mTOR), extracellular-signal-regulated kinase (ERK), vascular endothelial growth factor receptor 2 (VEGFR2), endothelial growth factor receptor (EGFR), Protein kinase B (AKT), phosphatase and tensin homolog (PTEN), 5' adenosine monophosphate-activated protein kinase (AMPK), Pyruvate dehydrogenase kinase 1 (PDK1), factor nuclear kappa B (NF-kB), p18, c-Myc, Hsp90 and proline-rich Akt substrate of 40 kDa (PRAS40) proteins. These markers were assessed after a 6 hour treatment with Cediranib (potent inhibitor of vascular endothelial growth factor used in the treatment of renal cell carcinoma) and the compounds MC350, MC412, MC415, MC408 and MC421 using a unique dose of 2 µM (FIG. 20).

Treatment of 786-O cells with several of the compounds led to decreased levels of phosphorylated-mTOR and AKT protein levels. Moreover, both EGFR and VEGFR2 present decreased levels in some cases when comparing to the control and Cediranib. Several of the tested compounds affect the mTOR/PI3K/AKT pathway, interfering with different protein markers.

VEGFR and EGFR are receptors of tyrosine kinases (RTKs) specific for vascular endothelial (VEGF) and endothelial (EGF) growth factors families with critical roles in tumor growth and metastasis. Their autophosphorylation stimulates downstream activation and signaling by numerous other proteins associated with the phosphorylated tyrosines. These downstream signaling proteins initiate several signal transduction cascades, including Akt pathway, leading to gene expression, cell proliferation and migration, vasculogenesis and angiogenesis. Moreover, mTOR regulates cell growth, proliferation and metabolism. Its activity is controlled by two multiprotein complexes mTORC1, sensitive to rapamycin, and mTORC2, considered to be resistant or only inhibited when given at high doses for prolonged periods of time. Second generation dual mTOR inhibitors have been developed and the most important advantages of those new drugs are the considerable decrease of AKT phosphorylation on mTORC2 blockade and better inhibition on mTORC1. Considering the results, a reduction in RTKs, mTOR and AKT expression suggest a decrease in key regulators for all the functions described above.

Figure 21:
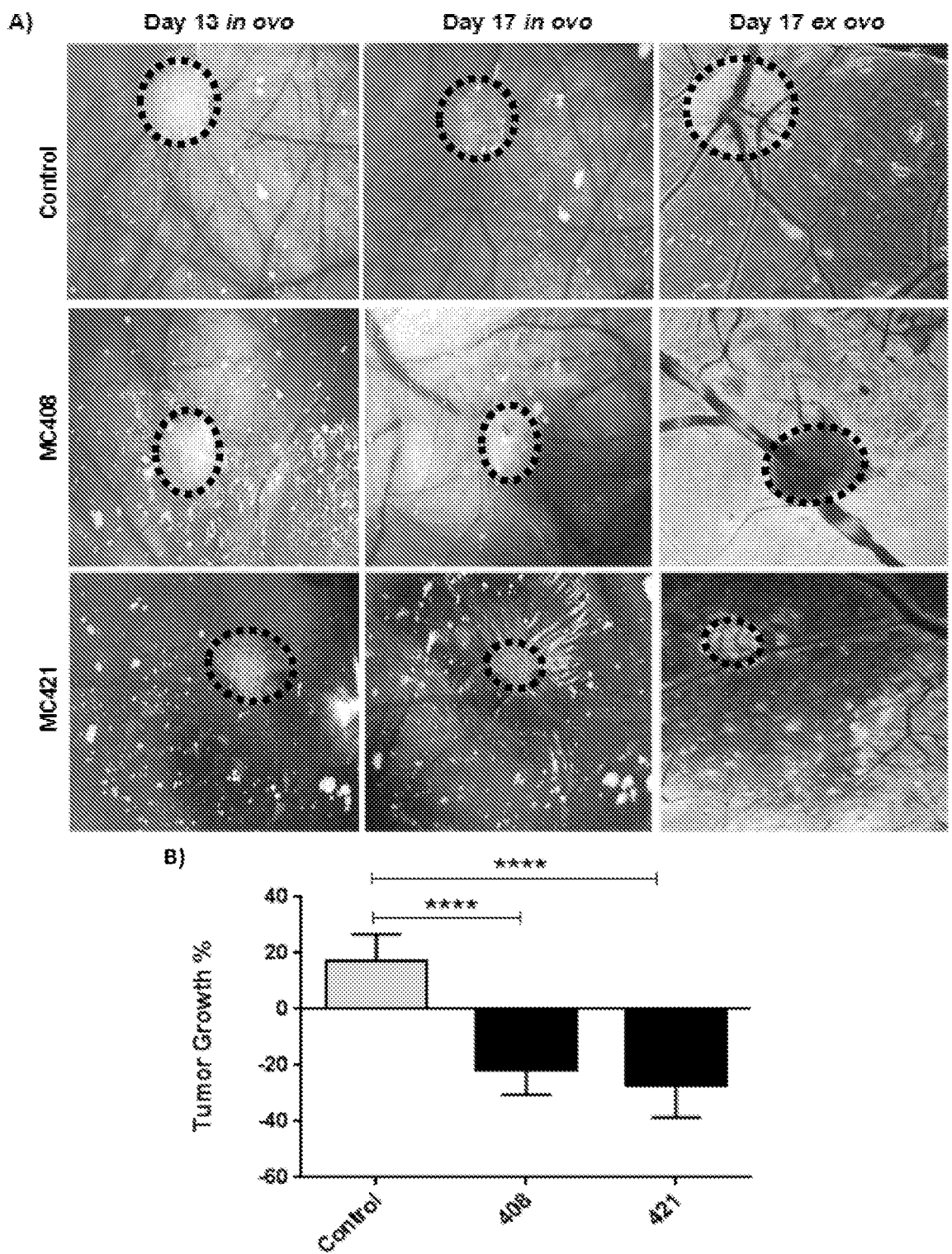
FIG. 21 shows the in vivo therapeutic effect of MC408 and MC421 on Renal cancer 786-O cell line.

In an embodiment, the in vivo therapeutic efficacy of the compounds was analysed using the CAM model. FIG. 21 shows the in vivo therapeutic effect of MC408 and MC421 on renal cancer 786-O cell line. FIG. 21A shows representative pictures (×10 magnification) of CAM assay in ovo and ex ovo (at days 13 and 17). FIG. 21B shows tumor growth percentages. The results were expressed as mean percentage of tumor growth from day 13 to day 17 of development±SD, $p<0.0001$ compared to control (statistical analysis performed using one-way ANOVA test). Eggs were treated with control (DMSO 0.5%), MC408 ($2×IC_{50}=0.128$ μM) or MC421 ($2×IC_{50}=0.154$ μM).

Figure 23:
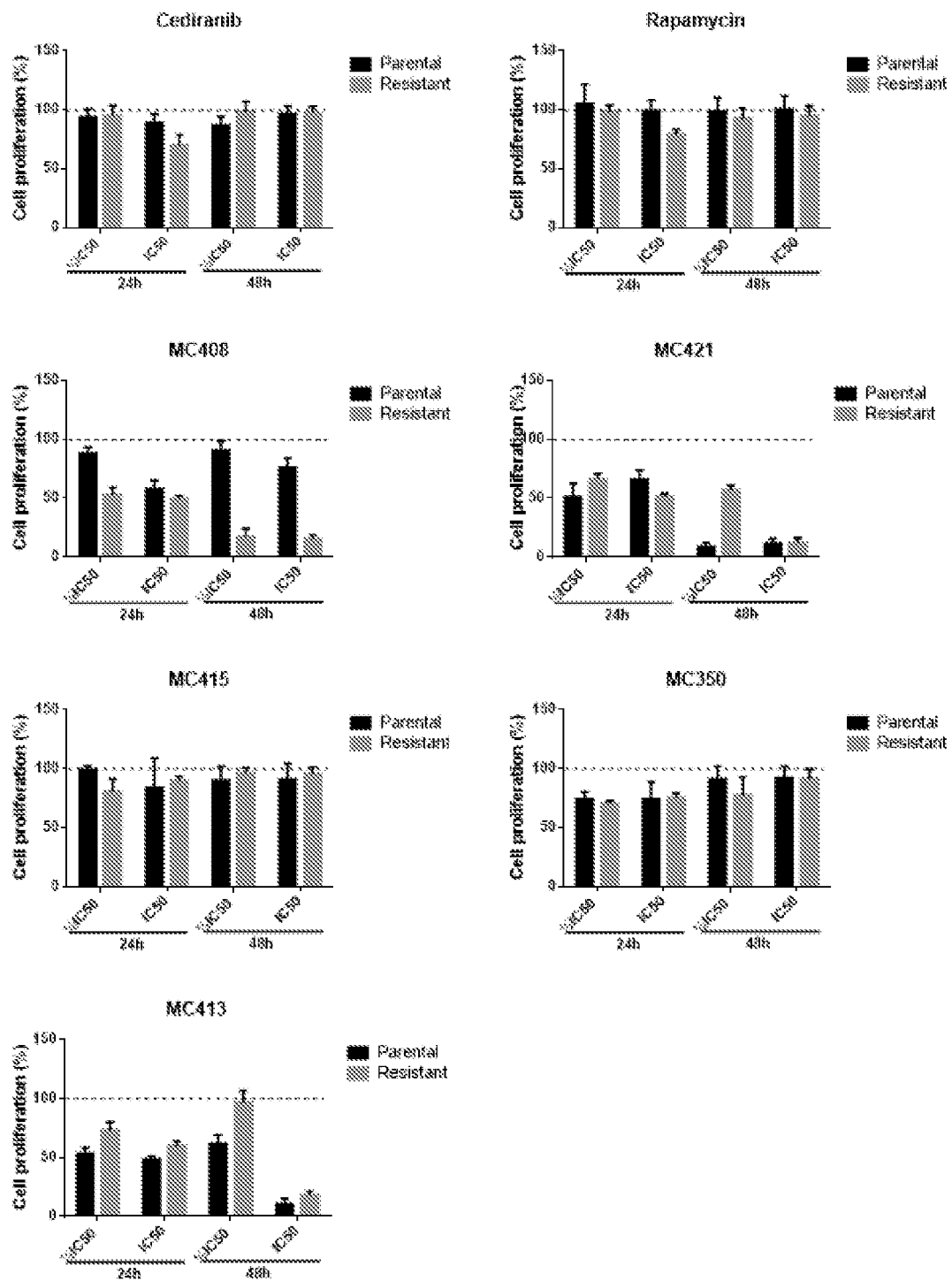
FIG. 23 shows the effect of the chromene-based compounds on cell proliferation for A498 resistant and parental cell line after 24 and 48 hours of treatment with ½ $IC_{50}$ or $IC_{50}$ of the selected compounds.
Figure 24:
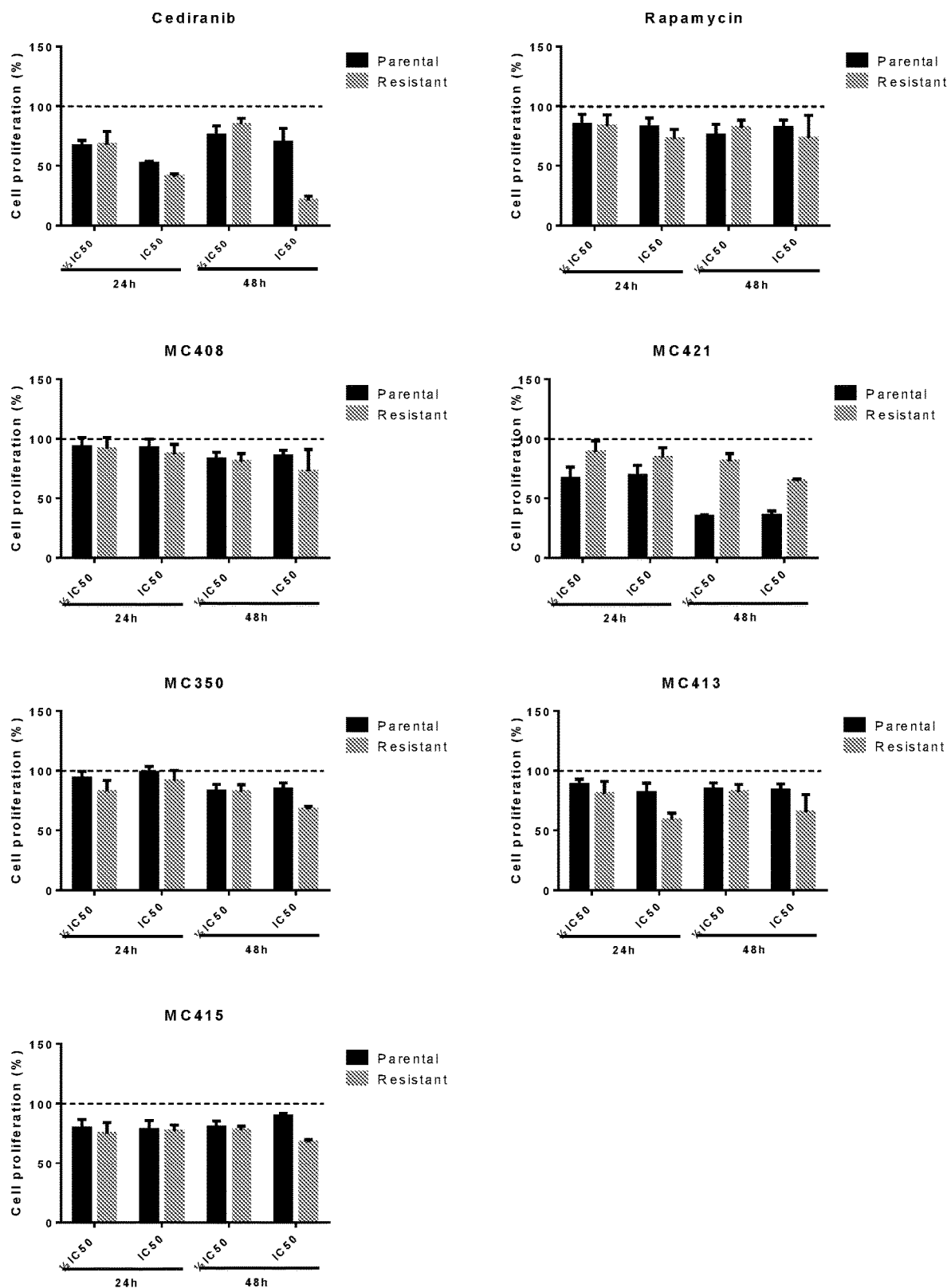
FIG. 24 shows the effect of the chromene-based compounds on cell proliferation for Caki-2 resistant and parental cell line after 24 and 48 hours of treatment with ½ 2 $IC_{50}$ or $IC_{50}$ of selected compounds.

In an embodiment, the effect of cediranib, rapamycin and chromene-based compounds on cell proliferation was evaluated. A498 (parental and rapamycin-resistant) and Caki-2 (parental and cediranib-resistant) cells were treated with $IC_{50}$ and ½$IC_{50}$ values, for 24 and 48 hours. The ability of BrdU incorporation during DNA synthesis was measured and results are shown in FIGS. 23 and 24. FIG. 23 shows the effect of the chromene-based compounds on A498 (parental and rapamycin-resistant) cell proliferation after 24 and 48 hours of treatment. FIG. 24 shows the effect of the chromene-based compounds on Caki-2 (parental and cediranib-resistant) cell proliferation after 24 and 48 hours of treatment. Results are presented as mean±SD of at least three independent experiments.

In general, chromenes induced a significant decrease in cell proliferation in a concentration and time dependent manner, specially compounds MC408, MC421 and MC413, either for parental or resistant A498 cells (FIG. 23).

For parental and drug-resistant Caki-2 cells (FIG. 24), chromenes MC421, MC350 and MC413 were able to decrease cell proliferation in a concentration and time dependent manner.

Figure 25:
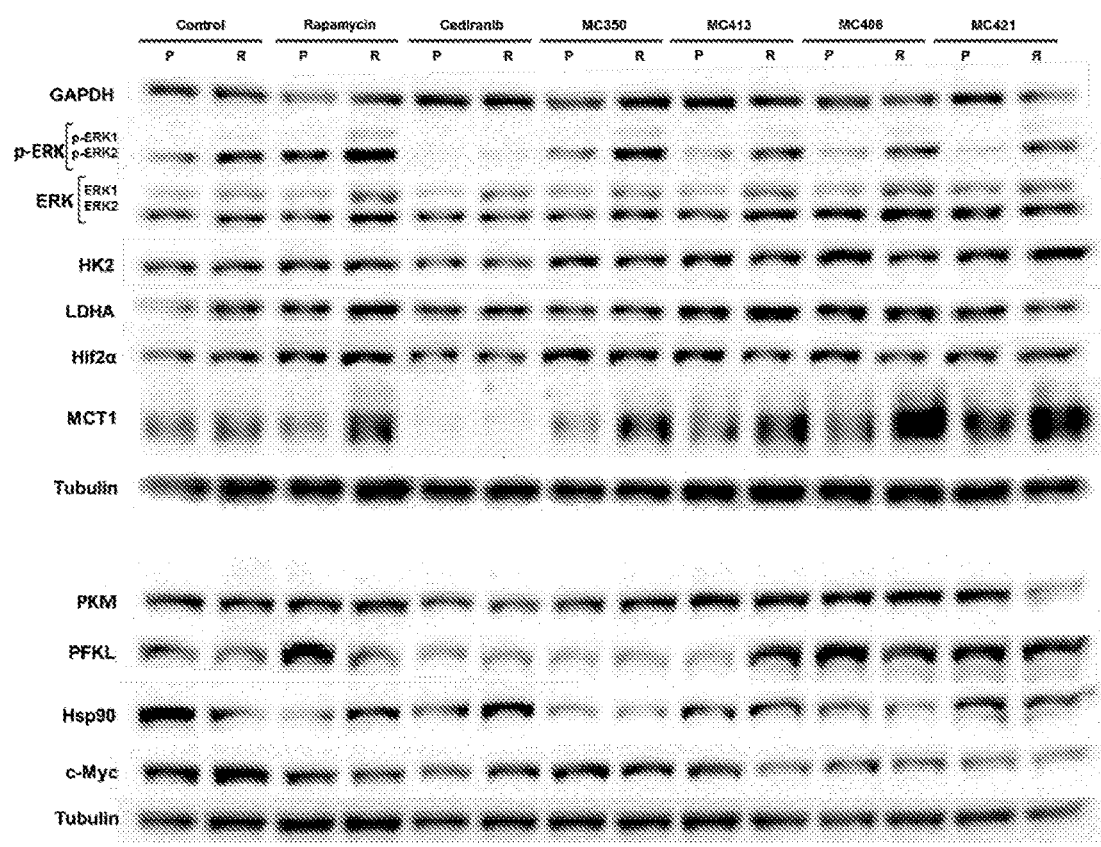
FIG. 25 shows the Western blot analysis for total and phosphorylated forms of ERK and GAPDH, HK2, LDHA, Hif2α, MCT1, PKM, PFKL, Hsp90 and c-Myc proteins after a treatment period of 48 hours with $IC_{50}$ of Rapamycin and Cediranib, compounds MC350, MC413, MC408 and MC421, on A498 parental (P) and resistant (R) cells. Detection of protein levels by Western blotting in the lysates, using 10% polyacrylamide gel.

In an embodiment, the interaction with metabolic features was further investigated through the assessment of total and phosphorylated forms of extracellular-signal-regulated kinase (ERK), Glyceraldehyde 3-phosphate dehydrogenase (GAPDH), Hexokinase 2 (HK2), Lactate dehydrogenase A (LDHA), Hypoxia inducible factor 2α (Hif2α), Monocarboxylate transporter 1 (MCT1), Pyruvate kinase isozymes (PKM), 6-phosphofructokinase (PFKL), heat shock protein 90 (Hsp90) and c-Myc proteins. These markers were assessed after a treatment period of 48 hours with the $IC_{50}$ of Rapamycin and Cediranib, compounds MC350, MC413, MC408 and MC421, on A498 parental (P) and resistant (R) cells. Detection of protein levels by Western blotting in the lysates, using 10% polyacrylamide gel (FIG. 25).

Treatment of A498 cells with different compounds led to decrease in the levels of several proteins. In fact, rapamycin-resistant cells exhibited a significant decrease in GAPDH, Hif2α, c-Myc and Hsp90 protein expression levels comparing to the control and even to parental cells. Considering the presented results, the chromenes modify the metabolic response of cancer cells, even when resistant to the currently available RCC therapy.

Figure 26:
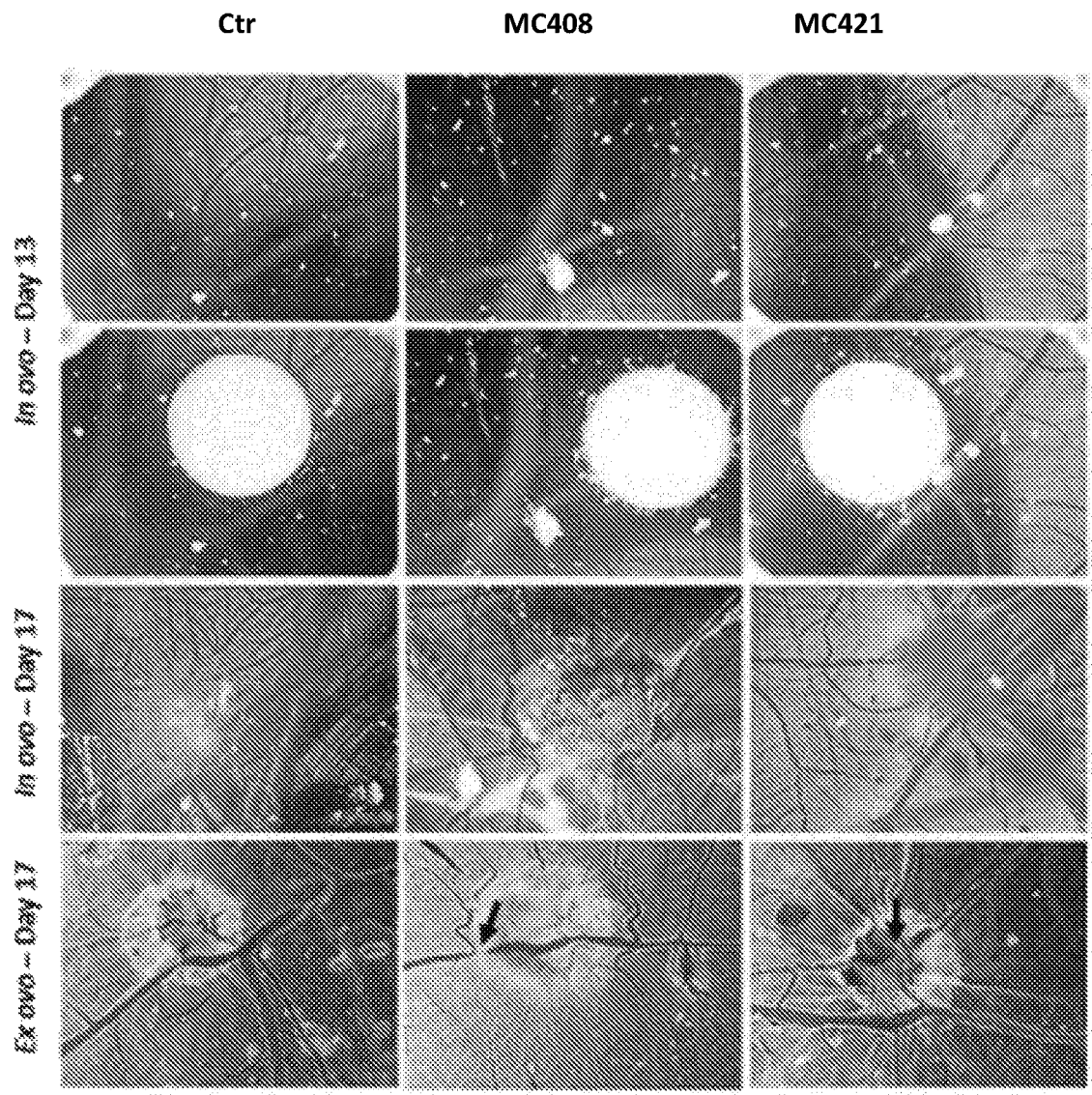
FIG. 26 shows the in vivo effect of compounds MC408 and MC421 on angiogenesis. Representative images (20× magnification) of CAM assay in ovo and ex ovo, at days 13 and 17.

In an embodiment, the in vivo capacity of the compounds to inhibit angiogenesis was analysed using the CAM model. To assess the effect on angiogenesis, sterilized 5-mm diameter filter disks were impregnated in culture medium with fixed concentration (2× the $IC_{50}$ value) of the chromenes MC408 and MC421 or 0.5% DMSO (control group) and were placed onto the vascular area of CAM. FIG. 26 shows representative pictures (×10 magnification) of the CAM assay in ovo and ex ovo (at days 13 and 17).

After 4 days of treatment with the novel chromenes, the formation of novel blood vessels decreased with chromenes MC408 and MC421. In addition, a disruption of the pre-existing blood vessels (black arrows in FIG. 26) is observed, suggesting that the compounds inhibit angiogenesis in the CAM model.

Figure 27:
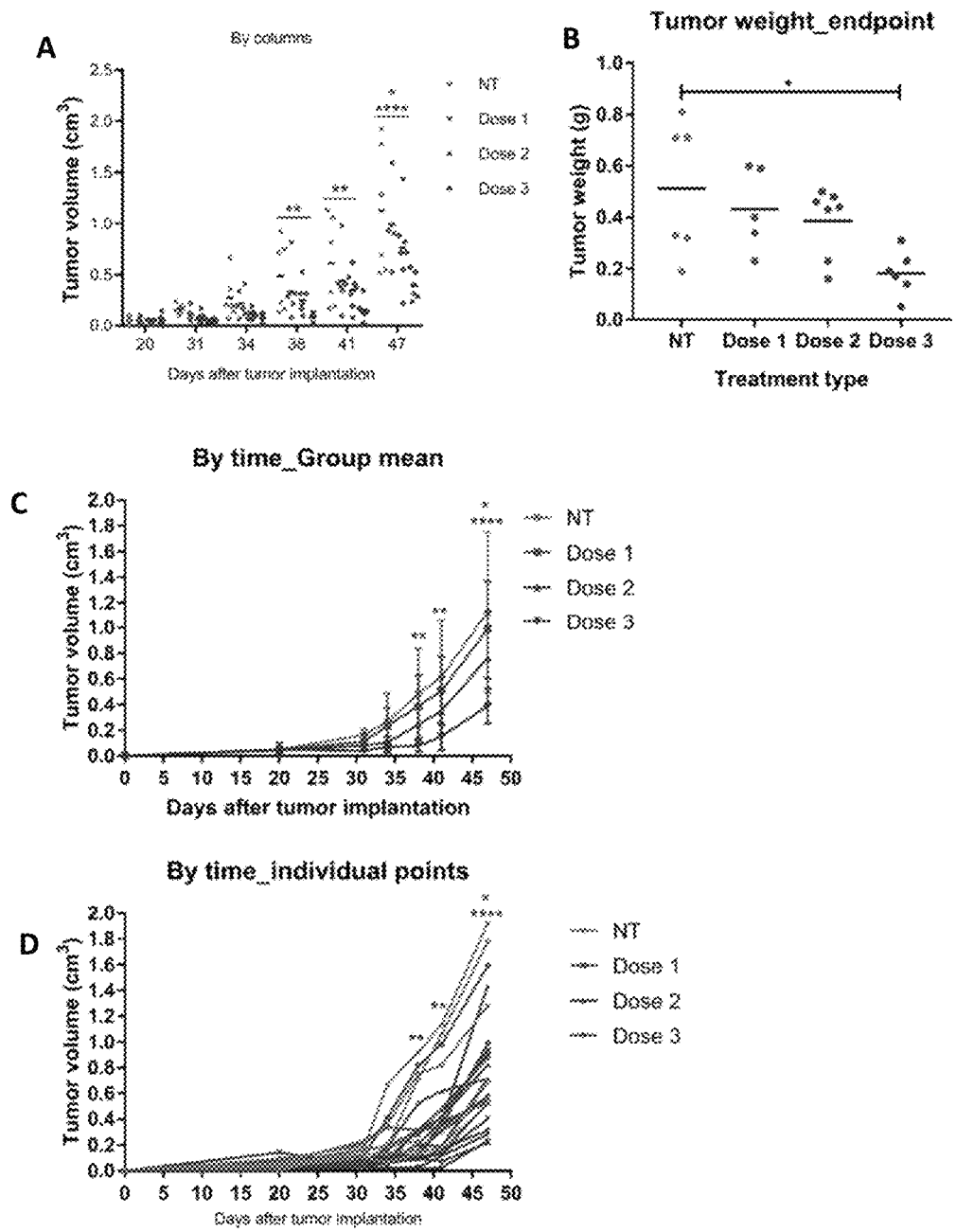
FIG. 27 shows the tumor volume and weight in an orthotopic breast cancer NSG mice xenograft model.

In an embodiment, the in vivo therapeutic efficacy of compound MC408 was analysed using the mouse model. FIG. 27 shows the in vivo therapeutic effect of MC408 in an orthotopic breast cancer mice xenograft model using the TNBC cell line MDA-MB-231. MDA-MB-231 cells were injected into the mammary fat pad of NSG mice (n=6 or 7 per group). Treatment was administered 3 days post-implantation for one week. NT=Vehicle; Dose 1=3 mg/kg; Dose 2=10 mg/kg; Dose 3=50 mg/kg. *, $p<0.05$; , $p<0.01$; **, $p<0.0001$ (compared to NT group; two-way ANOVA post-hoc Tukey's test or unpaired t-test with Welch's correction).

Chromene MC408 significantly decreased tumor volume (FIG. 27A) and weight (FIG. 27B) in an orthotopic breast cancer xenograft mice model, in a dose-dependent manner. Both tumor volume and weight, at the dose of 50 mg/kg, had a reduction of more than 40% comparing to the vehicle group. Importantly, animals presented no weight loss nor other side effects for the tested treatment regimen during the whole experiment.

In an embodiment, three human breast cancer cell lines Hs578T, MDA-MB-468 and MCF-7, and a normal breast cell line MCF-10A, were obtained from ATCC (American Type Culture Collection). The cancer cell lines were cultured in Dulbecco's modified Eagle medium, 4.5 g/l glucose (DMEM, Gibco) supplemented with 10% heating inactivated Fetal Bovine Serum (FBS, Gibco) and 1% antibiotic solution (Penicillin-Streptomycin, Gibco). The normal cell line was cultured in Dulbecco's Modified Eagle Medium: Nutrient Mixture F-12 (DMEM/F12, Gibco) supplemented with 5% heating inactivated FBS (Gibco), 1% antibiotic solution (Penicillin-Streptomycin, Gibco), 1% steroid hormone (Hydrocortisone, Sigma-Aldrich), 0.1% peptide hormone (Insulin, Sigma-Aldrich) and 0.01% protein complex (Cholera Toxin, Gibco). Two distinct human acute myeloid leukemia (AML) cell lines, HL-60 (FAB M2) and KG-1 (erythroleukemia-FAB M6), and one human lymphoblastic leukemia (ALL) cell line, Jurkat (T cell type), were also used. These three cell lines were obtained from German Collection of Microorganisms and Cell cultures (DMSZ®, Deutsche Sammlung von Mikroorganismen and Zellkulturen in German). Cells were cultured in RPMI 1640 medium (Biochrom®-Merck Millipore) supplemented with 10% heating inactivated FBS (Biochrom®-Merck Millipore) and 1% antibiotic/antimitotic mixture (Invitrogen®). Three human glioblastoma (GBM) cell line models, two established and commercially available cell lines (U87MG and GAMG, kind gift from Rui M. Reis) and one primary GBM culture (GLIB) were also used. GBM cells were cultures in DMEM (Biochrom-Merck Millipore), all supplemented with 10% FBS. The Renal cell carcinoma cell lines A498, 786-O, Caki-2 and HK2 were obtained from ATCC. The cancer cell line A498 was cultured in MEM medium (Biochrom®-Merck Millipore), 786-O was cultured in RPMI 1640 medium (Biochrom®-Merck Millipore), Caki-2 was cultured in Mc Coys medium (Biochrom®-Merck Millipore) and HK2 was cultured in RPMI 1640 medium (Biochrom®-Merck Millipore). All the media were supplemented with 10% heat inactivated FBS (Biochrom®-Merck Millipore) and 1% antibiotic/antimitotic mixture (Invitrogen®). All cells were grown in a humidified incubator at 37° C. and 5% $CO_2$. For all assays, DMSO (Dimethyl Sulfoxide, Sigma-Aldrich) controls were used.

In an embodiment, cell viability assays were performed. MCF-7, Hs578T and MCF-10A cells were plated in triplicate in 96-multiwell culture plates, at 3000 cells per mL, or 5000 cells per mL for MDA-MB-468 (100 µL/well). The cells were then allowed to adhere in complete medium, over a period of 18-20 hours. Cells were subsequently treated with 7 different concentrations (from 0.1 to 40 µM or 5 to 60 µM) of compounds or control in fresh medium. HL-60, KG-1 and Jurkat cell lines were plated in 96-multiwell culture plates at 50.000 cells/100 µL per well and treated with different concentrations (from 0.001 to 2 µM) of the compounds described (or control). Cells were plated, in triplicate, at an initial density of 2000 cells/well for GAMG, 4000 cells/well for GL18 and 6000 cells/well for U87MG, in 96-well plates, and allowed to adhere for 18-20 hours. Cells were then treated with different concentrations of the compounds (0.005 to 100 µM) or with control. A498 and 786-O cells were plated at 2000 cells per mL, Caki-2 cells were plated at 3000 cells per mL and HK2 cells were plated at 2000 cells per mL in triplicate, in 96-multiwell culture plates (100 µL/well), and allowed to adhere over a period of 18-20 hours in complete medium. The cells were then treated with 7 different concentrations (from 0.1 to 40 µM or 5 to 60 µM) of compounds or control in fresh medium. After 72 h of incubation, the MTS (Promega) reduction assay was performed according to manufacturer's instructions to indirectly assess the percentage of viable cells through metabolic cell viability. After 1-2 hours of incubation with MTS in a humidified atmosphere at 37° C. and 5% $CO_2$, absorbance was measured at 490 nm. For RCC cell lines, sulforhodamine B assay was used according to manufacturer's instructions. The data was log-transformed and the concentration of each compound that decreased the number of viable cells to 50% ($IC_{50}$) relative to control was calculated using the GraphPad Prism 6 software.

In an embodiment, the selectivity index (SI) value was calculated using the $IC_{50}$ values of all compounds for MCF-7 and MCF10A cell lines, using the following mathematical formula:

$$SI = (IC_{50}\text{ normal cell line} - IC_{50}\text{ cancer cell line})/IC_{50}\text{ cancer cell line}$$

For SI values >1, cytotoxicity for cancer cell line is higher than for non-neoplastic cell line.

In an embodiment, cell migration was assessed by the wound-healing assay that mimics the process of cell migration during wound-healing in vivo. This method is based on making a scratch, simulating a wound in a cell monolayer, capturing the images at the beginning and regular intervals during cell migration process to close the wound and comparing the images to quantify the cell migration rate. MCF-7 and Caki-2 cells were plated in 6-well plates at a density of $9.0 \times 10^5$ and $3.0 \times 10^5$ per 2 mL, respectively, and grown overnight at 37° C. in a 5% $CO_2$ humidified atmosphere. A 200 µL pipette tip was used to make two scratches in a layer of confluent cells. Cells were gently washed once with 500 µL of PBS. MCF-7 cells were treated with compounds at the respective $IC_{50}$, ½$IC_{50}$, or 0.5% DMSO (control), for 72 hours. At 0, 12, 24, 48 and 72 hours, specific wound sites (four positions for each wound) were photographed. For Caki-2 cells, a 48 h treatment was performed using the respective $IC_{50}$ of each compound, including Cediranib, or 0.5% DMSO (control) and photographed at 0, 12, 24, 36 and 48 hours. Images were captured at 100× magnification using an Olympus IX51 inverted microscope equipped with an Olympus DP20 Digital Camera System. Assessment of five migration distances was performed using BeWound 1.7.1 and the percentage of cell migration normalized to the control was plotted using GraphPad Prism 6 software. Three independent experiments were performed for each compound. The significance of the difference between different groups was determined with Student t-test.

In an embodiment, proliferation assay was performed. 786-O cells were plated in 96-well plates at a density of 7000 cells/10 µl, and allowed to incubate overnight at 37° C. in a 5% $CO_2$ humidified atmosphere. Thereafter, cells were treated with compounds MC350, MC408, MC412, MC415, MC409, MC410, MC413 and MC369 at $IC_{50}$, or ½$IC_{50}$ concentrations, or 0.5% DMSO (controls) for 48 h. After incubation, cells were labelled by addition of 10 µl/well BrdU labelling solution (final concentration: 40 µM BrdU). The cells were then re-incubated for 16 h to allow BrdU to incorporate into the proliferating cell DNA, replacing thymidine. After labelling, culture medium was removed, cells were fixed, and DNA was denatured through incubation with 200 µl of FixDenat solution at room temperature. Denaturation of DNA is essential for antibody conjugate binding to the incorporated BrdU. After FixDenat was removed, and 100 µl of anti-BrdU-POD antibody was incubated for 90 min at room temperature. The anti-BrdU-POD antibody binds to the incorporated BrdU in the newly synthesized cellular DNA. The antibody conjugate was removed, and wells were washed three times with washing solution. The immune complexes were detected by the addition of substrate solution (100 µl/well) and the plate was incubated at room temperature until color development was satisfactory for photometric detection (5-10 min). Substrate reaction was stopped by adding 25 µl of 1M $H_2SO_4$ to each well and softly mixed. The reaction product was quantified by measuring absorbance at 450 nm (reference wavelength: 690 nm) in microplate reader (Tecan Infinite M200). A blank test was used in each experimental time point, without cells, performing all steps described above. The results of at least three independent experiments (in quadruplicate) were evaluated using GraphPad Prism 5 software.

In an embodiment, protein extraction and Western Blot analysis were performed. MCF-7 and Hs578t cells were grown in T25 flasks and 786-O cells in 6-well plates, when the cells reached 70-80% confluence, the cells were treated with compounds at the respective $IC_{50}$ values or treated with 0.5% DMSO (controls). The cells were treated for 24 hours and 48 hours. Specifically in the case of RTKs and mTOR pathway analysis, 786-O cells were starved for 2 hours and then treated with a unique dose of 2 µM of Cediranib or the compounds or treated with 0.5% DMSO (controls). After treatment, adherent and floating cells were collected by scraping and centrifuged for 10 min at 2000 rpm, 4° C. The pellet was resuspended in PBS and centrifuged (1200 rpm; 5 min, 4° C.) again. The supernatant was discarded and the pellet was suspended in lysis buffer (50 mM Tris pH 7.6-8, 150 mM NaCl, 5 mM EDTA, 1 mM $Na_3VO_4$, 10 mM NaF, 1% NP-40, 1% Triton-X100 and 1/7 protease inhibitor cocktail (Roche Applied Sciences)) and incubated on ice for 20 minutes. Lysates were centrifuged for 15 minutes at 14000 rpm at 4° C.; the supernatants were then collected for protein concentration determination using DC Protein Assay Kit (BioRad).

Briefly, 30 μg of total protein of each sample were separated in 10%, 12% or 15% polyacrylamide gel (100V) and then transferred to a nitrocellulose membrane (100V for 30 minutes). The membranes were blocked with 5% milk in 1×TBS for 60 minutes before being allowed to incubate overnight at 4° C. with the specific primary antibodies (rabbit anti-PARP antibody (Cell Signaling, #9542), 1:1000 5% milk; mouse anti-caspase-9 antibody (Cell Signaling, #9508), 1:500 5% milk; rabbit anti-caspase-3 antibody (Cell Signaling, #9665), 1:500 5% milk; mouse anti-Bax antibody (Santa Cruz Biotechnology, sc-7480), 1:500 5% milk; mouse anti-Bax antibody (Santa Cruz Biotechnology, sc-8392), 1:500 5% milk; rabbit anti-Bim antibody (Cell Signaling, #2933), 1:1000 5% BSA; rabbit anti-Bid antibody (Cell Signaling, #2002), 1:1000 5% BSA; rabbit anti-KDM4C antibody (Abcam, ab27532), 1:2000 5% BSA; rat anti-Hsp90 antibody (Calbiochem, cat #386041), 1:500 5% BSA; rabbit anti-c-Myc antibody (Cell Signaling, #5605), 1:1000 5% BSA; rabbit anti-p53 antibody (Cell Signaling, #2527), 1:1000 5% BSA; rabbit anti-phospho-p53 antibody (Cell Signaling, #2521), 1:500 5% BSA; rabbit anti-p21 antibody (Cell Signaling, #2947), 1:1000 5% BSA; rabbit anti-JNK antibody (Cell Signaling, #92525), 1:500 5% BSA; rabbit anti-phospho-JNK antibody (Cell Signaling, #46685), 1:500 5% BSA; rabbit anti-mTOR antibody (Cell Signaling, #2983), 1:1000 5% BSA; rabbit anti-phospho-mTOR antibody (Cell Signaling, #5536), 1:500 5% BSA; rabbit anti-PRAS40 antibody (Cell Signaling, #2691), 1:1000 5% BSA; rabbit anti-VEGFR2 antibody (Cell Signaling, #2479), 1:500 5% BSA; rabbit anti-phospho-VEGFR2 (Tyr1175) antibody (Cell Signaling, #2478), 1:500 5% BSA; rabbit anti-EGFR antibody (Cell Signaling, #4267), 1:1500 5% BSA; rabbit anti-phospho-EGFR (Tyr1068) antibody (Cell Signaling, #2234), 1:1500 5% BSA; mouse anti-phospho-NF-kB p65 (Ser536) antibody (Cell Signaling, #3036), 1:1000 5% BSA; rabbit anti-AMPKα antibody (Cell Signaling, #2532), 1:1000 5% BSA; rabbit anti-phospho-AMPKα antibody (Thr172) (Cell Signaling, #2535), 1:1000 5% BSA; rabbit anti-AKT antibody (Cell Signaling, #4691), 1:1000 5% BSA; rabbit anti-phospho-AKT (Thr308) antibody (Cell Signaling, #13038), 1:1000 5% BSA; rabbit anti-PTEN antibody (Cell Signaling, #9559), 1:1000 5% BSA; rabbit anti-phospho-PTEN (Ser380) antibody (Cell Signaling, #9551), 1:1000 5% BSA; rabbit anti-phospho-PDK1 (Ser241) antibody (Cell Signaling, #3438), 1:1000 5% BSA; rabbit anti-phospho-p38 (Thr180/Tyr182) antibody (Cell Signaling, #4511), 1:1000 5% BSA; rabbit anti-p44/42 MAPK (Erk1/2) antibody (Cell Signaling, #4695), 1:1000 5% BSA; rabbit anti-phospho-p44/42 MAPK (Thr202/Tyr204) (phospho-Erk1/2) antibody (Cell Signaling, #4370), 1:1000 5% BSA; rabbit anti-β-tubulin antibody (Abcam, ab6046), 1:10000 5% BSA; mouse anti-GAPDH antibody (Santa Cruz Biotechnology, sc-32233), 1:1000 5% BSA; mouse anti-HK2 (Abcam, ab104836), 1:1000 5% BSA; mouse anti-LDHA antibody (Santa Cruz Biotechnology, sc-137243), 1:1000 5% BSA; rabbit anti-Hif2a antibody (Cell Signaling, #36169), 1:1000 5% BSA; rabbit anti-MCT1 antibody (Santa Cruz Biotechnology, sc-365501), 1:1000 5% BSA; rabbit anti-PKM (Abcam, ab38237), 1:1000 5% BSA; rabbit anti-PFKL (Abcam, ab37583), 1:1000 5% BSA and mouse anti-β-Actin antibody (Santa Cruz Biotechnology, #E1314), 1:500 5% milk). After washing for 5 minutes (twice) and another 15 minutes (once) with 0.1% Tween 20, blots were incubated for 1 hour with the respective secondary antibodies at room temperature (Apoptosis Antibody Sampler Kit-Cell Signaling (#9915): goat-anti-rabbit IgG-HRP (7074) and horse-anti-mouse IgG-HRP (7076) secondary antibodies, 1:2000 5% milk, Cell Signaling; and rabbit-anti-rat IgG-HRP secondary antibody (Abcam, ab6734), 1:30000, 5% BSA). After washing for 5 minutes (twice) and further 15 minutes (once) with TBS/0.1% Tween 20, immunoreactive bands were detected with chemiluminescent WesternBright™ Sirius Kit (Advansta) on ChemiDoc XRS+system (BioRad). Quantification of immunoblot was performed by Quantity One 4.6.9.

In an embodiment, cell cycle distribution by flow cytometry was performed. MCF-7, Hs578t and 786-Ocells were seeded in 6-well culture plates. Cells were allowed to adhere over a period of 18-20 hours in complete DMEM (for MCF-7 and Hs578t cells) and complete RPMI (for 786-O cells) medium and treated with $IC_{50}$ concentration of the tested compounds, or 0.5% DMSO (controls) for 12 hours and 24 hours. Each experiment was performed in triplicate. Floating and adherent cells were collected and combined by centrifugation and fixed with cold ethanol (70%). Cells were resuspended in PBS; after centrifugation and elimination of the supernatant, resuspended in a solution containing PBS, PI (50 μg/mL, P1304MP, Invitrogen), RNase A (20 mg/mL, 12091-021, Invitrogen) and Triton×100. After the final incubation for 1 hour in the dark at 5° C., PI signal was measured using a FACS LSRII flow cytometer (BD Biosciences®) with a 488 nm excitation laser, captured and FACS Diva was used as the acquisition software. The percentage of cells in each phase was analysed using the FlowJo 7.6 (Tree Star®) software. Three independent biological replicates were performed.

In an embodiment, MCF-7, Hs578t and 786-O cells were seeded in 6-well culture plates and allowed to adhere over 18-20 hours in a complete DMEM (for MCF-7 and Hs578t cells) and complete RPMI (for 786-O cells) medium to detect apoptosis via flow cytometry analysis. Cells were treated with $IC_{50}$ concentration of the tested compounds, or 0.5% DMSO (controls) for 12 hours and 24 hours. Triplicates were performed in each experiment. Floating and adherent cells were collected and combined by centrifugation. Elimination of the supernatant was followed by addition of 1 mL of Binding Buffer. 8 μL FITC annexin V (556419, BD Pharmingen) and 30 μl of PI (50 μg/mL, P1304MP, Invitrogen) were added to the cell pellet. Samples were incubated in the dark for 15 min at room temperature. A further 200 μL of Binding Buffer was added to each sample. PI signal was measured using FACS LSRII flow cytometer (BD Biosciences®) with 488 nm excitation laser. The annexin V signal was collected through a 488 nm blocking filter, a 550 nm long-pass dichroic with a 525 nm band pass. Signals were captured and FACS Diva was used as the acquisition software. The percentage of cells in each phase was analysed using the FlowJo 7.6 (Tree Star®) software. Three independent biological replicates were performed.

In an embodiment, Bristol strain N2 (provided by the CGC, funded by the NIH Office of Research Infrastructure Programs—P40 OD010440) was used to test each compound's toxicity based on a food clearance assay using *C. elegans*. The assay was performed on 96-well plates in liquid culture (Voisine et al. 2007; Teixeira-Castro et al.

2015). Each well, with a final volume of 60 µL, comprised the following: approximately 20 worms in egg stage, OP50 bacteria to a final OD of 0.6-0.8 (595 nm) and each compound at the appropriate concentration. The worms were grown with continuous shaking at 180 rpm/20° C. (Shel lab Si series incubator) for 7 days and the absorbance (OD595) was measured daily on a microplate reader (Tecan Infinite M200). The effect of the compounds on C. elegans physiology was monitored by the rate at which the E. coli food suspension was consumed (FIG. 14). Age-synchronized worm eggs were obtained by "egg prep" as follows: adult worms were treated with an alkaline hypochlorite solution (20% bleach, 25% 1M NaOH) for 6 minutes, thereafter centrifuged and washed in M9 buffer twice. The egg pellet was then re-suspended in S-medium to obtain the appropriate egg concentration before being transferred to 96-well plates. The OP50 bacteria was prepared by inactivating an overnight culture (37° C., 180 rpm, Luria Broth media) with 4 freeze-thaw cycles. Before use, the OP50 was re-suspended in supplemented S-medium (cholesterol, streptomycin, penicillin and nystatin). The compounds were prepared in 100% DMSO (Sigma) and diluted up to a test concentration of 1% DMSO to prevent solvent toxicity. For each compound, several concentrations (150-10 µM) were tested, with the exception of MC369 (75-10 µM) due to solubility issues.

For each compound, several concentrations were used and the corresponding OD595 consumption rate (slope) for days 3-5 was calculated. The compounds were tested in worms grown in 96 well plates (PlateLayout.xls, Supporting Information), in two independent experiments. For the statistical analysis, the data from both experiments were pooled together and IBM SPSS was used to apply an ANOVA (Brown-Forsythe robust test of equality of means) followed by the Games-Howell post hoc test to compare the different concentrations used for each compound and 5% DMSO (wt/v) to the control (1% DMSO(wt/v)).

In an embodiment, C57/BI6 female and male mice (n=3/group/gender) were intraperitoneally injected with MC408 (3 mg/Kg) or vehicle (saline, Tween80 and methylcellulose) daily, for 7 days to determine toxicity of the compounds in mice model. A battery of tests to assess mice welfare were performed daily. Immediately after the first drug administration, animals were videotaped and the immediate effects of MC408 were recorded. The number of vertical movements and the immobility time were recorded. Water and food intake were evaluated during the 7 days of the experiment, by adding a fixed amount of food and water in the animal's home cage in the 1st day and measuring the remaining amount at day 7. Body weight was assessed every day in a dynamic mouse scale. Horizontal and vertical activity was analysed to evaluate animals' intrinsic exploratory behavior; these were measured in an open arena with labelled squares for 1 minute and in a viewing jar for 5 minutes, respectively. Furthermore, the number of bolus faecalis were also counted while animals were performing the daily behavior assessment protocols, as a measure of anxiety. A battery of tests more related to animal welfare was applied by the experimenter, including measurements of: (i) body position and curvature; (ii) spontaneous activity; (iii) respiratory rate; (iv) eyelid opening and reflexes; (v) skin picking to analyse dehydration; (vi) grooming; (vii) fur erection; (viii) tremors; (ix) limb clasping and (x) reaction to transfer. At day 7, the animals were euthanized. All animals were deeply anesthetized (ketamine hydrochloride (150 mg/kg) and medetomidine (0.3 mg/kg)) and transcardially perfused with a saline solution (NaCl 0.9% (wt/v)). Blood was collected from the cava vein, centrifuged for 10 minutes at 13.000 rpm and the plasma was transferred to a new tube and stored at −80° C. until further processing for enzymatic liver function measurements using standard techniques. The organs (kidney, intestine, stomach, brain, liver, ovary/testis) were harvested and placed in tubes containing 4% paraformaldehyde and further processed for paraffin embedding and pathology analysis.

In an embodiment, CAM assay was performed. Fertilized chicken eggs were incubated at 37° C. and at day 3 of development, a window was opened into the eggshell after puncturing the air chamber. The window was sealed with BTK tape and returned to the incubator. On day 9 of development, Hs578t cells ($2 \times 10^6$ cells) or 786-O cells ($3.5 \times 10^6$ cells) with Matrigel (10 µL) were placed on CAM, allowing tumor formation and the eggs were tapped and returned to the incubator. At day 14 of development, the tumors were photographed. The treated groups received 20 µL of $2 \times IC_{50}$ concentration of MC408 or MC421 in complete DMEM (for Hs578t cells) or complete RPMI (for 786-O cells) media and the controls received 20 µL of 0.5% DMSO in complete DMEM or RPMI; these were added over the formed tumor. After 72 hours of treatment (day 17 of development), the tumors were photographed again in ovo. Sacrifice of chicken embryos was performed at −80° C. for 10 minutes and the CAM alone was fixed with paraformaldehyde at 4% before being photographed again ex ovo.

In an embodiment, NSG (NOD Scid Gamma) female mice (3-6 months) were injected with a mixture of $0.6 \times 10^6$ MDA-MB-231 breast cancer cells and matrigel (ratio 1:1) in the mammary fat pad. Mice were randomly assigned to treatment groups (at least 6 mice/group), which was started 3 days post-implantation using 3 independent doses of compound MC408 (dose 1=3 mg/kg, dose 2=10 mg/kg, and dose 3=50 mg/kg) or vehicle (PBS 1× and Matrigel, ratio 1:1), and was administered daily for 7 days. Mice were maintained under standard laboratory conditions. Animal tumor size (calculated by measuring the two largest sides and applying the formula: $v = 3.14 \times L1 \times L1 \times L2/6$; being L1 the largest side, and L2 the other one) was measured and recorded regularly. At day 47 post-implantation, animals were sacrificed and tumors were excised. All animal procedures were conducted in accordance with the guidelines for the care and use of laboratory animals (European Directive 2010/63/EU).

In an embodiment, the reactions of all the chemical compounds were monitored by thin layer chromatography (TLC) using silica gel 60 plates (Macherey-Nagel), with a 0.2 mm and a fluorescence indicator. A UV chamber (CN-6 Vilber Lourmat) with a 254 nm lamp was used for their revelation. Dry flash chromatography was performed using silica gel (particle size <0.063 mm) from MN Kieselgel 60 (230 ASTM). For reactions using temperature, a hot plate stirrer IKAMAG RCT was used with appropriate magnetic stirring and at different temperatures according to the specific procedure. Solvents were evaporated in a Buchi RE 11 rotary evaporator with vacuum and variable bath temperature. NMR spectra were obtained in Bruker Avance III (at 400 MHz for $^1$H NMR and 100 MHz for $^{13}$C NMR), at 25° C. and using deuterated dimethylsulfoxide (DMSO-$d_6$) as solvent.

Chemical shifts were recorded in parts per million (ppm) using the residual solvent peak as an internal standard. IR spectra were recorded in FT-IR Bomem MB 104 using nujol mulls and NaCl cells. Melting points were determined in a Stuart SMP3 apparatus and were not corrected. Elemental analysis was performed on a LECO CHNS-932 instrument.

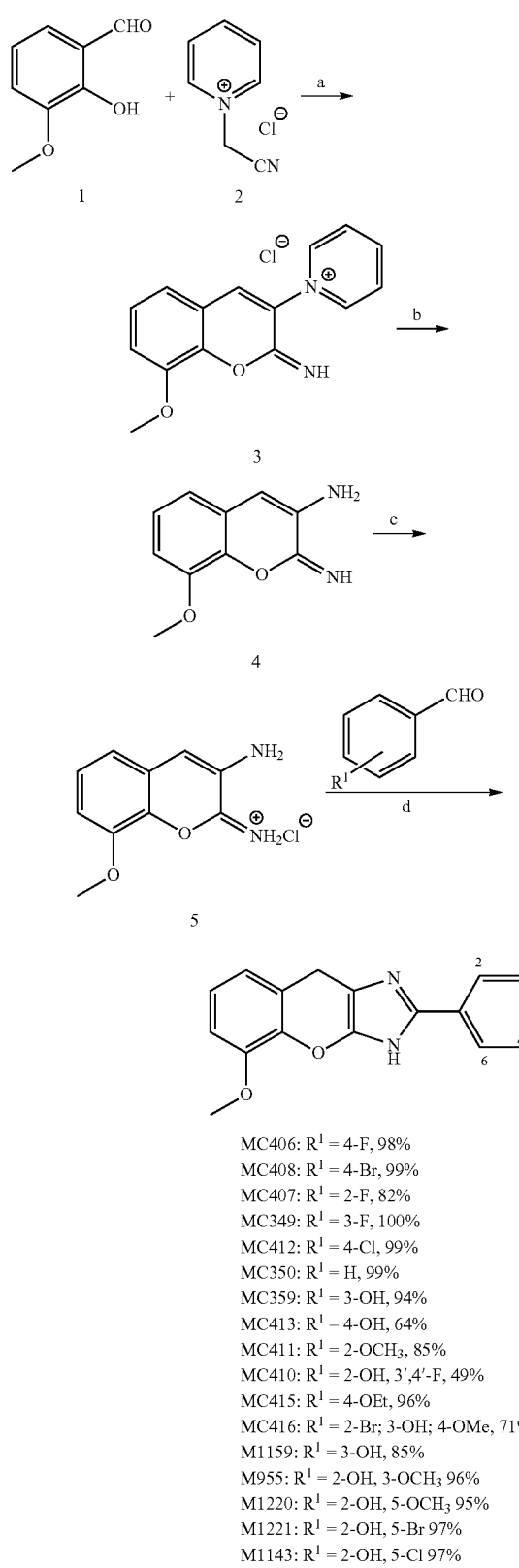

(a) EtOH, acetone, 1-methylpiperazone, 0° C.;
(b) CH₃CN, 1-methylpiperazine, rt;
(c) CH₃CN, conc. HCl, rt;
(d) CH₃CN, 80° C.

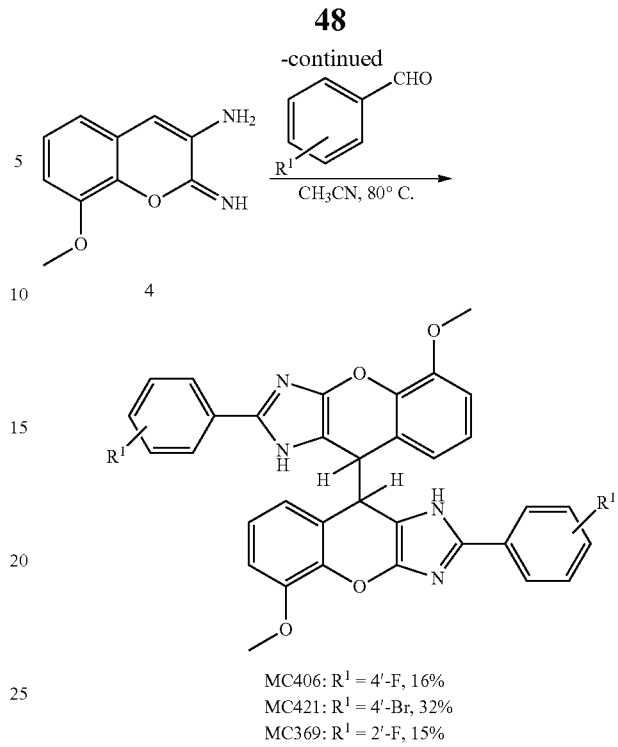

2-Imino-8-methoxy-2H-chromen-3-amine (4) and chromene derivatives M1159, M955, M1220, M1221 and M1143 can be synthetized by the above mentioned method.

In an embodiment, synthesis of 3-amino-8-methoxy-2H-chromen-2-iminium chloride (5) was performed. Concentrated HCl (1.1 equivalent) was added to an orange solution of 2-imino-8-methoxy-2H-chromen-3-amine (4) (0.150 mg; 0.79 mmol) in 1 mL of CH₃CN. Immediate precipitation was observed and the reaction mixture was stirred at room temperature for 10-15 minutes. The orange solid was isolated by simple filtration and identified as 3-amino-8-methoxy-2H-chromen-2-iminium chloride (5). Orange solid; yield 91%; mp >300° C.; $^1$H NMR (400 MHz, DMSO-$d_6$) δ 3.93 (s, 3H), 7.12-7.15 (m, 2H), 7.18 (dd, J=8.0, 1.2 Hz, 1H), 7.32 (t, J=8.0 Hz, 1H), 11.48 (s, 1H); $^{13}$C NMR (75 MHz, DMSO-$d_6$) δ 56.02, 110.13, 113.52, 117.42, 122.21, 126.39, 130.57, 135.33, 146.55, 161.15; IR (Nujol mull) ν 3322, 3192, 1678, 1654, 1600, 1576, 1552, 1460 cm$^{-1}$; Anal. Calcd for $C_{10}H_{11}N_2O_2Cl\cdot0.2H_2O$: C, 52.16; H, 4.96; N, 12.17. Found: C, 52.06; H, 4.77; N, 12.40.

In an embodiment, chromeno[2,3-d]imidazoles were synthesized. Aldehyde (1) (1.1-1.7 equivalent) was added to a suspension of 3-amino-8-methoxy-2H-chromen-2-iminium chloride (5) (0.25-0.35 mmol) in CH₃CN (1-2 mL) and the suspension was stirred at 60° C. for 24-48 hours. The solid was filtered, washed with CH₃CN and identified as the pure product. When contamination with HCl was observed in the $^1$H NMR spectrum, the solid was washed with an aqueous solution of NaHCO₃ (0.05 M), filtered and washed with water, leading to the pure product In an embodiment, 2-(4-fluorophenyl)-5-methoxy-3,9-dihydrochromeno[2,3-d]imidazoles (MC409) was synthesised. 4-Fluorobenzaldehyde (0.0375 mg; 0.30 mmol) was added to a suspension of 3-amino-8-methoxy-2H-chromen-2-iminium chloride (5) (0.047 mg; 0.21 mmol) in CH₃CN (1.6 mL) and the suspension was stirred at 60° C. for 32 hours. The solid was filtered, washed with CH₃CN and identified as the pure product. Beige solid; yield 98%; mp 191-192° C.; ¹H NMR (400 MHz, DMSO-d₆) δ 3.82 (s, 3H), 4.12 (s, 2H), 6.94 (dd, J=8.4, 1.8 Hz, 1H), 6.86 (dd, J=7.4, 1.8 Hz, 1H), 7.00 (t, J=7.8 Hz, 1H), 7.25-7.32 (m, 2H), 7.86-7.92 (m, 2H), 12.44 (s, 1H); ¹³C NMR (75 MHz, DMSO-d₆) δ 23.64, 55.75, 103.64, 110.48, 115.77 (J=21.7 Hz), 119.31, 121.82, 122.59, 126.29 (J=8.3 Hz), 127.19 (J=3.2 Hz), 138.88, 141.25, 148.19, 148.38, 161.78 (J=243.4 Hz); IR (Nujol mull) ν 3348, 1700, 1650, 1608, 1578, 1538, 1500, 1461 cm⁻¹; Anal. Calcd for C₁₇H₁₃N₂O₂F: C, 68.91; H, 4.42; N, 9.45. Found: C, 68.89; H, 4.65; N, 9.56.

In an embodiment, 2-(4-bromophenyl)-5-methoxy-3,9-dihydrochromeno[2,3-d]imidazoles (MC408) was synthesised. 4-Bromobenzaldehyde (0.0737 mg; 0.40 mmol) was added to a suspension of 3-amino-8-methoxy-2H-chromen-2-iminium chloride (5) (0.0758 mg; 0.34 mmol) in CH₃CN (2 mL) and the suspension was stirred at 60° C. for 24 hours. The solid was filtered, washed with CH₃CN and identified as the pure product. When contamination with HCl was observed in the ¹H NMR spectrum, the solid was washed with an aqueous solution of NaHCO₃ (0.05 M; 2 mL), filtered and washed with water, leading to the pure product. Yellow solid; yield 99%; mp 215-217° C.; ¹H NMR (400 MHz, DMSO-d₆) δ 3.82 (s, 3H), 4.11 (s, 2H), 6.86 (dd, J=7.6, 1.2 Hz, 1H), 6.94 (dd, J=7.8, 1.2 Hz, 1H), 7.01 (t, J=8.0 Hz, 1H), 7.63 (dd, J=6.8, 2.0 Hz, 2H), 7.80 (dd, J=6.8, 2.0 Hz, 2H), 12.62 (s, 1H); ¹³C NMR (75 MHz, DMSO-d₆) δ 23.61, 55.77, 104.40, 110.54, 119.25, 120.87, 121.81, 122.70, 126.15 (2C), 129.53, 131.76 (3C), 138.51, 141.16, 148.36; IR (Nujol mull) ν 3435, 1717, 1639, 1603, 1576, 1536, 1463 cm⁻¹; Anal. Calcd for C₁₇H₁₃N₂O₂Br·1.9H₂O: C, 52.12; H, 4.29; N, 7.15. Found: C, 52.12; H, 3.93; N, 7.37.

In an embodiment, 2-(2-fluorophenyl)-5-methoxy-3,9-dihydrochromeno[2,3-d]imidazoles (MC407) was synthesised. 2-Fluorobenzaldehyde (0.0389 mg; 0.31 mmol) was added to a suspension of 3-amino-8-methoxy-2H-chromen-2-iminium chloride (5) (0.0571 mg; 0.25 mmol) in CH₃CN (2 mL) and the suspension was stirred at 60° C. for 24 hours. The solid was filtered, washed with CH₃CN and identified as the pure product. Beige solid; yield 82%; mp 102-103° C.; ¹H NMR (400 MHz, DMSO-d₆) δ 3.82 (s, 3H), 4.10 (s, 2H), 6.86 (dd, J=7.6, 2.4 Hz, 1H), 6.94 (dd, J=8.0, 2.4 Hz, 1H), 7.00 (t, J=8.0 Hz, 1H), 7.26-7.40 (m, 3H), 7.95 (dd, J=8.0, 1.6 Hz, 1H), 12.09 (s, 1H); ¹³C NMR (75 MHz, DMSO-d₆) δ 23.93, 55.79, 104.61, 110.54, 116.22 (J=16.1 Hz), 118.22 (J=8.6 Hz), 119.44, 121.85, 122.67, 124.94 (J=2.3 Hz), 128.20 (J=2.2 Hz), 129.61 (J=6.2 Hz), 134.50, 141.24, 148.15, 148.38, 158.53 (J=184.5 Hz); IR (Nujol mull) ν 3426, 1710, 1631, 1603, 1576, 1536, 1463 cm⁻¹; Anal. Calcd for C₁₇H₁₃N₂O₂F1.1H₂O: C, 64.60; H, 4.46; N, 8.87. Found: C, 64.36; H, 4.46; N, 8.91.

In an embodiment, 2-(3-fluorophenyl)-5-methoxy-3,9-dihydrochromeno[2,3-d]imidazoles (MC349) was synthesised. 3-Fluorobenzaldehyde (0.0482 mg; 0.39 mmol) was added to a suspension of 3-amino-8-methoxy-2H-chromen-2-iminium chloride (5) (0.0712 mg; 0.31 mmol) in CH₃CN (1 mL) and the suspension was stirred at 60° C. for 33 hours. The solid was filtered, washed with CH₃CN and identified as the pure product. Beige solid; yield 100%; mp 198-200° C.; ¹H NMR (400 MHz, DMSO-d₆) δ 3.82 (s, 3H), 4.12 (s, 2H), 6.86 (dd, J=7.6, 1.2 Hz, 1H), 6.94 (dd, J=8.0, 1.2 Hz, 1H), 7.00 (t, J=8.6 Hz, 1H), 7.13 (td, J=8.6, 2.8 Hz, 1H), 7.44-7.51 (m, 1H), 7.73 (dt, J=10.4, 2.8 Hz, 1H), 7.70 (d, J=7.6 Hz, 1H), 12.58 (s, 1H); ¹³C NMR (75 MHz, DMSO-d₆) δ 23.60, 55.79, 104.46, 110.56, 110.68 (J=18.4 Hz), 114.43 (J=15.8 Hz), 119.24, 120.23 (J=1.8 Hz), 121.81, 122.68, 130.95 (J=6.4 Hz), 132.78 (J=6.4 Hz), 138.39 (J=2.3 Hz), 141.21, 148.31, 148.38, 162.52 (J=180.8 Hz); IR (Nujol mull) ν 3356, 1707, 1652, 1628, 1522, 1508, 1461 cm⁻¹; Anal. Calcd for C₁₇H₁₃N₂O₂F: C, 68.91; H, 4.42; N, 9.45. Found: C, 68.98; H, 4.58; N, 9.66.

In an embodiment, 2-(4-chlorophenyl)-5-methoxy-3,9-dihydrochromeno[2,3-d]imidazoles (MC412) was synthesised. 4-Chlorobenzaldehyde (0.0291 mg; 0.21 mmol) was added to a suspension of 3-amino-8-methoxy-2H-chromen-2-iminium chloride (5) (0.0417 mg; 0.18 mmol) in CH₃CN (1 mL) and the suspension was stirred at 60° C. for 24 hours. The solid was filtered, washed with CH₃CN and identified as the pure product. Beige solid; yield 100%; mp 212-214° C.; ¹H NMR (400 MHz, DMSO-d₆) δ 3.82 (s, 3H), 4.12 (s, 2H), 6.86 (dd, J=7.6, 1.6 Hz, 1H), 6.94 (dd, J=8.2, 1.6 Hz, 1H), 7.00 (t, J=8.0 Hz, 1H), 7.50 (d, J=8.4 Hz, 2H), 7.86 (d, J=8.4 Hz, 2H), 12.53 (s, 1H); ¹³C NMR (75 MHz, DMSO-d₆) δ 23.62, 55.76, 104.18, 110.52, 119.25, 121.80, 122.62, 125.84 (2C), 128.84 (2C), 129.36, 132.18, 138.55, 141.22, 148.31, 148.36; IR (Nujol mull) ν 3352, 1700, 1656, 1601, 1532, 1489, 1462 cm⁻¹; Anal. Calcd for C₁₇H₁₃N₂O₂Cl: C, 65.29; H, 4.19; N, 8.96. Found: C, 65.47; H, 4.23; N, 8.74.

In an embodiment, 5-methoxy-2-phenyl-3,9-dihydrochromeno[2,3-d]imidazoles (MC350) was synthesised. Benzaldehyde (0.0520 mg; 0.49 mmol) was added to a suspension of 3-amino-8-methoxy-2H-chromen-2-iminium chloride (5) (0.0653 mg; 0.29 mmol) in CH₃CN (1 mL) and the suspension was stirred at 60° C. for 33 hours. The solid was filtered, washed with CH₃CN and identified as the pure product. When contamination with HCl was observed in the ¹H NMR spectrum, the solid was washed with an aqueous solution of NaHCO₃ (0.05 M), filtered and washed with water, leading to the pure product. Beige solid; yield 99%; mp 162-16° C.; ¹H NMR (400 MHz, DMSO-d₆) δ 3.83 (s, 3H), 4.12 (s, 2H), 6.86 (dd, J=7.6, 1.6 Hz, 1H), 6.94 (dd, J=8.0, 1.6 Hz, 1H), 7.00 (t, J=8.0 Hz, 1H), 7.31 (t, J=7.6 Hz, 1H), 7.43 (t, J=8.0 Hz, 2H), 7.86 (d, J=7.8 Hz, 2H), 12.43 (s, 1H); ¹³C NMR (75 MHz, DMSO-d₆) δ 23.68, 55.77, 110.50, 119.33, 121.83, 122.56, 124.20 (2C), 127.77, 128.75 (2C), 130.50, 139.62, 141.29, 148.23, 148.38; IR (Nujol mull) ν 3346, 1702, 1648, 1602, 1526, 1496, 1461 cm⁻¹; Anal. Calcd for C₁₇H₁₄N₂O₂: C, 73.37; H, 5.07; N, 10.07. Found: C, 73.58; H, 5.12; N, 10.34.

In an embodiment, 3-(5-methoxy-3,9-dihydrochromeno[2,3-d]imidazol-2-yl)phenol (MC359) was synthesised. 3-Hydroxybenzaldehyde (0.0427 mg; 0.35 mmol) was added to a suspension of 3-amino-8-methoxy-2H-chromen-2-iminium chloride (5) (0.0679 mg; 0.30 mmol) in CH₃CN (1.2 mL) and the suspension was stirred at 6° C. for 28 hours. The solid was filtered, washed with CH₃CN and identified as the pure product. When contamination with HCl was observed in the ¹H NMR spectrum, the solid was washed with an aqueous solution of NaHCO₃ (0.05 M), filtered and washed with water, leading to the pure product. Light green solid; yield 94%; mp 162-164° C.; ¹H NMR (400 MHz, DMSO-d6) δ 3.82 (s, 3H), 4.10 (s, 2H), 6.71 (dq, J=8.2, 1.2 Hz, 1H), 6.85 (dd, J=7.8, 1.2 Hz, 1H), 6.92 (dd, J=8.2, 1.2 Hz, 1H), 7.00 (t, J=7.6 Hz, 1H), 7.21 (t, J=7.6 Hz, 2H), 7.27-7.30 (m, 2H), 9.55 (s, 1H), 12.33 (s, 1H); ¹³C NMR (75 MHz, DMSO-d₆) δ 23.70, 55.75, 110.47, 111.23, 114.99, 115.07, 119.36, 121.84, 122.54, 129.74, 131.77, 139.76, 141.30, 148.10, 148.37, 157.62; IR (Nujol mull) ν 3351, 3218, 1702, 1659, 1611, 1523, 1507, 1460 cm⁻¹; Anal. Calcd for C₁₇H₁₄N₂O₃: C, 69.38; H, 4.79; N, 9.52. Found: C, 69.42; H, 4.88; N, 9.56.

In an embodiment, 4-(5-methoxy-3,9-dihydrochromeno[2,3-d]imidazol-2-yl)phenol (MC413) was synthesised. 4-Hydroxybenzaldehyde (0.0388 mg; 0.32 mmol) was added to a suspension of 3-amino-8-methoxy-2H-chromen-2-iminium chloride (5) (0.0579 mg; 0.26 mmol) in $CH_3CN$ (2 mL) and the suspension was stirred at 60° C. for 48 hours. The solid was filtered, washed with $CH_3CN$ and identified as the pure product. When contamination with HCl was observed in the $^1H$ NMR spectrum, the solid was washed with an aqueous solution of $NaHCO_3$ (0.05 M), filtered and washed with water, leading to the pure product. Yellow solid; yield 64%; mp 245-246° C.; $^1H$ NMR (400 MHz, DMSO-$d_6$) δ 3.82 (s, 3H), 4.09 (s, 2H), 6.81 (dd, J=6.8, 2.0 Hz, 2H), 6.85 (dd, J=7.6, 1.6 Hz, 1H), 6.92 (dd, J=8.0, 1.6 Hz, 1H), 6.99 (t, J=8.0 Hz, 1H), 7.68 (dd, J=6.8, 2.0 Hz, 2H), 9.63 (s, 1H), 12.11 (s, 1H); $^{13}C$ NMR (75 MHz, DMSO-$d_6$) δ23.76, 55.75, 102.26, 110.43, 115.48 (2C), 119.45, 121.86 (2C), 122.45, 125.88 (2C), 140.34, 141.36, 147.86, 148.37, 157.44; IR (Nujol mull) v 3338, 3246, 1706, 1645, 1612, 1548, 1503, 1463 $cm^{-1}$; Anal. Calcd for $C_{17}H_{14}N_2O_3$: C, 69.38; H, 4.79; N, 9.52. Found: C, 69.39; H, 4.42; N, 9.54.

In an embodiment, 5-methoxy-2-(2-methoxyphenyl)-3,9-dihydrochromeno[2,3-]imidazoles (MC411) was synthesised. 2-Methoxybenzaldehyde (0.0632 mg; 0.46 mmol) was added to a suspension of 3-amino-8-methoxy-2H-chromen-2-iminium chloride (5) (0.0780 mg; 0.34 mmol) in $CH_3CN$ (1 mL) and the suspension was stirred at 60° C. for 47 hours. The solid was filtered, washed with $CH_3CN$ and identified as the pure product. When contamination with HCl was observed in the $^1H$ NMR spectrum, the solid was washed with an aqueous solution of $NaHCO_3$ (0.05 M), filtered and washed with water, leading to the pure product. Yellow solid; yield 85%; mp 188-190° C.; $^1H$ NMR (400 MHz, DMSO-$d_6$) δ 3.82 (s, 3H), 3.95 (s, 3H), 4.10 (s, 2H), 6.86 (dd, J=7.6, 1.6 Hz, 1H), 6.93 (dd, J=8.0, 1.6 Hz, 1H), 6.97-7.04 (m, 2H), 7.13 (dd, J=8.0, 0.8 Hz, 1H), 7.30 (td, J=7.7, 2.0 Hz, 1H), 7.99 (dd, J=8.0, 2.0 Hz, 1H), 11.63 (s, 1H); $^{13}C$ NMR (100 MHz, DMSO-$d_6$) δ 24.30, 55.50, 55.78, 103.05, 110.47, 111.72, 118.44, 119.67, 120.78, 121.91, 122.51, 127.39, 128.95, 137.14, 141.34, 147.76, 148.38, 155.59; IR (Nujol mull) v 3340, 1706, 1659, 1594, 1530, 1506, 1460 $cm^{-1}$; Anal. Calcd for $C_{18}H_{16}N_2O_3$: C, 70.12; H, 5.23; N, 9.09. Found: C, 70.44; H, 5.20; N, 9.16.

In an embodiment, 2,4-difluoro-6-(5-methoxy-3,9-dihydrochromeno[2,3-d]imidazol-2-yl)phenol (MC410) was synthesised. 2,4-Difluoro-6-hydroxybenzaldehyde (0.0493 mg; 0.31 mmol) was added to a suspension of 3-amino-8-methoxy-2H-chromen-2-iminium chloride (5) (0.061 mg; 0.27 mmol) in $CH_3CN$ (2 mL) and the suspension was stirred at 60° C. for 36 hours. The solid was filtered, washed with $CH_3CN$ and identified as the pure product. When contamination with HCl was observed in the $^1H$ NMR spectrum, the solid was washed with an aqueous solution of $NaHCO_3$ (0.05 M), filtered and washed with water, leading to the pure product. Yellow solid; yield 49%; mp 260-262° C.; $^1H$ NMR (400 MHz, DMSO-$d_6$) δ 3.83 (s, 3H), 4.15 (s, 2H), 6.87 (dd, J=7.6, 2.4 Hz, 1H), 6.96 (dd, J=8.2, 2.4 Hz, 1H), 7.04 (t, J=8.0 Hz, 1H), 7.24 (td, J=10.0, 1.6 Hz, 1H), 7.51 (dt, J=10.0, 1.6 Hz, 1H), 11.91 (s, 1H), 12.90 (s, 1H); $^{13}C$ NMR (75 MHz, DMSO-$d_6$) δ 23.28, 55.70, 104.31 (dd, J=20.6, 16.5 Hz), 104.39, 105.38 (dd, J=18.8, 4.5 Hz), 110.59, 115.36 (dd, J=7.9, 4.5 Hz), 119.03, 121.71, 123.14, 137.71-137.79 (m), 140.30 (J=10.2, 4.5 Hz), 140.68, 145.62, 148.29, 150.80 (dd, J=181.9, 10.0), 153.9 (dd, J=175.9, 8.8); IR (Nujol mull) v 3348, 3225, 1698, 1651, 1601, 1542, 1461 $cm^{-1}$; Anal. Calcd for $C_{17}H_{12}N_2O_3F_2 \cdot 0.8H_2O$: C, 59.23; H, 3.72; N, 8.13. Found: C, 59.13; H, 3.53; N, 8.42.

In an embodiment, 2-(4-ethoxyphenyl)-5-methoxy-3,9-dihydrochromeno[2,3-d]imidazoles (MC415) was synthesised. 4-Ethoxybenzaldehyde (0.0403 mg; 0.30 mmol) was added to a suspension of 3-amino-8-methoxy-2H-chromen-2-iminium chloride (5) (0.0614 mg; 0.27 mmol) in $CH_3CN$ (2 mL) and the suspension was stirred at 60° C. for 47 hours. The solid was filtered, washed with $CH_3CN$ and identified as the pure product. When contamination with HCl was observed in the $^1H$ NMR spectrum, the solid was washed with an aqueous solution of $NaHCO_3$ (0.05 M), filtered and washed with water, leading to the pure product. Yellow solid; yield 96%; mp 215-217° C.; $^1H$ NMR (400 MHz, DMSO-$d_6$) δ 1.20 (t, J=7.6 Hz, 3H), 2.62 (q, J=7.6 Hz, 2H), 3.84 (s, 3H), 4.12 (s, 2H), 6.87 (dd, J=7.2, 1.6 Hz, 1H), 6.94 (dd, J=8.2, 1.2 Hz, 1H), 7.01 (t, J=7.6 Hz, 1H), 7.28 (d, J=8.4 Hz, 2H), 7.79 (dd, J=6.6, 1.6 Hz, 2H), 12.36 (s, 1H); $^{13}C$ NMR (75 MHz, DMSO-$d_6$) δ 15.43, 23.73, 27.94, 55.80, 103.30, 110.52, 119.41, 121.87, 122.59, 124.33 (2C), 128.08, 128.16 (2C), 139.87, 141.33, 143.60, 148.40; IR (Nujol mull) v 3342, 1703, 1656, 1610, 1539, 1502, 1460 $cm^{-1}$; Anal. Calcd for $C_{19}H_{18}N_2O_3$: C, 70.81; H, 5.59; N, 8.70. Found: C, 70.74; H, 5.67; N, 8.77.

In an embodiment, 2-bromo-6-methoxy-3-(5-methoxy-3,9-dihydrochromeno[2,3-]imidazol-2-yl)phenol (MC416) was synthesised. 2-Bromo-3-hydroxy-4-methoxybenzaldehyde (0.0780 mg; 0.34 mmol) was added to a suspension of 3-amino-8-methoxy-2H-chromen-2-iminium chloride (5) (0.0607 mg; 0.27 mmol) in $CH_3CN$ (1 mL) and the suspension was stirred at 60° C. for 46 hours. The solid was filtered, washed with $CH_3CN$ and identified as the pure product. When contamination with HCl was observed in the $^1H$ NMR spectrum, the solid was washed with an aqueous solution of $NaHCO_3$ (0.05 M), filtered and washed with water, leading to the pure product. Beige solid; yield 71%; mp 160-161° C.; $^1H$ NMR (400 MHz, DMSO-$d_6$) δ 3.82 (s, 3H), 3.86 (s, 3H), 4.08 (s, 2H), 6.85 (dd, J=7.6, 1.2 Hz, 1H), 6.93 (dd, J=8.0, 1.6 Hz, 1H), 6.99 (t, J=8.0 Hz, 1H), 7.03-7.08 (m, 2H), 9.55 (s, 1H), 11.97 (s, 1H); $^{13}C$ NMR (75 MHz, DMSO-$d_6$) δ 23.82, 55.74, 56.23, 102.75, 109.30, 110.43, 110.54, 119.46, 121.38, 121.84, 122.46, 125.26, 139.04, 141.33, 144.05, 147.52, 148.29, 148.37; IR (Nujol mull) v 3338, 3212, 1703, 1647, 1535, 1497, 1461 $cm^{-1}$; Anal. Calcd for $C_{18}H_{15}N_2O_4Br \cdot 1.8H_2O$: C, 49.61; H, 3.86; N, 6.43. Found: C, 49.68; H, 3.91; N, 6.43.

In an embodiment, 5,5'-dimethoxy-2,2'-diphenyl-1,1,9,9'-tetrahydro-9,9'-bichromeno[2,3-d]imidazoles were synthesized. Aldehyde (1) (1-1.2 equivalent) was added to a solution of 2-imino-8-methoxy-2H-chromen-3-amine (4) in $CH_3CN$ (1-2 mL) and the solution was stirred at 80° C. for 7-24 hours. The solid product started to precipitate slowly, was filtered, washed with $CH_3CN$ and identified as the pure product 8.

In an embodiment, 2,2'-bis(4-fluorophenyl)-5,5'-dimethoxy-1,1,9,9'-tetrahydro-9,9'-bichromeno[2,3-]imidazoles (MC406) was synthesised. 4-Fluorobenzaldehyde (0.0629 mg; 0.51 mmol) was added to a solution of 2-imino-8-methoxy-2H-chromen-3-amine (4) (0.0962 mg; 0.51 mmol) in $CH_3CN$ (1 mL) and the solution was stirred at 80° C. for 7 hours. The solid product started to precipitate slowly, was filtered, washed with $CH_3CN$ and identified as the pure product. Beige solid; yield 18%; mp 272-274° C.; $^1H$ NMR (400 MHz, DMSO-$d_6$) δ 3.68 (s, 6H), 4.89 (s, 2H), 5.80 (dd, J=7.8, 2.0 Hz, 2H), 6.71 (t, J=7.8 Hz, 2H), 6.80 (dd, J=8.7, 1.6 Hz, 2H), 7.32-7.49 (m, 4H), 7.98-8.03 (m, 4H), 12.57 (s, 2H); $^{13}C$ NMR (75 MHz, DMSO-$d_6$) δ 41.21, 55.64, 105.81, 111.00, 115.83 (2C, J=21.2), 119.62, 120.44, 122.01, 126.80 (2C, J=8.0), 127.12, 139.98, 141.90, 147.62, 150.12, 162.00 (J=243.8); IR (Nujol mull) v 3348, 1700, 1650, 1608, 1538, 1500, 1461 $cm^{-1}$; Anal. Calcd for $C_{34}H_{24}N_4O_4F_2 \cdot 1.2H_2O$: C, 64.23; H, 4.85; N, 8.82. Found: C, 64.21; H, 4.79; N, 8.80.

In an embodiment, 2,2'-bis(4-bromophenyl)-5,5'-dimethoxy-1,1,9,9'-tetrahydro-9,9'-bichromeno[2,3-]imidazoles (MC421) was synthesised. 4-Bromobenzaldehyde (0.069 mg; 0.37 mmol) was added to a solution of 2-imino-8-methoxy-2H-chromen-3-amine (4) (0.0705 mg; 0.37 mmol) in $C_3CN$ (1.5 mL) and the solution was stirred at 80° C. for 8 hours. The solid product started to precipitate slowly, was filtered, washed with $CH_3CN$ and identified as the pure product. Beige solid; yield 32%; mp 266-268° C.; $^1H$ NMR (400 MHz, DMSO-$d_6$) δ 3.68 (s, 6H), 4.89 (s, 2H), 5.78 (dd, J=7.8, 1.6 Hz, 2H), 6.71 (t, J=7.8 Hz, 2H), 6.80 (dd, J=8.2, 2.0 Hz, 2H), 7.71 (dd, J=6.6, 1.4 Hz, 2H), 7.91 (dd, J=6.9, 1.6 Hz, 2H), 12.69 (s, 2H); $^{13}C$ NMR (75 MHz, DMSO-$d_6$) δ 41.24, 55.65, 106.33, 111.06, 119.52, 120.41, 121.14, 122.06, 126.58, 129.65, 131.80, 139.70, 141.86, 147.62, 150.25; IR (Nujol mull) v 3352, 1703, 1654, 1610, 1543, 1508, 1461 $cm^{-1}$; Anal. Calcd for $C_{34}H_{24}N_4O_4Br_2$: C, 57.32; H, 3.40; N, 7.86. Found: C, 57.78; H, 3.37; N, 7.88.

In an embodiment, 2,2'-bis(2-fluorophenyl)-5,5'-dimethoxy-1,1,9,9'-tetrahydro-9,9'-bichromeno[2,3-]imidazoles (MC369) was synthesised. 2-Fluorobenzaldehyde (0.0446 mg; 0.36 mmol) was added to a solution of 2-imino-8-methoxy-2H-chromen-3-amine (4) (0.0590 mg; 0.31 mmol) in $CH_3CN$ (2 mL) and the solution was stirred at 80° C. for 24 hours. The solid product started to precipitate slowly, was filtered, washed with $CH_3CN$ and identified as the pure product. Beige solid; yield 15%; mp 276-278° C.; $^1H$ NMR (400 MHz, DMSO-$d_6$) δ 3.69 (s, 6H), 5.00 (s, 2H), 5.91 (dd, J=8.0, 1.2 Hz, 2H), 6.75 (t, J=8.0 Hz, 2H), 6.82 (dd, J=8.2, 1.6 Hz, 2H), 7.31-7.48 (m, 6H), 7.99 (td, J=5.7, 1.6 Hz, 2H), 11.88 (s, 2H); $^{13}C$ NMR (75 MHz, DMSO-$d_6$) δ 41.08, 55.65, 106.63, 110.99, 116.28 (J=21.3), 118.24 (J=11.4), 120.02, 120.45, 122.06, 124.98, 128.60 (J=2.8), 129.98 (J=8.2), 135.58, 141.90, 147.62, 149.93, 158.73 (J=246.6); IR (Nujol mull) v 3438, 3447, 1637, 1575, 1614, 1575, 1530, 1469 $cm^{-1}$; Anal. Calcd for $C_{34}H_{24}N_4O_4F_2.0.8H_2O$: C, 67.51; H, 4.23; N, 9.26. Found: C, 67.58; H, 4.30; N, 9.11.

The term "comprising" whenever used in this document is intended to indicate the presence of stated features, integers, steps, components, but not to preclude the presence or addition of one or more other features, integers, steps, components or groups thereof.

It will be appreciated by those of ordinary skill in the art that unless otherwise indicated herein, the particular sequence of steps described is illustrative only and can be varied without departing from the disclosure. Thus, unless otherwise stated the steps described are so unordered meaning that, when possible, the steps can be performed in any convenient or desirable order.

Where singular forms of elements or features are used in the specification of the claims, the plural form is also included, and vice versa, if not specifically excluded. For example, the term "a compound" or "the compound" also includes the plural forms "compounds" or "the compounds," and vice versa. In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process.

Furthermore, it is to be understood that the invention encompasses all variations, combinations, and permutations in which one or more limitations, elements, clauses, descriptive terms, etc., from one or more of the claims or from relevant portions of the description is introduced into another claim. For example, any claim that is dependent on another claim can be modified to include one or more limitations found in any other claim that is dependent on the same base claim.

Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

The disclosure should not be seen in any way restricted to the embodiments described and a person with ordinary skill in the art will foresee many possibilities to modifications thereof.

The above described embodiments are combinable.

REFERENCES (1) https://www.uicc.org/new-global-cancer-data-globocan-2018 (02/01/2019)

(2) http://gco.iarc.fr (02/01/2019)

(3) Bao, B; Mitrea, C.; Wijesinghe, P.; Marchetti, L.; Girsch, E.; Farr, R.; Boerner, J.; Mohammad, R.; Dyson, G.; Terlecky, S. and Bollig-Fischer, A. Treating triple negative breast cancer cells with erlotinib plus a select antioxidant overcomes drug resistance by targeting cancer cell heterogeneity. Scientific Reports 2017, 7, 44125.

(4) Costa, M.; Dias, T.; Brito, A. And Proenga, F. Biological importance of structurally diversified chromenes. Eur. J. Med. Chem, 2016, 123, 487-507.

(5) Costa, M.; Rodrigues, A. I.; Proenca, F. Synthesis of 3-aminochromenes: the Zincke reaction revisited. Tetrahedron 2014, 70 (33), 4869.

(6) Costa, M.; Proenca, F. 2-Aryl-1,9-dihydrochromeno[3,2-d]imidazoles: a facile synthesis from salicylaldehydes and arylideneaminoacetonitrile. Tetrahedron 2011, 67 (10), 1799.

The invention claimed is:

1. A compound having the structure:

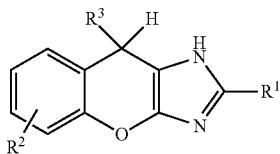

wherein

R¹ is substituted aryl, or substituted phenyl;
R² is H, alkyl, alkoxyl, halogen, hydroxyl, or amine;
R³ is H or

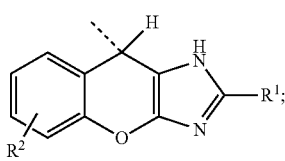

with the proviso that

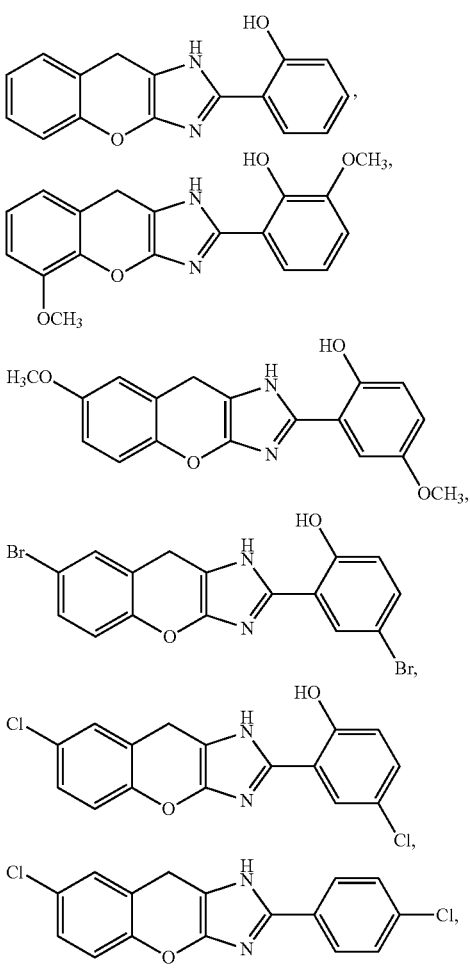

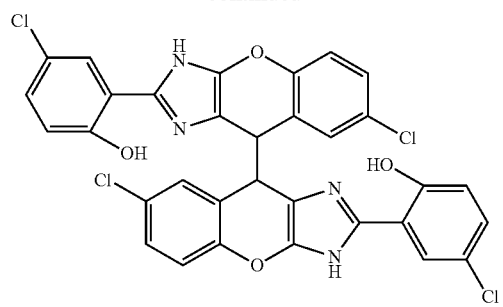

are excluded, or a pharmaceutically acceptable salt, N-oxide, stereoisomer, diastereoisomer, enantiomer or atropisomer.

2. The compound of claim 1, wherein R¹ is hydroxyphenyl, hydroxy-methoxyphenyl, hydroxy-bromophenyl, hydroxy-chlorophenyl, fluorophenyl, bromophenyl, chlorophenyl, phenyl, methoxyphenyl, difluoro-hydroxyphenyl, ethoxyphenyl, or bromo-hydroxy-methoxyphenyl.

3. The compound of claim 1, wherein R¹ is 2-hydroxyphenyl, 2-hydroxy-3-methoxyphenyl, 2-hydroxy-5-methoxyphenyl, 2-hydroxy-5-bromophenyl, 2-hydroxy-5-chlorophenyl, 4-fluorophenyl, 4-bromophenyl, 2-fluorophenyl, 3-fluorophenyl, 4-chlorophenyl, phenyl, 3-hydroxyphenyl, 2-methoxyphenyl, 3,5-difluoro-2-hydroxyphenyl, 4-ethoxyphenyl or 2-bromo-3-hydroxy-4-methoxyphenyl.

4. The compound of claim 1, wherein R² is H, 5-methoxy, 7-methoxy, 7-bromo, or 7-chloro.

5. The compound of claim 1, wherein R² is H, 5-methoxy, 7-methoxy, 7-bromo, 7-chloro, or 7-fluoro.

6. The compound of claim 1 having the structure:

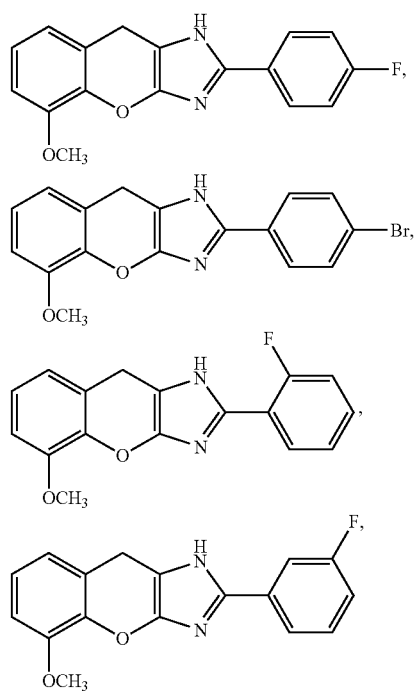

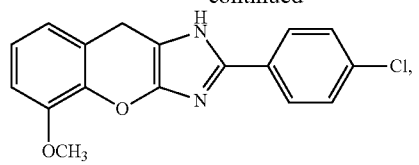
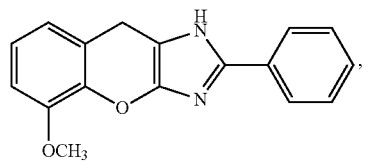
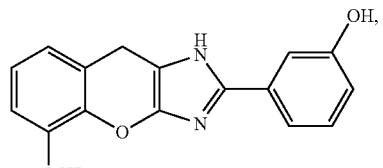
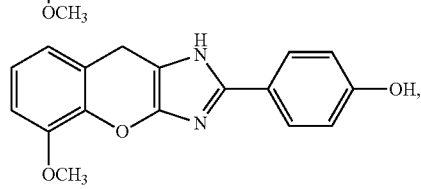
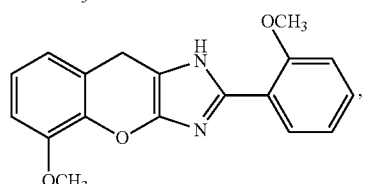
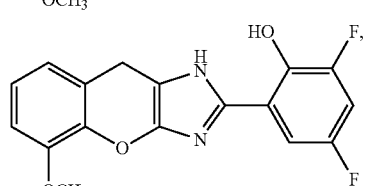
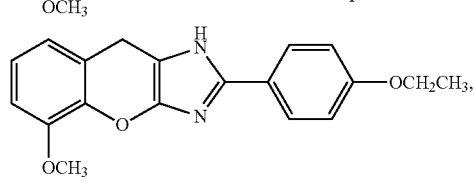
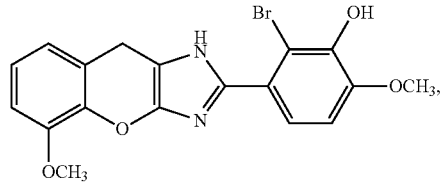
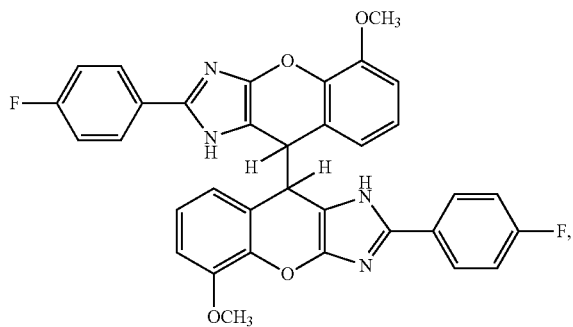

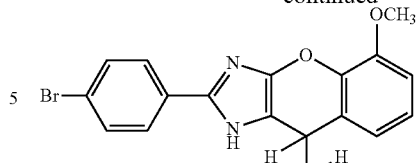
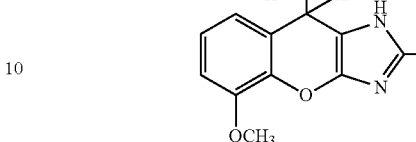
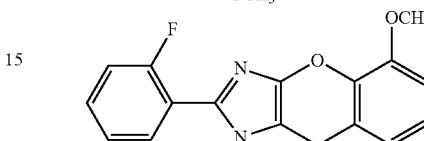
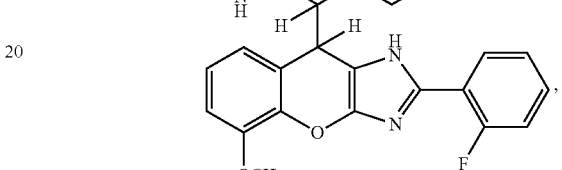

or a pharmaceutically acceptable salt, N-oxide, stereoisomer, diastereoisomer, enantiomer or atropisomer.

7. A pharmaceutical composition comprising the compound of claim 1 and a pharmaceutically acceptable carrier.

8. A method for treating a disease characterized by being a cancer in a subject afflicted therewith comprising administering to the subject an effective amount of the compound of claim 1, wherein the disease characterized by a cancer is breast cancer, renal cell carcinoma, leukemia, glioma or glioblastoma.

9. A method of treating a subject afflicted with triple-negative breast cancer, luminal breast cancer, a basal like breast cancer, renal cell carcinoma or acute leukemia, comprising administering to the subject an effective amount of a compound having the structure:

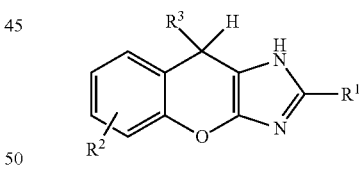

wherein
$R^1$ is aryl, substituted aryl, or substituted phenyl;
$R^2$ is H, alkyl, alkoxyl, halogen, hydroxyl, amine;
$R^3$ is H or

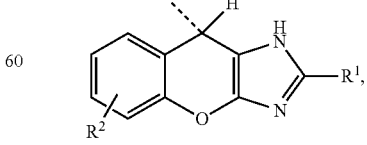

or a pharmaceutically acceptable salt, N-oxide, stereoisomer, diastereoisomer, enantiomer or atropisomer thereof, so as to thereby treat a subject.

10. The method of claim 9, wherein the compound has the structure:
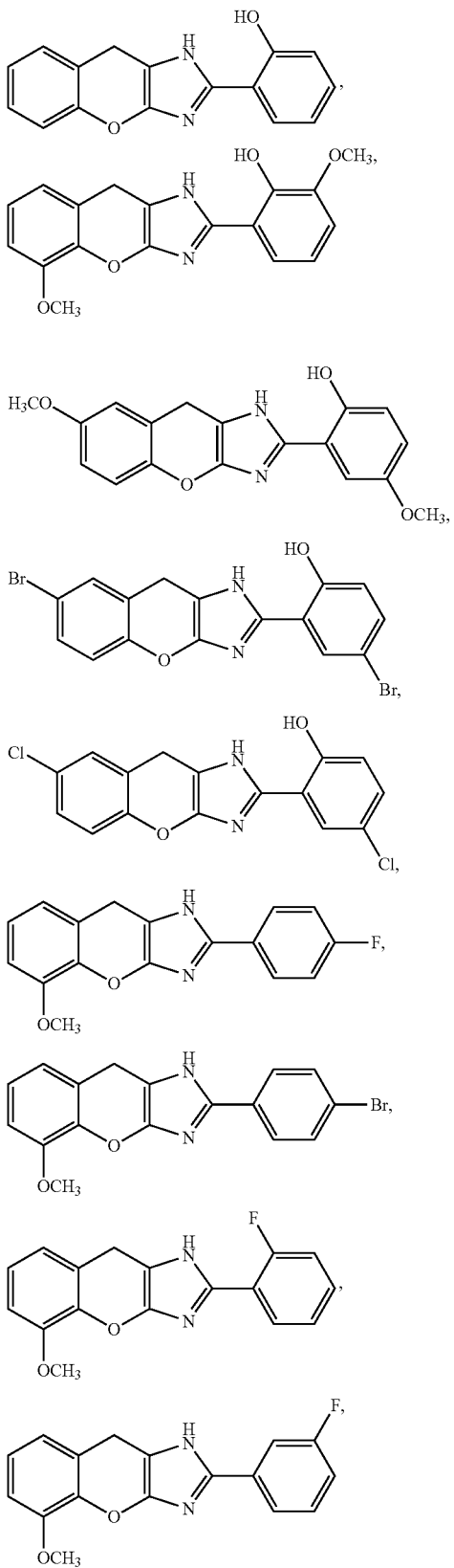
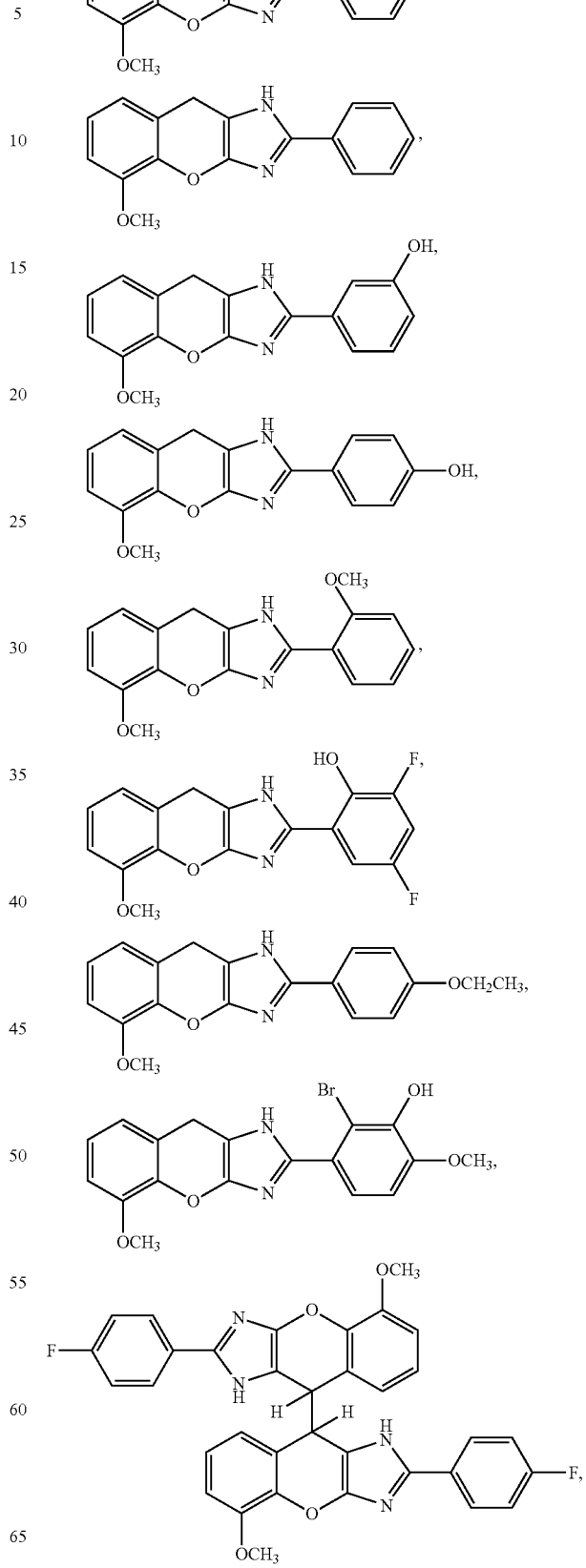

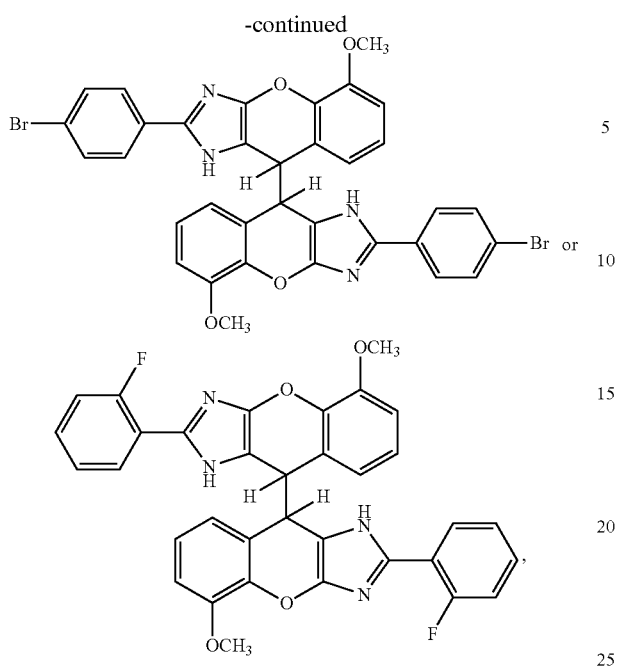

or a pharmaceutically acceptable salt, N-oxide, stereoisomer, diastereoisomer, enantiomer or atropisomer.

11. A process for producing a compound of claim 1 having the structure:

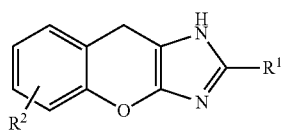

said process comprising a step of reacting a compound having the structure:

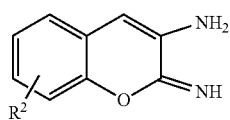

with concentrated hydrochloric acid in an organic solvent to produce a compound having the structure:

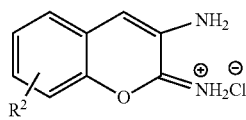

then reacting it with an aldehyde having the structure $R^1$—CHO in an organic solvent to produce a compound having the structure:

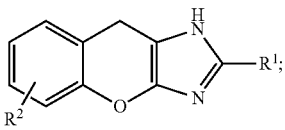

or a process for producing a compound of claim 1 having the structure:

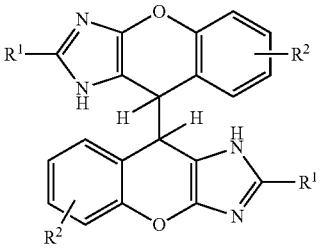

said process comprising a step of reacting a compound having the structure:

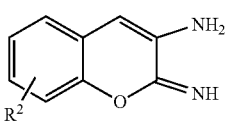

with an aldehyde having the structure $R^1$—CHO in an organic solvent to produce a compound having the structure:

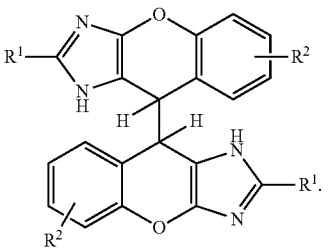

* * * * *